(12) United States Patent
Stankus et al.

(10) Patent No.: US 12,403,291 B2
(45) Date of Patent: Sep. 2, 2025

(54) SUBMUCOSAL BIORESORBABLE DRUG ELUTING PLATFORM

(71) Applicant: Intersect ENT, Inc., Menlo Park, CA (US)

(72) Inventors: John Joseph Stankus, San Jose, CA (US); James Su, Newark, CA (US); Anthony J. Abbate, Campbell, CA (US); Tu Duc Ngo, San Jose, CA (US); Diego Javier Garnica, Sunnyvale, CA (US); Rahul Bitla, Fremont, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 1271 days.

(21) Appl. No.: 17/004,753

(22) Filed: Aug. 27, 2020

(65) Prior Publication Data
US 2021/0060316 A1    Mar. 4, 2021

Related U.S. Application Data

(60) Provisional application No. 62/894,113, filed on Aug. 30, 2019.

(51) Int. Cl.
*A61M 31/00*       (2006.01)
*A61K 9/70*        (2006.01)
(Continued)

(52) U.S. Cl.
CPC ........... *A61M 31/00* (2013.01); *A61K 9/7007* (2013.01); *A61K 31/58* (2013.01); *A61K 47/34* (2013.01);
(Continued)

(58) Field of Classification Search
CPC .... A61F 2250/0067; A61F 2210/0004; A61M 31/00; A61M 2210/0618;
(Continued)

(56) References Cited

U.S. PATENT DOCUMENTS 374,026 A    11/1887    Williams
1,381,829 A   6/1921    Hartman
(Continued)

FOREIGN PATENT DOCUMENTS

CN    101610753 A    12/2009
CN    103079544 A     5/2013
(Continued)

OTHER PUBLICATIONS

Chinese Office Action issued in corresponding Chinese Application No. 202080069064.0 dated Jul. 28, 2023, 34 pages.
(Continued)

*Primary Examiner* — Kevin C Sirmons
*Assistant Examiner* — Alexandra Lalonde
(74) *Attorney, Agent, or Firm* — Carter, DeLuca & Farrell LLP

(57) ABSTRACT

Systems and methods for delivering a therapeutic agent to target tissue using a plurality of drug delivery platforms each having a polymer scaffold and the therapeutic agent contained within the polymer scaffold. Each drug delivery platform of the plurality of drug delivery platforms is implanted into the target tissue, allowing the therapeutic agent to elute from each drug delivery platform of the plurality of drug delivery platforms for a target period of time, delivering a therapeutic dose of the therapeutic agent for the target period of time. Each drug delivery platform of the plurality of drug delivery platforms is allowed to biodegrade within the target tissue.

26 Claims, 24 Drawing Sheets

(51) Int. Cl.
  *A61K 31/58* (2006.01)
  *A61K 47/34* (2017.01)
(52) U.S. Cl.
  CPC .............. *A61M 2210/0618* (2013.01); *A61M 2210/065* (2013.01); *A61M 2210/0656* (2013.01); *A61M 2210/0662* (2013.01); *A61M 2210/0668* (2013.01); *A61M 2210/0675* (2013.01); *A61M 2210/0681* (2013.01); *A61M 2210/1028* (2013.01); *A61M 2210/1032* (2013.01); *A61M 2210/105* (2013.01)
(58) Field of Classification Search
  CPC .... A61M 2210/065; A61M 2210/0662; A61M 2210/0668; A61M 2210/0675; A61M 2210/0681; A61M 2210/1028; A61M 2210/1032; A61M 2210/105; A61M 2210/0656; A61M 37/00; A61M 37/0069; A61M 29/00; A61M 2205/04; A61M 5/3286; A61K 9/7007; A61K 9/0043; A61K 9/0024; A61K 31/58; A61K 47/34; A61B 17/24; A61B 17/3468
  See application file for complete search history.

(56) References Cited

U.S. PATENT DOCUMENTS

| | | |
|---|---|---|
| 1,485,126 A | 2/1924 | Schumacher |
| 1,520,908 A | 12/1924 | Meyer |
| 1,658,801 A | 2/1928 | Condren |
| 2,009,393 A | 7/1935 | Failla |
| 2,096,162 A | 10/1937 | Daley |
| 2,691,985 A | 10/1954 | Newsom |
| 3,049,125 A | 8/1962 | Kriwkowitsch |
| 3,473,165 A | 10/1969 | Gran et al. |
| 3,502,078 A | 3/1970 | Hill et al. |
| 3,570,494 A | 3/1971 | Gottschalk |
| 3,583,391 A | 6/1971 | Cox et al. |
| 3,766,924 A | 10/1973 | Pidgeon |
| 3,800,788 A | 4/1974 | White |
| 3,894,539 A | 7/1975 | Tallent |
| 3,903,893 A | 9/1975 | Scheer |
| 3,913,584 A | 10/1975 | Nalchle et al. |
| 4,094,303 A | 6/1978 | Johnston |
| 4,245,652 A | 1/1981 | Kelly et al. |
| 4,389,208 A | 6/1983 | LeVeen et al. |
| 4,419,095 A | 12/1983 | Nebergall et al. |
| 4,451,254 A | 5/1984 | Dinius et al. |
| D276,937 S | 12/1984 | Griggs |
| 4,534,761 A | 8/1985 | Raible |
| 4,580,568 A | 4/1986 | Gianturco |
| 4,604,920 A | 8/1986 | Dupke |
| 4,627,971 A | 12/1986 | Ayer |
| 4,650,488 A | 3/1987 | Bays et al. |
| 4,655,771 A | 4/1987 | Wallsten |
| 4,704,126 A | 11/1987 | Baswell et al. |
| 4,737,141 A | 4/1988 | Spits |
| 4,744,792 A | 5/1988 | Sander et al. |
| 4,753,636 A | 6/1988 | Free |
| 4,793,351 A | 12/1988 | Andman et al. |
| 4,886,493 A | 12/1989 | Yee |
| 4,941,881 A | 7/1990 | Masters et al. |
| 4,964,850 A | 10/1990 | Bouton et al. |
| 5,000,957 A | 3/1991 | Eckenhoff et al. |
| 5,011,474 A | 4/1991 | Brennan |
| 5,035,706 A | 7/1991 | Giantureo et al. |
| 5,062,829 A | 11/1991 | Pryor et al. |
| 5,116,311 A | 5/1992 | Lofstedt |
| 5,139,502 A | 8/1992 | Berg et al. |
| 5,139,510 A | 8/1992 | Goldsmith et al. |
| 5,139,832 A | 8/1992 | Hayashi et al. |
| 5,167,614 A | 12/1992 | Tessmann et al. |
| 5,189,110 A | 2/1993 | Ikematu et al. |
| 5,217,484 A | 6/1993 | Marks |
| 5,246,455 A | 9/1993 | Shikani |
| 5,256,146 A | 10/1993 | Ensminger et al. |
| 5,300,119 A | 4/1994 | Blom |
| 5,312,813 A | 5/1994 | Costerton et al. |
| 5,336,163 A | 8/1994 | DeMane et al. |
| 5,342,296 A | 8/1994 | Persson et al. |
| 5,348,553 A | 9/1994 | Whitney |
| 5,350,580 A | 9/1994 | Muchow et al. |
| 5,391,179 A | 2/1995 | Mezzoli |
| 5,443,498 A | 8/1995 | Fontaine |
| 5,501,700 A | 3/1996 | Hirata |
| 5,507,210 A | 4/1996 | Paramest |
| 5,507,807 A | 4/1996 | Shippert |
| 5,512,055 A | 4/1996 | Domb et al. |
| 5,538,738 A | 7/1996 | Ritter et al. |
| 5,540,712 A | 7/1996 | Kleshinski et al. |
| 5,556,413 A | 9/1996 | Lam |
| 5,632,762 A | 5/1997 | Myler |
| 5,645,584 A | 7/1997 | Suyama |
| 5,664,567 A | 9/1997 | Linder |
| 5,672,179 A | 9/1997 | Garth et al. |
| 5,693,065 A | 12/1997 | Rains, III |
| 5,713,855 A | 2/1998 | Shippert |
| 5,746,224 A | 5/1998 | Edwards |
| 5,749,921 A | 5/1998 | Lenker et al. |
| 5,792,100 A | 8/1998 | Shantha |
| 5,800,379 A | 9/1998 | Edwards |
| 5,800,429 A | 9/1998 | Edwards |
| 5,827,224 A | 10/1998 | Shippert |
| 5,895,408 A | 4/1999 | Pagan |
| 5,899,878 A | 5/1999 | Glassman |
| 5,928,190 A | 7/1999 | Davis |
| 5,992,000 A | 11/1999 | Humphrey et al. |
| 6,033,436 A | 3/2000 | Steinke et al. |
| 6,054,122 A | 4/2000 | MacPhee et al. |
| 6,063,102 A | 5/2000 | Morales |
| 6,074,381 A | 6/2000 | Dinh et al. |
| 6,082,990 A | 7/2000 | Jackson et al. |
| 6,092,273 A | 7/2000 | Villareal |
| 6,092,528 A | 7/2000 | Edwards |
| 6,108,886 A | 8/2000 | Kimes et al. |
| 6,113,641 A | 9/2000 | Leroy et al. |
| 6,123,697 A | 9/2000 | Shippert |
| 6,149,681 A | 11/2000 | Houser et al. |
| 6,149,944 A | 11/2000 | Jeong et al. |
| 6,152,946 A | 11/2000 | Broome et al. |
| 6,180,848 B1 | 1/2001 | Flament et al. |
| 6,190,353 B1 | 2/2001 | Makower et al. |
| 6,195,225 B1 | 2/2001 | Komatsu et al. |
| 6,200,335 B1 | 3/2001 | Igaki |
| 6,224,626 B1 | 5/2001 | Steinke |
| 6,228,111 B1 | 5/2001 | Tormala et al. |
| 6,280,413 B1 | 8/2001 | Clark et al. |
| 6,290,728 B1 | 9/2001 | Phelps et al. |
| 6,297,227 B1 | 10/2001 | Johnson |
| 6,302,875 B1 | 10/2001 | Makower et al. |
| 6,306,084 B1 | 10/2001 | Pinczower |
| 6,319,512 B1 | 11/2001 | Rothen-Weinhold et al. |
| 6,329,386 B1 | 12/2001 | Mollison |
| 6,342,068 B1 | 1/2002 | Thompson |
| 6,347,241 B2 | 2/2002 | Burbank et al. |
| 6,350,465 B1 | 2/2002 | Jonnalagadda et al. |
| 6,352,547 B1 | 3/2002 | Brown et al. |
| 6,355,032 B1 | 3/2002 | Hovda et al. |
| 6,375,615 B1 | 4/2002 | Flaherty et al. |
| 6,386,197 B1 | 5/2002 | Miller |
| 6,398,758 B1 | 6/2002 | Jacobsen et al. |
| 6,409,750 B1 | 6/2002 | Hyodoh et al. |
| 6,447,539 B1 | 9/2002 | Nelson et al. |
| 6,491,940 B1 | 12/2002 | Levin |
| 6,524,608 B2 | 2/2003 | Ottoboni et al. |
| 6,537,294 B1 | 3/2003 | Boyle et al. |
| 6,543,452 B1 | 4/2003 | Lavigne |
| 6,544,230 B1 | 4/2003 | Flaherty et al. |
| 6,555,566 B2 | 4/2003 | Ponikau |
| 6,562,058 B2 | 5/2003 | Seguin et al. |
| 6,565,597 B1 | 5/2003 | Fearnot et al. |
| 6,589,286 B1 | 7/2003 | Litner |
| 6,591,838 B2 | 7/2003 | Durgin |

(56) References Cited

U.S. PATENT DOCUMENTS

| | | |
|---|---|---|
| 6,605,294 B2 | 8/2003 | Sawhney |
| 6,606,995 B1 | 8/2003 | Sadek et al. |
| 6,618,921 B1 | 9/2003 | Thornton |
| 6,685,648 B2 | 2/2004 | Flaherty et al. |
| 6,692,455 B2 | 2/2004 | Goode et al. |
| 6,695,856 B2 | 2/2004 | Kieturakis et al. |
| 6,709,465 B2 | 3/2004 | Mitchell et al. |
| 6,712,859 B2 | 3/2004 | Rousseau et al. |
| 6,715,485 B1 | 4/2004 | Djupesland et al. |
| 6,719,934 B2 | 4/2004 | Stinson |
| 6,746,426 B1 | 6/2004 | Flaherty et al. |
| 6,749,617 B1 | 6/2004 | Palasis et al. |
| 6,884,260 B2 | 4/2005 | Kugler et al. |
| 6,942,690 B1 | 9/2005 | Pollock et al. |
| 6,945,992 B2 | 9/2005 | Goodson, IV et al. |
| 6,951,053 B2 | 10/2005 | Padilla et al. |
| 6,966,923 B2 | 11/2005 | Gittings |
| 7,018,401 B1 | 3/2006 | Hyodoh et al. |
| 7,072,720 B2 | 7/2006 | Puskas |
| 7,074,426 B2 | 7/2006 | Kochinke |
| 7,108,706 B2 | 9/2006 | Hogle |
| RE39,321 E | 10/2006 | MacPhee et al. |
| 7,195,016 B2 | 3/2007 | Loyd et al. |
| 7,225,518 B2 | 6/2007 | Fidenschink et al. |
| 7,235,099 B1 | 6/2007 | Duncavage et al. |
| 7,249,390 B2 | 7/2007 | Yale et al. |
| RE39,923 E | 11/2007 | Blom |
| 7,314,484 B2 | 1/2008 | Deem et al. |
| 7,316,147 B2 | 1/2008 | Perreault et al. |
| 7,361,168 B2 | 4/2008 | Makower et al. |
| 7,410,480 B2 | 8/2008 | Muni et al. |
| 7,419,497 B2 | 9/2008 | Muni et al. |
| 7,451,765 B2 | 11/2008 | Adler |
| 7,462,175 B2 | 12/2008 | Chang et al. |
| 7,500,971 B2 | 3/2009 | Chang et al. |
| 7,520,876 B2 | 4/2009 | Ressemann et al. |
| 7,544,192 B2 | 6/2009 | Eaton et al. |
| 7,559,925 B2 | 7/2009 | Goldfarb et al. |
| 7,641,644 B2 | 1/2010 | Chang et al. |
| 7,641,688 B2 | 1/2010 | Lesh |
| 7,645,272 B2 | 1/2010 | Chang et al. |
| 7,651,696 B2 | 1/2010 | Bates |
| 7,654,997 B2 | 2/2010 | Makower et al. |
| 7,658,758 B2 | 2/2010 | Diaz et al. |
| 7,658,764 B2 | 2/2010 | Reitan et al. |
| 7,662,141 B2 | 2/2010 | Eaton et al. |
| 7,662,142 B2 | 2/2010 | Eaton et al. |
| 7,686,798 B2 | 3/2010 | Eaton et al. |
| 7,691,094 B2 | 4/2010 | Eaton et al. |
| 7,713,255 B2 | 5/2010 | Eaton et al. |
| 7,717,933 B2 | 5/2010 | Becker |
| 7,740,642 B2 | 6/2010 | Becker |
| 7,753,929 B2 | 7/2010 | Becker |
| 7,771,482 B1 | 8/2010 | Karmon |
| 7,815,928 B2 | 10/2010 | Cherif Cheikh |
| 7,951,130 B2 | 5/2011 | Eaton et al. |
| 7,951,131 B2 | 5/2011 | Eaton et al. |
| 7,951,132 B2 | 5/2011 | Eaton et al. |
| 7,951,133 B2 | 5/2011 | Eaton et al. |
| 7,951,134 B2 | 5/2011 | Eaton et al. |
| 7,951,135 B2 | 5/2011 | Eaton et al. |
| 8,025,635 B2 | 9/2011 | Eaton et al. |
| 8,088,120 B2 | 1/2012 | Worsoff |
| 8,109,918 B2 | 2/2012 | Eaton et al. |
| 8,192,450 B2 | 6/2012 | Gonzales et al. |
| 8,197,433 B2 | 6/2012 | Cohen |
| 8,303,640 B2 | 11/2012 | Hepworth et al. |
| 8,337,454 B2 | 12/2012 | Eaton et al. |
| 8,500,776 B2 | 8/2013 | Ebner |
| 8,535,707 B2 | 9/2013 | Arensdorf et al. |
| 8,585,730 B2 | 11/2013 | Eaton et al. |
| 8,585,731 B2 | 11/2013 | Abbate et al. |
| 8,585,753 B2 | 11/2013 | Scanlon et al. |
| 8,721,591 B2 | 5/2014 | Chang et al. |
| 8,740,029 B2 | 6/2014 | Barnoski et al. |
| 8,740,839 B2 | 6/2014 | Eaton et al. |
| 8,740,929 B2 | 6/2014 | Gopferich et al. |
| 8,763,222 B2 | 7/2014 | Abbate et al. |
| 8,802,131 B2 | 8/2014 | Arensdorf et al. |
| 8,858,974 B2 | 10/2014 | Eaton et al. |
| 8,986,341 B2 | 3/2015 | Abbate et al. |
| 8,999,368 B2 | 4/2015 | McDonald et al. |
| 9,585,681 B2 | 3/2017 | Eaton et al. |
| 9,782,283 B2 | 10/2017 | Abbate et al. |
| 10,010,651 B2 | 7/2018 | Eaton et al. |
| 10,357,640 B2 | 7/2019 | Abbate |
| 10,471,185 B2 | 11/2019 | Eaton et al. |
| 2001/0021871 A1 | 9/2001 | Stinson |
| 2002/0022048 A1 | 2/2002 | Bromberg et al. |
| 2002/0051793 A1 | 5/2002 | Drabick |
| 2002/0051845 A1 | 5/2002 | Mehta et al. |
| 2002/0077693 A1 | 6/2002 | Barclay et al. |
| 2002/0111603 A1 | 8/2002 | Cheikh |
| 2002/0143387 A1 | 10/2002 | Soetikno et al. |
| 2002/0188344 A1 | 12/2002 | Bolea et al. |
| 2002/0198586 A1 | 12/2002 | Inoue |
| 2003/0033001 A1 | 2/2003 | Igaki |
| 2003/0040790 A1 | 2/2003 | Furst |
| 2003/0055488 A1 | 3/2003 | Igaki |
| 2003/0065346 A1 | 4/2003 | Evens et al. |
| 2003/0070682 A1 | 4/2003 | Wilson et al. |
| 2003/0105469 A1 | 6/2003 | Karmon |
| 2003/0109837 A1 | 6/2003 | McBride-Sakal |
| 2003/0125774 A1 | 7/2003 | Salo |
| 2003/0133877 A1 | 7/2003 | Levin |
| 2003/0135266 A1 | 7/2003 | Chew et al. |
| 2003/0135268 A1 | 7/2003 | Desai |
| 2003/0135970 A1 | 7/2003 | Thornton |
| 2003/0147954 A1 | 8/2003 | Yang et al. |
| 2003/0158598 A1 | 8/2003 | Ashton |
| 2003/0195459 A1 | 10/2003 | Shippert |
| 2003/0203030 A1 | 10/2003 | Ashton et al. |
| 2003/0209835 A1 | 11/2003 | Chun et al. |
| 2003/0236570 A1 | 12/2003 | Cook et al. |
| 2004/0043052 A1 | 3/2004 | Hunter et al. |
| 2004/0064083 A1 | 4/2004 | Becker |
| 2004/0064150 A1 | 4/2004 | Becker |
| 2004/0093062 A1 | 5/2004 | Glastra |
| 2004/0116958 A1 | 6/2004 | Gopferich et al. |
| 2004/0117004 A1 | 6/2004 | Osborne et al. |
| 2004/0133270 A1 | 7/2004 | Grandt |
| 2004/0137059 A1 | 7/2004 | Nivaggioli et al. |
| 2004/0176827 A1 | 9/2004 | Jacobson et al. |
| 2004/0236415 A1 | 11/2004 | Thomas |
| 2005/0038497 A1 | 2/2005 | Neuendorf et al. |
| 2005/0043706 A1 | 2/2005 | Eaton et al. |
| 2005/0043783 A1 | 2/2005 | Amis et al. |
| 2005/0119725 A1 | 6/2005 | Wang et al. |
| 2005/0124560 A1 | 6/2005 | Sung et al. |
| 2005/0131460 A1 | 6/2005 | Gifford et al. |
| 2005/0131514 A1 | 6/2005 | Hijlkema et al. |
| 2005/0131524 A1 | 6/2005 | Majercak et al. |
| 2005/0131525 A1 | 6/2005 | Hartley |
| 2005/0143817 A1 | 6/2005 | Hunter et al. |
| 2005/0163821 A1 | 7/2005 | Sung et al. |
| 2005/0165347 A1 | 7/2005 | Bardy |
| 2005/0203605 A1 | 9/2005 | Dolan |
| 2005/0229670 A1 | 10/2005 | Perreault |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0025849 A1 | 2/2006 | Kaplan |
| 2006/0063973 A1 | 3/2006 | Makower et al. |
| 2006/0095066 A1 | 5/2006 | Chang et al. |
| 2006/0106361 A1 | 5/2006 | Muni et al. |
| 2006/0135981 A1 | 6/2006 | Lenker et al. |
| 2006/0142736 A1 | 6/2006 | Hissink et al. |
| 2006/0162722 A1 | 7/2006 | Boehm et al. |
| 2006/0167540 A1 | 7/2006 | Masters et al. |
| 2006/0210605 A1 | 9/2006 | Chang et al. |
| 2006/0247499 A1 | 11/2006 | Butler et al. |
| 2006/0265042 A1 | 11/2006 | Catanese et al. |
| 2006/0276871 A1 | 12/2006 | Lamson et al. |

(56) References Cited

U.S. PATENT DOCUMENTS

| | | |
|---|---|---|
| 2007/0005094 A1 | 1/2007 | Eaton et al. |
| 2007/0014830 A1 | 1/2007 | Tijsma et al. |
| 2007/0055346 A1 | 3/2007 | Pryor |
| 2007/0055348 A1 | 3/2007 | Pryor |
| 2007/0079494 A1 | 4/2007 | Serrano |
| 2007/0100435 A1 | 5/2007 | Case et al. |
| 2007/0106366 A1 | 5/2007 | Delaloye et al. |
| 2007/0110788 A1 | 5/2007 | Hissong et al. |
| 2007/0129751 A1 | 6/2007 | Muni et al. |
| 2007/0135789 A1 | 6/2007 | Chang et al. |
| 2007/0156211 A1 | 7/2007 | Ferren et al. |
| 2007/0156229 A1 | 7/2007 | Park |
| 2007/0162100 A1 | 7/2007 | Gabbay |
| 2007/0167682 A1 | 7/2007 | Goldfarb et al. |
| 2007/0179599 A1 | 8/2007 | Brodbeck et al. |
| 2007/0191922 A1 | 8/2007 | Hartley |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0227544 A1 | 10/2007 | Betsy et al. |
| 2007/0233225 A1 | 10/2007 | Rapacki et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0270941 A1 | 11/2007 | Headley et al. |
| 2007/0282305 A1 | 12/2007 | Goldfarb et al. |
| 2007/0289677 A1 | 12/2007 | Ma et al. |
| 2007/0293726 A1 | 12/2007 | Goldfarb et al. |
| 2007/0293727 A1 | 12/2007 | Goldfarb et al. |
| 2007/0293946 A1 | 12/2007 | Gonzales et al. |
| 2007/0297186 A1 | 12/2007 | Hoover et al. |
| 2007/0299043 A1 | 12/2007 | Hunter et al. |
| 2008/0015540 A1 | 1/2008 | Muni et al. |
| 2008/0058295 A1 | 3/2008 | Chaudry |
| 2008/0058296 A1 | 3/2008 | Chaudry |
| 2008/0069858 A1 | 3/2008 | Weber |
| 2008/0077226 A1 | 3/2008 | Ouellette et al. |
| 2008/0077230 A1 | 3/2008 | Heaney et al. |
| 2008/0082162 A1 | 4/2008 | Boismier et al. |
| 2008/0085293 A1 | 4/2008 | Yang |
| 2008/0087239 A1 | 4/2008 | Chang et al. |
| 2008/0087295 A1 | 4/2008 | Makower et al. |
| 2008/0089952 A1 | 4/2008 | Hunter et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0097568 A1 | 4/2008 | Savage et al. |
| 2008/0097575 A1 | 4/2008 | Cottone |
| 2008/0097576 A1 | 4/2008 | Cottone et al. |
| 2008/0097580 A1 | 4/2008 | Dave |
| 2008/0097581 A1 | 4/2008 | Shanley |
| 2008/0097591 A1 | 4/2008 | Savage et al. |
| 2008/0103361 A1 | 5/2008 | Makower et al. |
| 2008/0103521 A1 | 5/2008 | Makower et al. |
| 2008/0103584 A1 | 5/2008 | Su et al. |
| 2008/0113000 A1 | 5/2008 | Hunter et al. |
| 2008/0119693 A1 | 5/2008 | Makower et al. |
| 2008/0125626 A1 | 5/2008 | Chang et al. |
| 2008/0125720 A1 | 5/2008 | Kim et al. |
| 2008/0132938 A1 | 6/2008 | Chang et al. |
| 2008/0145514 A1 | 6/2008 | Hunter et al. |
| 2008/0154237 A1 | 6/2008 | Chang et al. |
| 2008/0154250 A1 | 6/2008 | Makower et al. |
| 2008/0183128 A1 | 7/2008 | Morriss et al. |
| 2008/0195041 A1 | 8/2008 | Goldfarb et al. |
| 2008/0195189 A1 | 8/2008 | Asgari |
| 2008/0228085 A1 | 9/2008 | Jenkins et al. |
| 2008/0234720 A1 | 9/2008 | Chang et al. |
| 2008/0243140 A1 | 10/2008 | Gopferich et al. |
| 2008/0262468 A1 | 10/2008 | Clifford et al. |
| 2008/0262505 A1 | 10/2008 | Shahoian |
| 2008/0262508 A1 | 10/2008 | Clifford et al. |
| 2008/0262509 A1 | 10/2008 | Clifford et al. |
| 2008/0262510 A1 | 10/2008 | Clifford |
| 2008/0262593 A1 | 10/2008 | Ryan et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0306579 A1 | 12/2008 | Dolan et al. |
| 2008/0319424 A1 | 12/2008 | Muni et al. |
| 2009/0004272 A1 | 1/2009 | Gibson et al. |
| 2009/0004273 A1 | 1/2009 | Gibson et al. |
| 2009/0005763 A1 | 1/2009 | Makower et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0035351 A1 | 2/2009 | Berglund et al. |
| 2009/0036968 A1 | 2/2009 | Hepworth et al. |
| 2009/0036974 A1 | 2/2009 | Penn et al. |
| 2009/0041824 A1 | 2/2009 | Zugates et al. |
| 2009/0047326 A1 | 2/2009 | Eaton et al. |
| 2009/0047327 A1 | 2/2009 | Eaton et al. |
| 2009/0056709 A1 | 3/2009 | Worsoff |
| 2009/0093823 A1 | 4/2009 | Chang et al. |
| 2009/0104243 A1* | 4/2009 | Utkhede ............... A61F 9/0017 424/423 |
| 2009/0156980 A1 | 6/2009 | Eaton et al. |
| 2009/0177272 A1 | 7/2009 | Abbate et al. |
| 2009/0187098 A1 | 7/2009 | Makower et al. |
| 2009/0192488 A1 | 7/2009 | Eaton et al. |
| 2009/0192489 A1 | 7/2009 | Eaton et al. |
| 2009/0192490 A1 | 7/2009 | Eaton et al. |
| 2009/0192491 A1 | 7/2009 | Eaton et al. |
| 2009/0192492 A1 | 7/2009 | Eaton et al. |
| 2009/0198179 A1 | 8/2009 | Abbate et al. |
| 2009/0198216 A1 | 8/2009 | Muni et al. |
| 2009/0220571 A1 | 9/2009 | Eaton et al. |
| 2009/0227945 A1 | 9/2009 | Eaton et al. |
| 2009/0238859 A1 | 9/2009 | Eaton et al. |
| 2009/0240112 A1 | 9/2009 | Goldfarb et al. |
| 2009/0306624 A1 | 12/2009 | Arensdorf et al. |
| 2009/0312745 A1 | 12/2009 | Goldfarb et al. |
| 2010/0043197 A1 | 2/2010 | Abbate et al. |
| 2010/0106132 A1 | 4/2010 | Simonton |
| 2010/0239632 A1* | 9/2010 | Walsh ................. A61K 9/0043 514/289 |
| 2011/0004192 A1 | 1/2011 | Eaton et al. |
| 2011/0004193 A1 | 1/2011 | Eaton et al. |
| 2011/0004194 A1* | 1/2011 | Eaton ..................... A61P 27/16 606/199 |
| 2011/0004195 A1 | 1/2011 | Eaton et al. |
| 2011/0004196 A1 | 1/2011 | Eaton et al. |
| 2011/0021986 A1 | 1/2011 | Zamboni |
| 2011/0066135 A1 | 3/2011 | Eaton et al. |
| 2011/0112513 A1 | 5/2011 | Hester et al. |
| 2011/0167964 A1 | 7/2011 | Price |
| 2012/0064124 A1 | 3/2012 | McClain et al. |
| 2012/0089071 A1 | 4/2012 | Oliver et al. |
| 2012/0101429 A1 | 4/2012 | Eaton et al. |
| 2012/0143054 A1 | 6/2012 | Eaton et al. |
| 2013/0041463 A1 | 2/2013 | Ressemann |
| 2013/0066358 A1 | 3/2013 | Nalluri et al. |
| 2013/0231693 A1 | 9/2013 | Edgren et al. |
| 2013/0245608 A1 | 9/2013 | Muni et al. |
| 2013/0253567 A1 | 9/2013 | Edgren et al. |
| 2013/0281982 A1 | 10/2013 | Makower et al. |
| 2013/0304232 A1 | 11/2013 | Gries |
| 2014/0018839 A1 | 1/2014 | Renner et al. |
| 2014/0046255 A1 | 2/2014 | Hakimimehr et al. |
| 2014/0074065 A1 | 3/2014 | Muni et al. |
| 2014/0074238 A1 | 3/2014 | Abbate et al. |
| 2014/0079755 A1 | 3/2014 | Eaton et al. |
| 2014/0107615 A1 | 4/2014 | Doshi et al. |
| 2014/0283349 A1 | 9/2014 | Abbate et al. |
| 2014/0324025 A1 | 10/2014 | Arensdorf et al. |
| 2015/0081017 A1 | 3/2015 | Abbate et al. |
| 2015/0087671 A1 | 3/2015 | McClain et al. |
| 2015/0217097 A1 | 8/2015 | Makower et al. |
| 2016/0287854 A1 | 10/2016 | Eaton et al. |
| 2017/0056602 A1* | 3/2017 | Medina ............ A61B 17/3468 |

(56) References Cited

U.S. PATENT DOCUMENTS

| | | | |
|---|---|---|---|
| 2017/0128093 A1 | 5/2017 | Eaton et al. | |
| 2018/0264179 A1* | 9/2018 | Pan | A61L 27/52 |
| 2019/0000839 A1 | 1/2019 | Coleman et al. | |
| 2019/0083512 A1 | 3/2019 | Williams et al. | |
| 2019/0125935 A1 | 5/2019 | Eaton et al. | |
| 2019/0143087 A1 | 5/2019 | Eaton et al. | |

FOREIGN PATENT DOCUMENTS

| | | | |
|---|---|---|---|
| CN | 105209086 | A | 12/2015 |
| CN | 107949404 | A | 4/2018 |
| DE | 19608423 | A1 | 9/1997 |
| JP | 2007535535 | A | 12/2007 |
| JP | 2008509727 | A | 4/2008 |
| JP | 4223040 | B2 | 2/2009 |
| JP | 2009543778 | A | 12/2009 |
| JP | 2011508790 | A | 3/2011 |
| JP | 2018521144 | A | 8/2018 |
| JP | 2018530521 | A | 10/2018 |
| WO | 2008008389 | A2 | 1/2008 |
| WO | 2017035483 | A1 | 3/2017 |
| WO | 2018169950 | A1 | 9/2018 |

OTHER PUBLICATIONS

Extended European Search Report 20857640.5 dated Sep. 1, 2023 10pp.
Chinese Office Action issued in corresponding Chinese Application No. 202080069064.0 dated Mar. 20, 2024, 26 pages.
Chinese Rejection Decision with Search Report issued in corresponding to Chinese Application No. 202080069064.0 dated Jun. 28, 2024.
JP Office Action JP2022-513152, dated May 4, 2024, 29pp.
Mexican Office Action issued in corresponding Mexican Application No. MX/a/2022/002471 dated Nov. 6, 2024, 8 pages.
Japanese Office Action issued in corresponding Japanese Application No. 2022-513152 dated Nov. 27, 2024, 12 pages.
Australian Examination Report No. 1 issued in corresponding application No. 2020336462 dated Jan. 28, 2025 (3 pages).
European Office Action for application No. 20 857 640.5 dated Jul. 7, 2025, 7 pages.

* cited by examiner

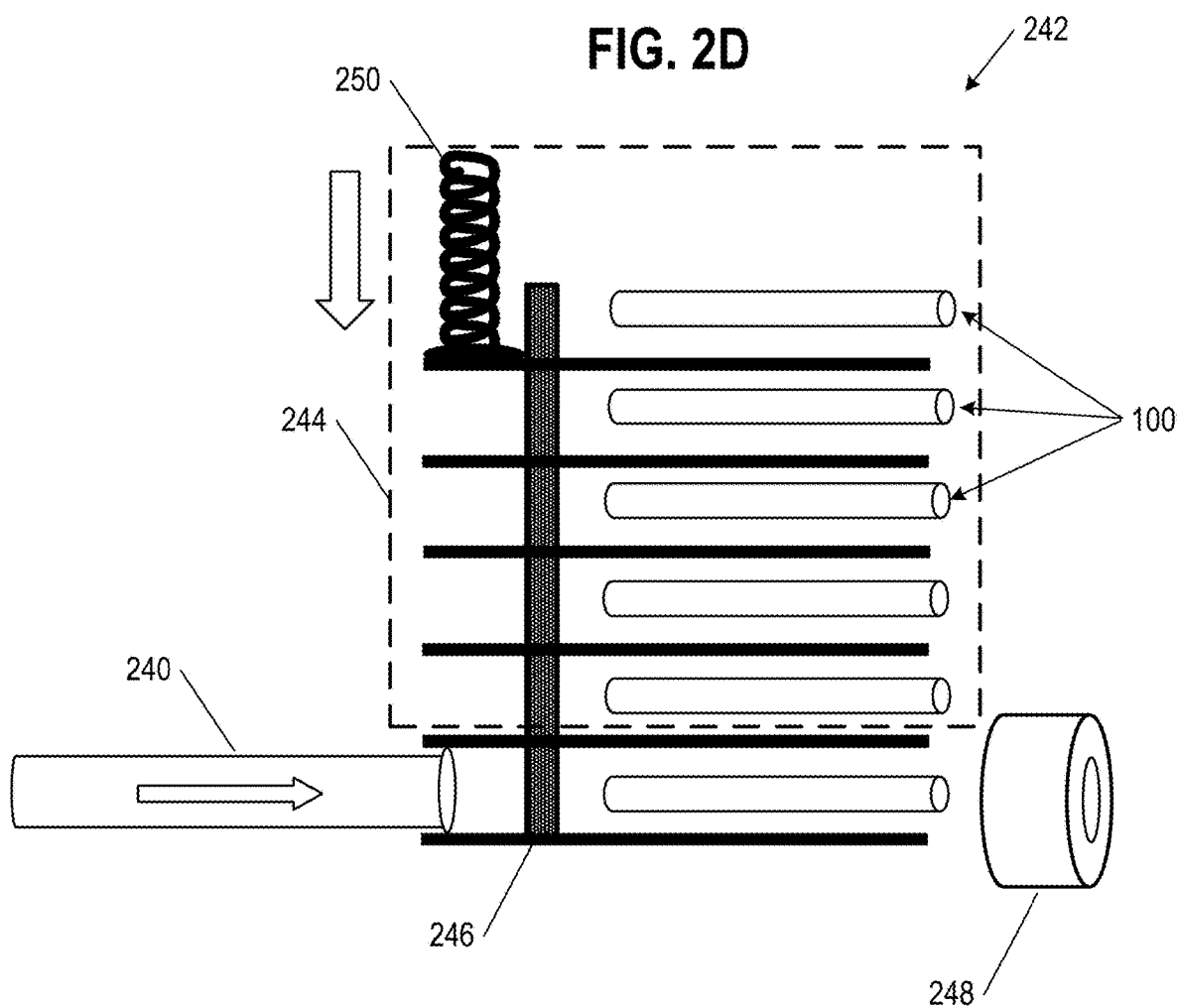

SUBMUCOSAL BIORESORBABLE DRUG ELUTING PLATFORM

RELATED APPLICATIONS

This application claims benefit of priority to U.S. provisional application 62/894,113, filed on Aug. 30, 2019, which is hereby incorporated by reference.

FIELD

This application generally relates to systems, devices, and methods for injecting or implantation of a drug delivery platform that can deliver one or more active therapeutic agents to target tissues of the ear, nose, and throat ("ENT"). The systems, devices, and methods employ a bioresorbable platform having a size and form factor appropriate for implantation into the target tissues, with the platform being embedded, coated, and/or infused with a therapeutic agent such as a drug or biologic, or a combination thereof. Upon insertion of the platform into the target tissue, a clinically meaningful dosage of the therapeutic agent is locally released into the target tissue for an extended period of time.

BACKGROUND

Rhinosinusitis is a common paranasal sinus condition that is generally understood as encompassing sinusitis and/or rhinitis. Typically, rhinosinusitis is characterized by symptoms such as nasal discharge, nasal obstruction, facial congestion, facial pain, facial pressure, loss of smell, fever, and headache. Many individuals have chronic rhinosinusitis (CRS), which is generally defined as swelling and inflammation in the sinuses, interfering with the way mucus normally drains, that lasts for three months or longer despite treatment. Chronic sinusitis can be caused by an infection, by growths in the sinuses (e.g. nasal polyps), swelling of the lining of the sinuses, or a combination thereof. Allergic rhinitis (AR), another common paranasal sinus condition, is associated with a group of symptoms affecting the nose that occurs when an individual with the condition breaths in an allergen, such as dust, mold, or animal dander. Allergens cause the release of histamine, which usually causes sneezing, itchy and watery eyes, runny nose, swelling and inflammation of the nasal passages, an increase in mucus production, and for some individuals, hives or other rashes.

Treatments for CRS often include mechanical alterations to sinus anatomy, including surgical procedures such as functional endoscopic sinus surgery (FESS), which involves trauma to a patient and a period of tissue recovery. That recovery may require further surgical procedures (revision surgery) to address procedures that do not provide for complete treatment, or to address scarring and/or nasal polyp development following surgery. Further, there are patients for whom FESS may not be an appropriate option, due to other medical considerations, a symptomatic severity of CRS that does not merit a prompt surgical procedure but will likely develop a need for surgery at a later time, or the like. In other words, a pre-FESS strategy for CRS symptoms may include delaying a surgical procedure until the need is acute.

Treatments for allergic rhinitis include oral medications, sprays, and topical applications of active agents such as antihistamines or decongestants, which have limited efficacy and duration. Allergic rhinitis can also be treated with immunotherapy regimens that can take weeks or months to complete, do not generally provide relief from symptoms at least during the beginning of the regimen, and are not guaranteed to be fully effective.

Both CRS (FESS and pre-FESS) and AR patient treatments often include the use of steroids, which can be oral steroids or steroids injected as liquids. The use of these treatments are systemic therapies which dilutes the effect of the steroid for a local target tissue and may lead to undesirable side effects from the systemic impact of the steroids. Further, it can be challenging to ensure compliance from patients who have been prescribed such steroid regimens.

Accordingly, there is a need to address CRS and other forms of non-allergic sinusitis and/or rhinitis with a durable medical therapy before implementing traditional first-line mechanical treatments of the sinus anatomy. Similarly, there is a need to address allergic rhinitis with a durable medical therapy in lieu of transitory relief from spray-based drug delivery and/or the lengthy period during an immunotherapy regimen where a patient remains symptomatic. Further, in cases where steroid treatment is appropriate, there is benefit to be had in not using steroids with a systemic impact. Moreover, given the variability in a patient consistently applying limited-duration medications (e.g., nasal sprays), there is a need to provide a medication where patient adherence is not a meaningful factor that can impair the therapy. Such a therapy would be of particular benefit for managing inflammation in individuals who are not compliant to other medication applications in order to achieve long-term symptom relief.

SUMMARY

The present disclosure is directed to an implantable drug delivery platform that provides for localized and sustained delivery of a therapeutic agent. The drug delivery platform has a relatively small form factor, as compared to the anatomical structures in which the drug delivery platform can be implanted, such that the platform is minimally irritating and/or minimally invasive to the subject receiving the implant. The size and form factor of the drug delivery platform (alternatively referred to as a "pellet", "depot", "reservoir", "implant", "rod", or the like) allows for the delivery of a uniform drug loading over a longer period of time, and at a higher dosage, than is possible by other conventional drug delivery methods (e.g. nasal sprays, drug coated implants, luminal packing materials, topical coatings, etc.). In some clinical applications, the drug delivery platform can be injected or implanted subdermally and/or submucosally into ear, nose, and/or throat tissues. The platform can be injected or implanted subdermally and/or submucosally using a needle-based delivery system, which provides for superior efficacy, safety, and patient comfort as compared to other existing therapies. In further clinical applications, the drug delivery platform can be injected or implanted into nasolacrimal tissues, or into other otic, nasal, tracheal, or esophageal tissues.

In some variations, the systems for locally delivering a therapeutically effective amount of an active agent to a target tissue can include a drug delivery platform sized and shaped for implantation or placement in an ear, nose, or throat tissue of a patient, the drug delivery platform having a rod-like structure of small size (small relative to target anatomy) with an outer diameter less than half a millimeter (<0.5 mm) and a length less than five centimeters (<5 cm) long. The drug delivery platform can have other cross-sectional shapes (e.g., square, rectangular, tubular, triangular, etc.) and/or further surface structures (e.g., ribs, angled edges, angled ends, a roughened surface, etc.) that may be utilized to enhance tissue retention. The drug delivery platform can also have a structure including one or more channels and/or ridges that impart structural strength to the platform, while also providing for spaces that can be filled or packed with amounts of an active therapeutic ingredient.

In some variations, the systems for locally delivering a therapeutically effective amount of an active agent to a target tissue can be loaded with a therapeutic agent incorporated into the drug delivery platform. Methods of forming such a drug delivery platform can include process steps such as: milling and/or reducing an excipient polymer to a target particle size; milling and/or reducing a drug (in a solid form) to a target particle size; dry mixing of the drug(s) and excipient(s); hot melt extrusion ("HME") compounding of drug (optionally with excipient) and a bioabsorbable polymer, in order to encapsulate the drug fully in the bioabsorbable polymer in a rod or pellet like form. Subsequently, the rods can be cut to a target size, loaded in delivery cartridges, and packaged with a low-profile delivery system. The overall system can be sterilized by electron beam sterilization or other suitable methods. In addition or alternatively, a system for locally delivering a therapeutically effective amount of an active agent to a target tissue can be loaded with a therapeutic agent by dissolving all components including drug, polymers, and excipients in a suitable solvent, then spray drying the appropriate surface area of the system to obtain uniform particle size mixture between drug, polymers, and excipients prior to hot melt extrusion compounding.

In some variations, the platform for locally delivering a therapeutically effective amount of an active agent to a target tissue can be configured to elute effectively the complete load of active agent over 14 days, 30 days, 60 days, 90 days, 180 days, 360 days, or 2 years. In a further variation, the platform can elute a complete load of active agent in less than 14 days, for example, in 7 days or less. In a specific exemplary embodiment, the platform can elute 25% of the active agent by 7 days (post-implantation), 50% of the active agent by 30 days, and 70% of the active agent by 90 days.

The methods described herein may include locally delivering a therapeutically effective amount of an active agent to a target tissue by placing or positioning a delivery system of small profile close to and/or apposing the target tissue, driving or plunging out the implant into a tract of the target tissue, leaving the implant within the tissue tract, and then removing or reversing the delivery device barrel.

Any active therapeutic agent used to treat an ear, nose, or throat condition may be included in the drug delivery platform, e.g., a corticosteroid may be employed. Mometasone furoate ("MF") may be a useful corticosteroid to treat rhinosinusitis. The drug delivery platform may further include excipients such as PLGA (poly(lactide-co-glycolide)), a poly(vinyl pyrrolidone), a polysorbate, a poly(ethylene glycol), propylene glycol, glycerol, glycerol caproate, or combinations or mixtures thereof.

The drug delivery platform may be used to treat inflammation of mucosal tissue, e.g., mucociliary tissue, which is present in the nasal passages and sinuses, among other structures of the respiratory system. In some variations, the condition to be treated may be a nasal condition selected from a group including post-surgical inflammation, nasal and sinus cancers, rhinosinusitis, chronic sinusitis with or without nasal polyps, and rhinitis, including both allergic and non-allergic rhinitis. In such variations, the target tissue site may be a paranasal sinus, a sinus ostium, an inferior turbinate, a middle turbinate, a superior turbinate, a nasal cavity, the nasal vestibule, the nasal septum, nasal polypoid tissues, the osteomeatal complex, the nasopharynx, adenoid tissue, or one or more of such tissues. Appropriate active agents for treating the above sinus and/or nasal conditions, including but not limited to active agents listed herein, can be compounded as part of the drug delivery platform.

In other variations, the target tissue can be otic tissues, and the condition to be treated may be an otic condition selected from a group including post-surgical inflammation, otitis media, Meniere's disease, Eustachian tube dysfunction, hearing loss, and tinnitus. In such variations, the target tissue site may be the Eustachian tube, external ear canal, middle ear, inner ear, or one or more of such tissues. Treatment of the Eustachian tube may also be beneficial in treating hearing loss, otalgia, and vertigo. Appropriate active agents for treating the above otic conditions, including but not limited to active agents listed herein, can be compounded as part of the drug delivery platform.

In other variations, the target tissue can be throat tissues (e.g., pharyngeal, esophageal, or tracheal tissues), and the condition to be treated may be a throat condition selected from a group including post-surgical pain, esophageal cancer (and other oral or pharyngeal cancers), airway stenosis (e.g., proximal tracheal stenosis or subglottic stenosis), esophageal stricture or stenosis, chronic laryngitis, tonsillitis, vocal polyps, and epiglottitis. Appropriate active agents for treating the above throat-related conditions, including but not limited to active agents listed herein, can be compounded as part of the drug delivery platform.

In further variations, the target tissue can be skin tissues, and the condition to be treated may be a dermatologic condition and/or a wound that requires healing selected from a group including, alopecia areata, discoid lupus erythematosus, keloid scarring (e.g. cut and wound scarring), hypertrophic scarring, surgical scarring (e.g., facial plastic scarring), granulomatous disorders (such as granuloma annulare), hypertrophic lichen planus, lichen simplex chronicus, localized psoriasis, necrobiosis lipoidica, acne cysts, infantile haemangiomas, and bullous pemphigoid. For such applications, the drug delivery platform may be implanted in the dermis, subdermally, or positioned in a location spanning the dermis and hypodermis/subcutaneous layer. Appropriate active agents for treating the above dermatologic conditions, including but not limited to active agents listed herein, can be compounded as part of the drug delivery platform.

It should be understood that treatment of the above-listed conditions and other medical conditions with a drug delivery platform can be responsive, preventative, or both. As an example of proactive use, a drug delivery platform may be implanted in a target tissue concurrent with completion of a surgical procedure to prevent or reduce severity of adverse physiological responses or conditions that may arise due to the surgical procedure. As an example of a reactive use, a drug delivery platform may be implanted in a target sinus tissue following symptoms of AR in a patient. It should be further understood that the drug delivery platform of the present disclosure can be configured and formulated for delivering therapy to other tissues and anatomy, such as ocular or lacrimal tissues, soft tissues in and around joints, and the like.

During manufacturing, the drug delivery platform may be infused or saturated with a drug formulation by methods including (but not limited to), spray coating, dip coating, hot melt extrusion, compounding, thermoforming, solvent casting, oil in water emulsions, injection molding, spray drying, or combinations thereof.

For improved drug layer adhesion, the platform may be cleaned with a solvent and dried prior to coating. In addition, plasma treatment with an inert gas (such as argon) or oxygen, after cleaning may increase the cleaning and wettability of the platform surface leading to increased drug layer adhesion and release of the layer upon insertion within a target tissue. In some variations, the manufacturing method can include treating the platform surface with plasma and then drying the platform with coating at room temperature or elevated temperature. In other variations, the manufacturing method can include treating platform surface with plasma and then exposing the coated platform to a solvent vapor (solvent vapor annealing).

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

FIGS. 2C, 2D, 2E, and 2F depict schematic illustrations of multi-implant loading structures for drug delivery platform implantation devices, according to aspects of the present disclosure.

DETAILED DESCRIPTION

Figure 1A:
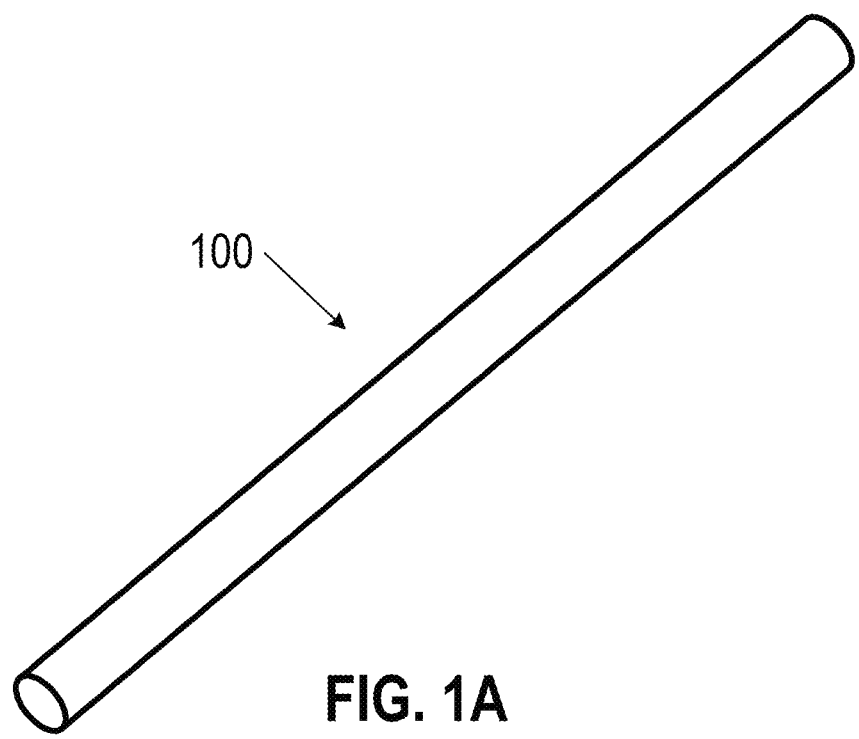
FIGS. 1A-1D depict illustrations of embodiments of an implantable drug delivery platform, according to aspects of the disclosure.

Described here are systems and methods for delivering an active agent to target tissues of the ear, nose, or throat using an implantable drug delivery platform having a therapeutic agent embedded or saturated with the active agent. In some implementations, the drug delivery platform can be coated with the therapeutic agent. The drug delivery platform can be injected or implanted into a target tissue, which then acts as an in situ drug depot, enabling maintenance of a therapeutic concentration of an active agent for a desired time period after the procedure. The drug delivery platform can be delivered submucosally and/or subdermally into the target tissues. The systems and methods may be useful when drug delivery to mucosal tissues, e.g., the paranasal sinuses, is desired. Methods for manufacturing the drug delivery platform are also described herein.

The drug delivery platform of the present disclosure is directed to an implantable drug delivery depot having a relatively small form factor which provides for local and sustained therapy within and to a target tissue. This size and characteristics of the implant make the implant minimally irritating and minimally invasive to a patient. The implantable drug delivery platform is further designed for use as a submucosal implant, which is of particular use for ear, nose, and throat applications (although the implant is not limited to use in that anatomy). Where useful or appropriate, the drug delivery platform can also be designed for use as a subdermal implant. The platform allows for a relatively high and uniform drug loading into a very small form factor, and moreover allows for a larger dose and longer-term release duration than is observed in drug coating approaches (e.g., spray-coating an implant surface with a drug). Several exemplary applications for this implantable drug delivery platform are set forth below.

In one application, the implantable drug delivery platform can be used for treatment of allergic rhinitis through submucosal implantation and delivery in an inferior turbinate. Given the local inflammation localized in the inferior turbinate and its high level of vascularization, the drug delivery platform has a distinct advantage over topical allergic rhinitis therapies at least due to higher localized total drug content, improved drug dosing, and improved drug distribution. The implantable drug delivery platform approach carries less risk than systemic therapies, given the reduced potential for systemic exposure and the reduced amount of dose needed. In further contrast with liquid injection therapies, the implantable drug delivery platform is safer given the absence of embolic risk to ocular arteries. In another application for the inferior turbinate, the implantable drug delivery platform can be used to reduce the size of a hypertrophic inferior turbinate. The implantable drug delivery platform approach is far less traumatic than mechanical or surgical approaches to reduce turbinate size. In further applications, the implantable drug delivery platform can also be similarly used for the middle turbinate and superior turbinate.

In another application, the drug delivery platform can be used for delivery of an anti-inflammatory agent, such as a corticosteroid, for reduction of inflammation post-surgery (e.g., following functional endoscopic sinus surgery) or post-mechanical procedure (e.g., dilation of a paranasal sinus or sinus ostium). The drug delivery platform can be of particular use where additional mechanical support or a permanent implant are not necessary following a sinus surgery or other nasal procedure.

In a further application, the drug delivery platform can be used for drug delivery to the Eustachian tube, before or after a procedure (e.g., balloon dilation) to treat conditions like Eustachian tube dysfunction or other diseases of the ear. In such cases, the small form factor of the drug delivery platform allows for a mode of treatment where a larger device (like a stent) would not be appropriate or would be invasive. In other otic applications, the drug delivery platform can be used to access and deliver drug to the middle ear or inner ear to treat conditions like otitis media, Meniere's disease, tinnitus, hearing loss, or other such diseases. The drug delivery platform can also be used for subdermal drug delivery to the external ear canal for chronic otitis media or swimmer's ear. In some implementations, the drug delivery platform can be implanted near, into, or within the ear drum.

In another application, the drug delivery platform can be used for drug delivery to the throat for conditions such as post-surgical pain, tonsillectomy pain, oncology, airway stenosis, chronic laryngitis, epiglottitis, other inflammatory diseases, or other diseases of the throat. As a submucosal implant, drug release from the drug delivery platform would not need to penetrate linings of the throat, and further is a safer alternative than a topical implant which potentially can be swallowed.

The therapeutic agent is generally a drug contained on and/or within the structure of the platform, where the platform is sufficiently porous such that drug contained within the platform elutes over time out from the platform and into the surrounding tissue. Drug that is directly exposed to the outer surface of the platform releases into the surrounding tissue more quickly than the drug present within the interior of the platform. The drug delivery platform thereby provides for a localized source of therapeutic agent at the site of implant.

The drug delivery platform may have several applications. It may be adapted in size, configuration, and material for different uses in different tissues, such as in the ear, nose, or throat. The drug delivery platform may be useful in treating conditions involving mucosal inflammation. In some variations, the systems and methods may be used for treating one or more sinus or nasal conditions including, but not limited to chronic rhinosinusitis, rhinitis, allergic rhinitis, acute sinusitis, and chronic sinusitis with or without polyps. In other variations, the devices and methods may be implemented during a dilation procedure. For example, one or more drugs (e.g., a corticosteroid) may be delivered via an implanted platform to reduce inflammation post balloon-ing, post dilation, or other surgery of the sinuses and/or sinus ostia. In other variations, one or more drugs may be delivered to the sinus and/or sinus ostia for relief of allergy symptoms. In yet another example, the drug delivery platform can be used for delivery of an anti-inflammatory (e.g., a corticosteroid) for reduction of inflammation post functional ethmoid surgery, including when mechanical support and a permanent implant may not be necessary.

In other variations, the systems and methods may be used for treating one or more conditions of the ear. For example, a drug delivery platform can deliver drugs to the Eustachian tube to treat Eustachian tube dysfunction. As another example, the drug delivery platform may be used for drug delivery to the external ear canal for acute otitis media, chronic otitis media or swimmer's ear. The drug delivery platform may also be used for drug delivery to the middle and/or inner ear for treatment of Meniere's disease, tinnitus, hearing loss, or other applicable conditions.

In other variations, the drug delivery platform can also have applications in the throat, where drug delivery may be for post-surgical pain, such as tonsillectomy pain, or for esophageal cancer, airway stenosis (e.g., tracheal stenosis or subglottic stenosis), chronic laryngitis, epiglottitis, other inflammatory diseases, and/or other conditions of the throat.

As used herein, the term "bioabsorption" refers to the absorption of a material by the body, generally of material that is broken down within a body tissue or cavity, which is later assimilated by the body or removed from the body. In various aspects, the bioabsorption of a material can be complete over a target or reference period of time or can be incomplete, where the material may be only partially digested and remain in a local body tissue or cavity longer than the target or reference period of time. As used herein, the terms "biodegradation" and "bioerosion" refer to the breakdown of a material in a body due mechanical strains and/or chemical processes under the physiological conditions of the biological environment. Both biodegradable and bioerodible materials may also be bioabsorbable. As used herein, the term "bioresorbable" refers inclusively to materials that are bioabsorbable, biodegradable, bioerodible, or a combination thereof.

As used herein, the term "drug delivery platform" refers to the combination of a biodegradable material that acts as the primary structural component (referred to as the "backbone", "scaffold", or "carrier") for the platform and a therapeutic component (e.g., a drug or other active agent), where the drug is loaded, infused, formed, or otherwise incorporated with the biodegradable material. Optionally, a drug delivery platform can further include excipients or release rate modifiers excipient or a polymer topcoat layer. The drug delivery platform can also be referred to as an "implant" or an "implantable drug delivery platform". In contrast, the term "delivery device" refers to an instrument used by an operator or physician to implant the drug delivery platform. The term "drug delivery system" is used to refer to the combination of drug delivery platform and the delivery device, such as when one or more implants are loaded onto a delivery device.

As used herein, the term "about" when used to modify a numerical value indicates a range of ±10% from the value, unless otherwise explicitly stated.

Devices

Implantable Drug Delivery Platform

The implantable platforms described herein are generally bioresorbable, although alternative embodiments of the implantable platforms can be entirely bioabsorbable, entirely non-bioabsorbable, or partially bioabsorbable and non-bioabsorbable. Generally, bioresorbable polymers are preferred materials such that the drug delivery platform does not have to be explanted or be extruded from a patient as a foreign body. Natural bioresorbable polymers that can be used for the structure of the drug delivery platform can include chitosan, collagen, elastin, silk, silk-elastin, alginate, cellulose, dextran, polyalkenoates, hyaluronic acid, gelatin, and gellan. When made to be bioresorbable with a synthetic material, the platform backbone may be formed from materials including, but not limited to: polylactide, poly(lactide-co-glycolide) (PLGA), poly(D,L-lactide-co-glycolide), poly (L-lactide) (PLLA), poly(lactide co-caprolactone) (PLA-PCL), polyglycolide (PGA), poly(D,L-lactide) (PDLLA), poly(L-lactide-co-caprolactone) (PLLA-PCL), polyhydroxybutyrate, polyhydroxyvalerate, poly(ethylene glycol) (PEG), polydioxanone (PDX), polyalactin, poly(ε-caprolactone), polyglyconate, poly(glycolide-co-trimethylene carbonate), poly(sebacic acid), poly(ester urethane), poly(ester urethane) urea, or combinations thereof. For some of these materials, a ratio of the constituent components can be varied to achieve certain material characteristics, such as a target bioabsorption time profile. For example, if poly(D,L-lactide-co-glycolide) is used for the scaffold of the drug delivery platform, the ratio of lactide to glycolide ("L:G") can be 5:95, 10:90, 15:85, 20:80, 25:75, 30:70, 33:67, 35:65, 40:60, 45:55, 50:50, 55:45, 60:40, 65:35, 67:33, 70:30, 75:25, 80:20, 85:15, 90:10, 95:5, or another such ratio. When made to be partially bioabsorbable, the device or a coating on the device may be bioabsorbable and can include a release rate modifier and/or a plasticizer such as polyethylene glycol, propylene glycol, polysorbates, etc. The implantable platform can have any suitable shape, length, height, diameter, or width, where such structural characteristics of the implantable platform can also be configured to affect or control a bioabsorption time profile.

When treating a sinus tissue, it can be advantageous for the implantable platform to have a rod-like shape with a length from about two time to about forty times greater than (2×-40×) its width and height. It can further be useful for the implantable platform to have a cross-sectional profile that is cylindrical, ovular, diamond, elliptical, triangular, square, rectangular, pentangular, hexangular, octangular, or ribbed. Generally, an implantable platform configured for a sinus tissue can have a length of about 0.5 cm to about 5 cm or longer and a width or diameter of about 0.21 mm to about 1.19 mm (i.e. widths that can fit within the inner diameter of 27G to 16G hypodermic needles).

When treating a throat tissue, it can be further advantageous for the implantable platform to have a cross-sectional profile that is cylindrical, ovular, diamond, elliptical, triangular, square, rectangular, pentangular, hexangular, octangular, or ribbed, or to have a distal end that is at least partially tapered. For throat tissues, it can also be advantageous for the implantable platform to have a biodegradation duration of about up to about 6 months. Generally, an implantable platform configured for the throat tissue can have a length of about 0.5 cm to about 2 cm or longer and a width or diameter of about 0.21 mm to about 1.19 mm.

When treating the Eustachian tube or ear canal, it can be further advantageous for the implantable platform to have a shape that is cylindrical, conical, or tapered. It can further be useful for the implantable platform to have a cross-sectional profile that is cylindrical, ovular, diamond, elliptical, triangular, square, rectangular, pentangular, hexangular, octangular, or ribbed. For the Eustachian tube or ear canal, it can also be advantageous for the implantable platform to have a biodegradation duration of about up to about 6 months.

Generally, an implantable platform configured for the Eustachian tube can have a length of about 0.5 cm to about 2 cm or longer and a width or diameter of about 0.21 mm to about 1.19 mm.

In some implementations, the implantable platform can be structured to have longitudinal channels running down the length of the platform.

Figure 1B:
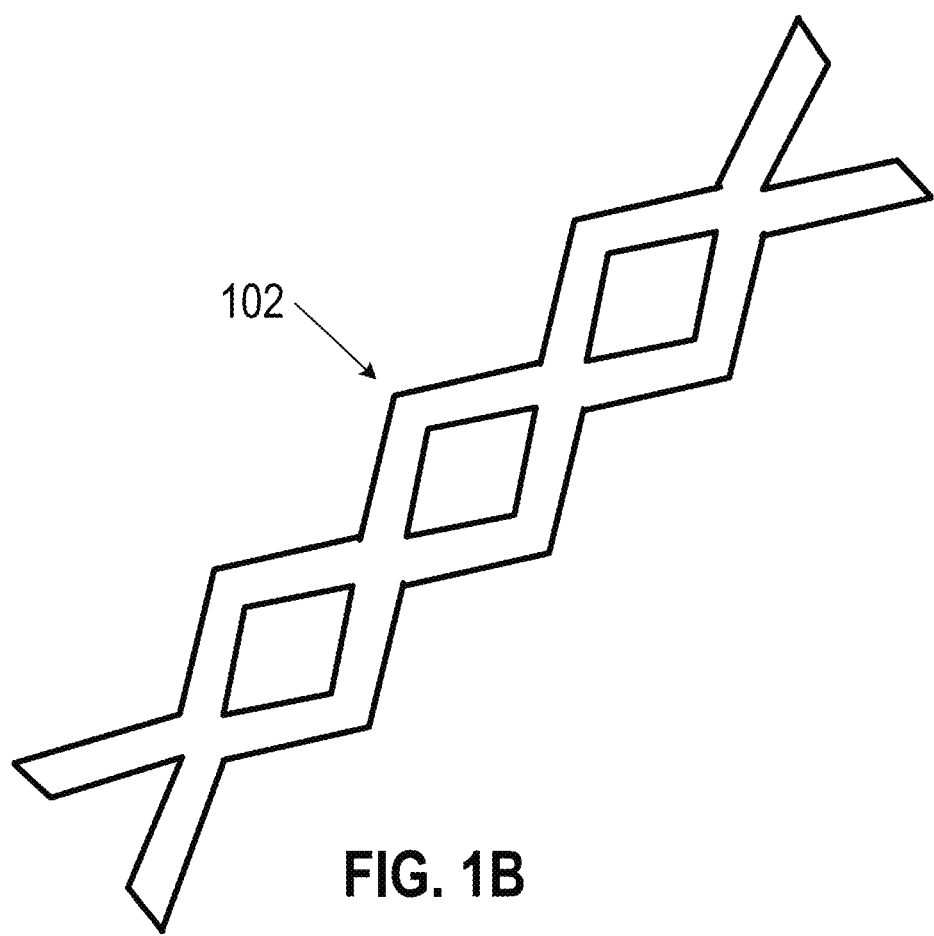
Figure 1C:
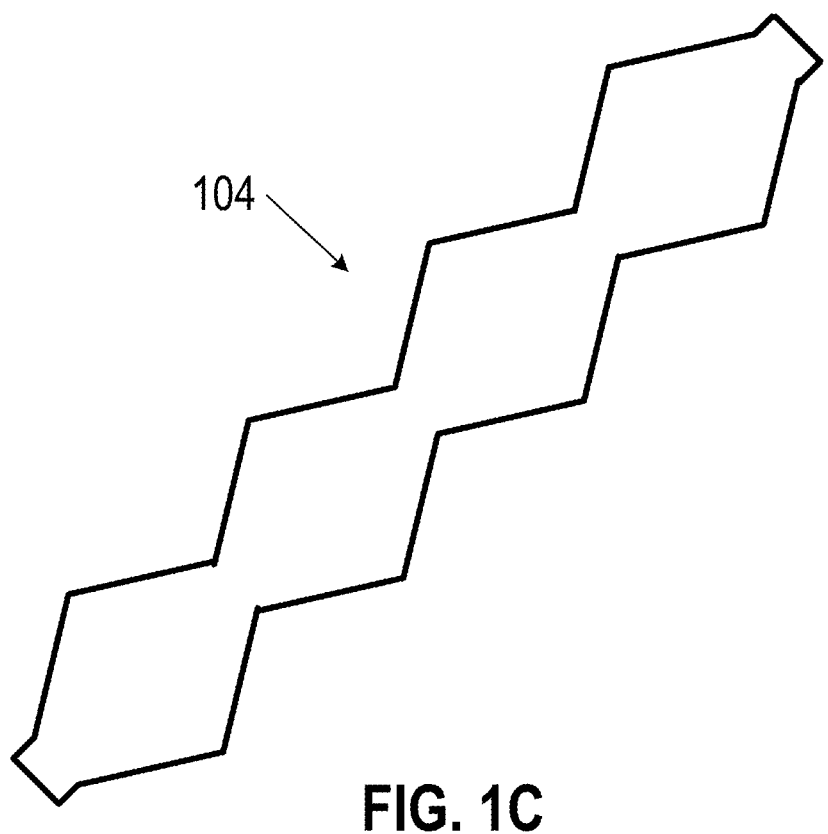
Figure 1D:
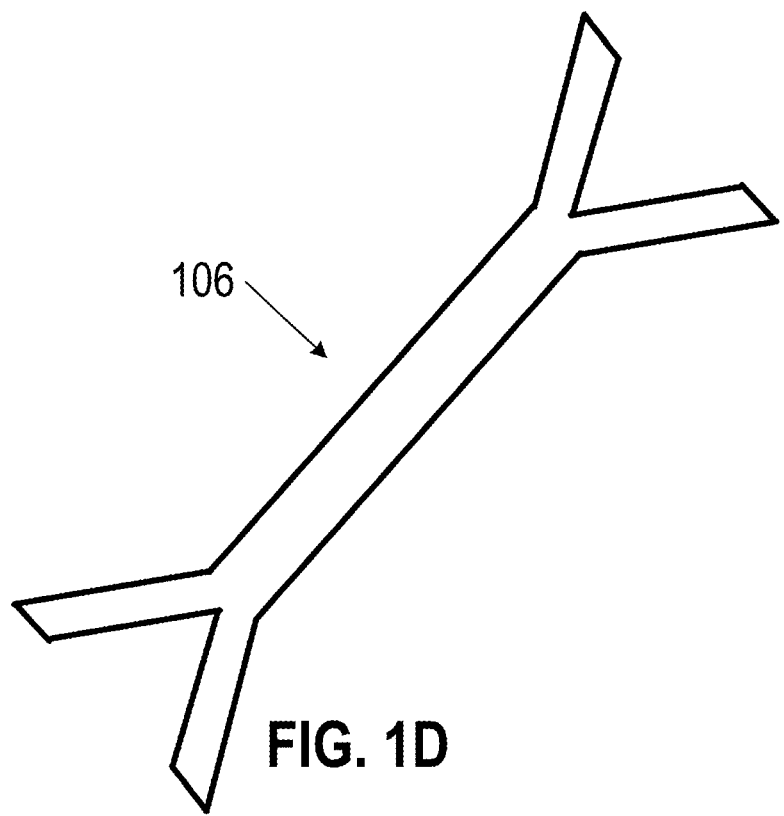

FIG. 1A depicts an illustration of an exemplary implantable drug delivery platform 100 having a generally cylindrical shape. FIG. 1B depicts an illustration of an exemplary implantable drug delivery platform 102 having repeating diamond shape. FIG. 1C depicts an illustration of an exemplary implantable drug delivery platform 104 having shape with an undulating width or varying diameter. FIG. 1D depicts an illustration of an exemplary implantable drug delivery platform 106 having a structure with a straight middle region and split, Y-shaped ends on both sides of the platform. Each of the drug delivery platforms shown herein can have a generally smooth surface or a surface that is at least partially rough or contoured surface. While the specific embodiment of FIG. 1A is described in further detail below, it should be understood that the characteristics and composition of this example is equally applicable to all embodiments of the drug delivery platform.

In some embodiments, the drug delivery platforms can be formed with a degree of curvature, or to have a spring force such that once implanted the platforms restore to a shape having a degree of curvature. The spring force of such a drug delivery platform can provide for tension and contact with surrounding tissue that aids in preventing dislodging of the platform post-implantation.

The loading of the drug into the platform is relatively high in order to achieve a relatively more efficacious dose across the relatively small surface area of the implant. In some embodiments, once loaded with the therapeutic agent, the drug accounts for about 40%-60% of the total mass of the drug delivery platform. In a specific embodiment, the drug accounts for about 50% of the total mass of the drug delivery platform.

The exemplary drug delivery platform 100 shown has a composition of 50% mometasone furoate as the drug and 50% poly(D,L-lactide-co-glycolide) (75:25) as the backbone. In an alternative embodiment, the composition can be 40% mometasone furoate and 60% poly(D,L-lactide-co-glycolide) (50:50) as the backbone. In a further embodiment, the composition can be 45% mometasone furoate and 55% poly(D,L-lactide-co-glycolide) (65:35) as the backbone. In another embodiment, the composition can be 35% mometasone furoate and 65% poly(D,L-lactide-co-glycolide) (75:25) as the backbone. It should be understood that further variations of the drug delivery platform can have ratios of drug to backbone ranging from 5% drug and 95% backbone, to 95% drug and 5% backbone, inclusive of incremental percentage ratios therein. It should also be understood that variations of the drug delivery platform using PLGA can have constituent ratios for the formulation of the (L:G) backbone ranging from (5:95) to (95:5).

Plasticizer or excipients can be added to the implant to reduce brittleness, to increase toughness, or both. Such plasticizers and excipients can include, but are not limited to, poly(ethylene glycol), glycerol, polysorbate, propylene glycol or combinations thereof.

The drug delivery platform 100 is a carrier for a therapeutic agent, where that therapeutic agent can be embedded within the drug delivery platform 100 and, when the drug delivery platform 100 is implanted within a target tissue, elute the therapeutic agent into the surrounding tissue. For example, a 0.3 mm diameter by 10 mm long implant, where the implant is about 50% mometasone furoate, can result in 450 µg of mometasone furoate eluted over a six-month time period to the local implanted tissue. In another example, a 0.36 mm diameter by 6 mm long implant, where the implant is about 50% mometasone furoate, can result in 500 µg of mometasone furoate eluted over a six-month time period to the local implanted tissue When implanted with in a target tissue site, the drug delivery platform 100 can provide for consistent and controlled local drug delivery in the surrounding tissue. Moreover, the local delivery of drug through this drug delivery platform 100 is advantageous in that the drug delivered by the platform does not spread systemically throughout the body of a patient. In other words, with controlled pharmacokinetics, the drug acts on the specific target tissue of interest, the drug remains in a relatively local area around the target tissue, and the drug does not lead to potential side effects or reduced dosage that can occur when spread systemically around a body.

The drug delivery platform can have a composition such that the therapeutic agent is released from the platform over a period of weeks to months to years. In some implementations, drug release in vivo from the implanted platform can be from about three months to about twelve months (3-12 mos.). The release time and profile can be tuned according to the drug loading profile and the target bioresorbable polymer degradation time. In terms of the composition of the drug delivery platform, exemplary materials that can be used include PLGAs and PDLLAs, where the molar ratio of the component structures in each material modify the release and resorption profile. For example, PLGA formed with a L:G molar ratio of 70:30 or 60:40 can be chosen as materials for a drug release duration in the range of from 3-12 months. In another example, PLGA formed with a L:G molar ratio of 50:50 can be chosen as materials for a drug release duration in the range of from 1-3 months. In yet another example, PLGA formed with a L:G molar ratio of 40:60 or 30:70 can be chosen as materials for a drug release duration in the range of from 3-9 months. In further embodiments, a blending of different materials can be used to form the drug delivery platform. For example, a mixture of a PLGA and a PDLLA, or two forms for PLGA with different molar ratios of L:G, can be blended together to achieve a desired release and resorption profiles.

The size, length, and shape of a drug delivery platform can be designed for specific anatomies and applications. The length of a drug delivery platform can vary based on the different tissues where the platform can be implanted, for example, a longer platform can be used for insertion into an inferior turbinate as compared to a relatively shorter platform used for insertions into a middle or superior turbinate. Shorter lengths may be utilized for pediatric patients. The shape of a drug delivery platform (for example as illustrated below in FIGS. 3A-3J and FIGS. 4A-4C) can be selected for penetrating or fitting into specific anatomy. The shape of a drug delivery platform can also be selected for the orientation of the surfaces of the platform to provide for a degree of control to the direction in which the released therapeutic agent elutes.

In some variations, the implantation device for the drug delivery platform can be delivered by a physician using a single hand.

Drug Composition

The formulation of the therapeutic agent in the drug delivery platform of the present disclosure can be any one of corticosteroids (e.g. mometasone furoate, fluticasone propionate, etc.), anti-histamines (azelastine, diphenhydramine azelastine, diphenhydramine), cytostatics (e.g. sirolimus, everolimus, zotarolimus, etc.), cytotoxic (e.g. pactlitaxel), or a combination thereof. In a particular embodiment, the therapeutic agent is mometasone furoate, or a pharmaceutically acceptable variation thereof.

The drug can be loaded or embedded within the implant by hot melt extrusion or melt compounding, solvent casting, emulsion based, spray drying, spray coating, injection molding, thermoforming, etc. In the case of hot melt extrusion, using PLGA as the backbone material, the PLGA may be first milled (e.g. via physical grinding, cryomilling, etc.) to a micro-particle size similar to that of the drug particles. Then the drug and PLGA may be dry mixed and melt compounded together and extruded and cut to form strands, rods, pellets, or other extruded shapes.

The implant may contain approximately 40-60% by mass drug with the remainder being polymer excipient. For example, the implant may contain also 60-40% by mass PLGA. Drug content may be uniform throughout the implant. Alternatively, the implant can be fabricated with drug distributed in a gradient manner for a higher concentration of drug near the surface versus core to enable an initial higher release of drug following implantation.

A drug coating topcoat or polymer topcoat may be further compounded or spray coated to add additional drug release control to the implant. A drug coating topcoat would provide for an initial higher release of drug. A polymer topcoat would enable less initial release and potentially extend the drug release over longer times.

The drug release profile from a drug delivery platform may follow a first order release profile, with an initial higher dosage release over a relatively short period of time followed by sustained lower dosage release over a longer period of time. The resulting tissue pharmacokinetics would demonstrate long term therapeutic drug exposure from three to twelve months (3-12 mos.). In the case where the drug delivery platform includes a polymer topcoat or is formed from a backbone with a longer resorbing duration (e.g., due to having a tuned PLGA ratio), the implant may demonstrate a longer sustained release and drug release kinetics that have a generally zero order profile.

In some cases to provide more immediate relief from nasal congestion, an anti-histamine such as azelastine may be combined with a corticosteroid such as mometasone furoate for a dual drug releasing implant system. For some cases in order to stop benign tissue growth of the ear, nose or throat a cytotoxic drug such as paclitaxel may be utilized.

Directional control of drug delivery may be controlled by end-capping the implant in order to achieve primarily a radial drug release. The ends may also be made relatively more porous to encourage a faster drug release profile through faster water absorption. A gradient of drug loading may be also achieved by multiple feed compounding.

In some variations, excipients having a molecular weight of 1000 g/mol or less may be beneficial in enhancing drug uptake through mucosal tissue. Exemplary mucoadhesive excipients include without limitation, carbomers, glyceryl monooleate, hypromellose, oleic acid, polycarbophil, polyethylene oxide, poly(ethylene glycol), and sodium alginate. Other mucoadhesives could obtain their adhesive properties by wetting of a soluble coating or polymer, charge adhesion (e.g., of anionic polymers such as polyacrylic acid, cellulosics, chitosan, gellan, carbopol, etc.), and covalent adhesion with e.g., a protein reactive gel such as PEG-NETS (poly(ethylene glycol)-N-hydroxylsuccinimide). In one variation, the mucoadhesive is poly(ethylene glycol). Exemplary penetration enhancers include, but are not limited to, dimethyl sulfoxide, glyceryl monooleate, glycofurol, isopropyl myristate, isopropyl palmitate, lanolin, mineral oil, linoleic acid, menthol, myristic acid, myristyl alcohol, oleic acid, oleyl alcohol, palmitic acid, polyoxyethylene alkyl ethers, polyoxylglycerides, pyrrolidone, sodium lauryl sulfate, thymol, tricaprylin, triolein, and combinations and mixtures thereof.

Additionally or alternatively, the therapeutic agent may be a lipophilic drug. In these variations, because the drug delivery platform is implanted proximate to and in contact with the tissue at the treatment site, the lipophilic nature of the drug(s) contained in the drug delivery platform promote elution out of the platform and transfer to and absorption by the tissue. Moisture within the tissue may facilitate this transfer. Other factors that may affect drug transfer from the platform include the amount of contact pressure exerted by the tissue on the implanted platform and the surface area of the drug delivery platform.

The drug or active agent of the drug delivery platform can include any suitable drug or agent, depending on the desired use thereof. The drug or active agent may comprise at least one of a diagnostic agent or a therapeutic agent, for example. Suitable classes of drugs include, for example, local anesthetics, painkillers (particularly non-opioid painkillers), vasoconstrictors, antiseptics, antioxidants, anti-inflammatory agents, anti-allergens, anti-cholinergic agents, antihistamines, anti-infectives, anti-platelet agents, anti-coagulants, anti-thrombotic agents, anti-scarring agents, antiproliferative agents, chemotherapeutic agents, antineoplastic agents, decongestants, healing promoting agents and vitamins (for example, retinoic acid, vitamin A, depaxapanthenol, vitamin B and their derivatives), hypersomolar agents, immunomodulators, immunosuppressive agents, mucolytics, and combinations and mixtures thereof.

In some implementations, when the site to be treated includes mucosal or mucociliary tissue, it may be useful for the drug layer to include excipients such as a penetration enhancer, a mucoadhesive and/or a mucolytic to enhance drug delivery across the mucus layer or to clear the mucus layer. Such an excipient can ensure a target dosage of drug delivery in cases where an implant is not positioned by a physician precisely as prescribed to achieve a complete implantation. Examples of mucolytic agents that can be used in these applications include carbocysteine, erdosteine, acetylcysteine, bromheksin, expigen syrup (sorbimacrogol laurate 300 and ammonium chloride), guaifenesin, glyceryl guaicolate, iodinated glycerol, or combinations or mixtures thereof.

Examples of antioxidants include tocopherol (vitamin E), alpha tocopherol, ascorbic acid, ascorbyl palmitate, butylated hydroxyanisole, butylated hydroxytoluene, citric acid monohydrate, erythorbic acid, ethyl oleate, fumaric acid, malic acid, methionine, monothioglyceraol, phosphoric acid, potassium metabisulfite, proprionic acid, propyl gallate, sodium ascorbate, sodium thiosulfate, sulfur dioxide, citric acid monohydrate, tartaric acid, and thymol.

Examples of local anesthetics include ropivicaine, mepivicaine, cocaine, procaine, lidocaine, hydrocodone, oxycodone, fentanyl, and morphine. Examples of vasoconstrictors include epinephrine, levonordefrin, afrin, and adrenaline. Examples of non-opioid painkillers include ibuprofen, acetaminophen, bupivacaine, aspirin, and naproxen.

Anti-infective agents generally include antibacterial agents, antifungal agents, antiparasitic agents, antiviral agents, antiseptics, iodine (e.g., povidone-iodine), potassium sorbate, sorbic acid, thimersol, thymol, butylene glycol, coconut oil, and vanillin. Anti-inflammatory agents generally include steroidal and nonsteroidal anti-inflammatory agents.

Examples of anti-allergic agents that may suitable for use with the described methods and devices include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, sirolimus, everolimus, temsirolimus, actinomycin D, actinomycin IV, actinomycin I1, actinomycin X1, actinomycin C1, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof. Examples of pro-healing agents include, but are not limited to, vitamin A.

Examples of cytostatic or antiproliferative agents that may be suitable for uses with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents (antibiotics) that may be suitable for use with the described methods and devices include, but are not limited to, aminoglycosides, amphenicols, ansamycins, betalactams, β-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In one variation, the antibacterial agent comprises ciprofloxacin. In another variation, the antibacterial agent comprises amoxicillin.

Examples of antifungal agents suitable for use with the described methods and devices include, but are not limited to, allylamines, imidazoles, polyenes, thiocarbamates, triazoles, and any of their derivatives. Antiparasitic agents that may be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl) guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents, for example, silver chloride, silver oxide, and silver nanoparticles.

Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof. In some variations, a corticosteroid is used in the sinuses and other bodily structures described herein to prevent or reduce inflammation post-surgery. The corticosteroid will generally be one with high potency, high binding to glucocorticoid receptors, and low bioavailability. For example, in some variations the corticosteroid comprises mometasone furoate, or a pharmaceutically acceptable salt, solvate, hydrate, ester, free base, enantiomer, racemate, polymorph, amorphous, or crystal form thereof. In other variations, the corticosteroid comprises dexamethasone, or a pharmaceutically acceptable salt, solvate, hydrate, ester, free base, enantiomer, racemate, polymorph, amorphous, or crystal form thereof.

Examples of suitable nonsteroidal anti-inflammatory agents include, but are not limited to, COX inhibitors. These COX inhibitors may include COX-1 or COX nonspecific inhibitors such as, for example, salicylic acid and derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that may be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in "Science" Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, paclitaxel, taxotere, azathioprine, docetaxel analogs/congeners, derivatives of such compounds, and combinations thereof.

Examples of decongestants that may be used in the devices and methods described here include, but are not limited to, epinephrine, pseudoephedrine, oxymetazoline, phenylephrine, tetrahydrozolidine, and xylometazoline. Examples of mucolytics that may be used in the devices and methods described here include, but are not limited to, acetylcysteine, dornase alpha, and guaifenesin. Anti-histamines such as azelastine, diphenhydramine, and loratidine may also be used in the systems and methods described herein.

Suitable hyperosmolar agents that may be used in the devices described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; zotarolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; botulinum toxin and other neurotoxins; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino(TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

The selection of drug type, drug form (e.g., crystal or amorphous), timing of delivery, and drug dose may be determined by the intended treatment plan, and may be further fine-tuned to meet the specific needs of an individual patient. Components of the drug delivery platform and the loading of the therapeutic agent into the drug delivery platform can be altered to adjust the release rates of the drug and/or the transfer rate of the drug to tissue.

The type of transfer desired may be obtained by altering the structure of the drug delivery platform, altering components of the drug formulation and/or their amounts therein, and/or altering various steps of the drug delivery platform manufacturing process. For example, when linear or zero order drug transfer is desired, the drug may be provided with a non-drug polymer topcoat. In alternative embodiments, a primer coating without drug can be incorporated between each drug layer. In other instances, a first order type release is desired, and drug compounded with polymer backbone and/or drug compounded in the top coating may be utilized.

The dose of drug (e.g., mometasone furoate) delivered when the drug is delivered may range from about ten micrograms to about ten milligrams (10 μg-10 mg) depending on size of the implant and drug loading. For example, a drug implant that is 50% loaded with drug and which is 0.3 mm in diameter and ten millimeters (10 mm) in length may contain a drug dosage of four hundred fifty micrograms (450 μg), or 0.64 mg/mm$^3$, that elutes out over six (6) months in a sustained manner in vivo. In another example, a drug implant that is 0.2 mm in diameter and 10 mm in length may contain a drug dosage of four hundred micrograms (400 μg) that elutes out over four (4) months in vivo. Of course, a treatment procedure may use more than one implant, increasing the overall dose of drug delivered to a target tissue or localized set of tissues in a patient.

The therapeutic agent carried by the drug delivery platform can include any suitable number or combination of drugs and excipients, depending on the condition to be treated, desired rate of drug release and coating transfer, etc. The drug delivery platform can include one, two, three, four, or five drugs, or more than five drugs. When two drugs are included in the drug delivery platform formulation, they can be mometasone furoate and an antihistamine, or mometasone furoate and an antibacterial agent. Likewise, the drug delivery platform may include one, two, three, four, or five excipients, or more than five excipients. When the tissue to be treated includes mucociliary tissue, it may be beneficial for the drug layer to include one or more penetration enhancing, mucoadhesive, or mucolytic excipients. For example, the drug delivery platform can include mometasone furoate as the drug, polysorbate as the penetration enhancer, polyacrylic acid as the mucoadhesive, and acetylcysteine as the mucolytic. The drug delivery platform may comprise a drug to excipient ratio ranging from about 3:1 to about 1:3.

The implantation of the drug delivery platforms being local to the target tissue, with a configured pharmacokinetic profile, allows for a controlled release of drug limited to the target area. This further reduces the dependency on patient compliance taking nasal steroid sprays or taking oral steroids. Moreover, the focused local delivery is advantageous over nasal sprays which may have their drug washed out before penetrating mucosal tissues. This again improves upon the safety, avoiding systemic effects of steroids on a patient.

In one variation, the drug delivery platform formulation includes a corticosteroid and a mucoadhesive excipient. In another variation, the drug delivery platform formulation includes a corticosteroid and a mucolytic excipient. In yet a further variation, the drug delivery platform formulation includes a corticosteroid and a penetration enhancer as the excipient. The drug delivery platform formulation may also include a corticosteroid, a mucoadhesive excipient, and a mucolytic excipient; or a corticosteroid, a mucoadhesive excipient, a mucolytic excipient, and a penetration enhancer. The corticosteroid in the aforementioned drug delivery platform may be mometasone furoate. Other drug delivery platform formulations may include an antibacterial agent in combination with one or more of a mucoadhesive excipient, a mucolytic excipient, and a penetration enhancer. In some instances, the mucolytic may be the active drug instead of the excipient in the drug delivery platform.

In some variations, the drug delivery platform for treating a nasal condition includes an antibacterial as the active agent, e.g., amoxicillin, and polysorbate as the excipient. In other variations, the coating for treating a nasal condition includes an antibacterial as the active agent, e.g., amoxicillin, and poly(vinyl pyrrolidone) as the excipient. In yet further variations, the coating for treating a nasal condition comprises an antibacterial as the active agent, e.g., amoxicillin, and poly(ethylene glycol) as the excipient. Alternatively, the coating for treating nasal conditions may include an antibacterial as the active agent, e.g., amoxicillin, and a combination of polysorbate, poly(vinyl pyrrolidone), and poly(ethylene glycol) as excipients.

Where the nasal condition involves treating the inferior turbinate, a shorter length delivery platform (e.g., <5 cm) may be useful to treat the anterior edge of the turbinate, while a medium length delivery platform may be useful to treat the posterior of the inferior turbinate (e.g., 7-8 cm). For treating the turbinates, a slight angled approach may be built into the distal end of the delivery system, where the angle may from about five degrees to forty-five degrees (5°-45°) in order to avoid delivery of an implant into or against bony tissues in the anatomy. For example, a delivery needle having a distal end bent to have a ten degree (10°) angle may facilitate more precise implantation of a drug delivery platform to the target turbinate tissues. When the nasal condition involves treating the middle turbinate, a relatively longer delivery platform having a length of greater than eight centimeters (>8 cm) in length or more may be useful. When the nasal condition involves treating the nasal septum or other appropriate tissue site, a tissue pinching delivery device may be utilized for optimal implant penetration depth. Other nasal tissue sites may include olfactory tissue, sinus ostia and/or cavities.

Where the nasal condition is damage or reduced function to the external nasal nerve, the drug delivery platform may include a growth factor as the therapeutic agent. In such applications, the drug delivery platform can be implanted proximate to the external nasal nerve, where a growth factor carried by the platform can elute locally and stimulate growth and/or healing of the external nasal nerve, thereby restoring a degree of olfactory function. Growth factors considered for treating sensorineural hearing loss include, but are not limited to, insulin-like growth factors, hepatocyte growth factors, fibroblast growth factors, and the like.

Where the nasal condition is epistaxis, the drug delivery platform can be implanted proximate to a target tissue site within a patient nose, where the bleeding source is most frequent. In such applications, the drug delivery platform may include a vasoconstrictor and/or hemostatic as the therapeutic agent.

When an otic condition is to be treated, the drug delivery platform formulation may include an antibacterial agent, an anti-inflammatory agent, e.g., a corticosteroid such as dexamethasone, or combinations thereof, in addition to an excipient or combination of excipients. For example, the antibacterial agent may include ciprofloxacin or amoxicillin, and the excipient may comprise a polysorbate, poly(vinyl pyrrolidone), or poly(ethylene glycol). In one variation, the drug delivery platform formulation comprises ciprofloxacin as the antibacterial, and polysorbate as the excipient. In another variation, the drug delivery platform formulation comprises ciprofloxacin as the antibacterial, and poly(vinyl pyrrolidone) as the excipient. In yet further variations, the drug layer formulation comprises ciprofloxacin as the antibacterial agent, and poly(ethylene glycol) as the excipient. In some instances, it may useful for the drug layer formulation to include ciprofloxacin and polysorbate, poly(vinyl pryrrolidone), and poly(ethylene glycol) as excipients.

Where the otic condition is sensorineural hearing loss, the drug delivery platform may include a growth factor as the therapeutic agent. In such applications, the drug delivery platform can be implanted proximate to the cochlea, where a growth factor carried by the platform can elute locally and stimulate growth and/or healing of the cochlea, thereby restoring a degree of hearing. Growth factors considered for treating sensorineural hearing loss include, but are not limited to, insulin-like growth factors, hepatocyte growth factors, fibroblast growth factors, and the like.

Where the otic condition is Meniere's disease, the drug delivery platform can include therapeutic agents including, but not limited to, ciprofloxacin, meclizine, diazepam, dexamethasone, mometasone furoate, fluticasone propionate, glycopyrrolate, lorazepam, or the like. In such applications, the drug delivery platform can be implanted proximate to the inner ear, where the therapeutic agent carried by the platform can elute locally.

When a throat condition is to be treated, the drug delivery platform formulation may include as the active agent, a painkiller, an anesthetic, an anti-inflammatory agent (e.g., a corticosteroid), an antibiotic, or combinations thereof. More specifically, where the throat condition is tonsillitis, the drug delivery platform may include therapeutics including, but not limited to, nonsteroidal anti-inflammatories, analgesics, penicillin, and the like. Where the throat condition is vocal polyps, the drug delivery platform may include therapeutics including, but not limited to, prednisone, bethamethasone, prednisolone, triamcinolone, methylprednisolone, mometasone furoate, fluticasone propionate, or the like.

Implantation/Delivery Device

The drug delivery platform described here may be delivered using any suitable injection or implantation device (alternatively referred to as an "applicator"). The implantation device can be configured to deliver the drug delivery platform as a minimally invasive procedure. The drug delivery platform can be loaded into the implantation device, deployed from the implantation device at the target tissue treatment site of a subject, and then left within target tissue while the implantation device is removed from the subject.

Figure 2A:
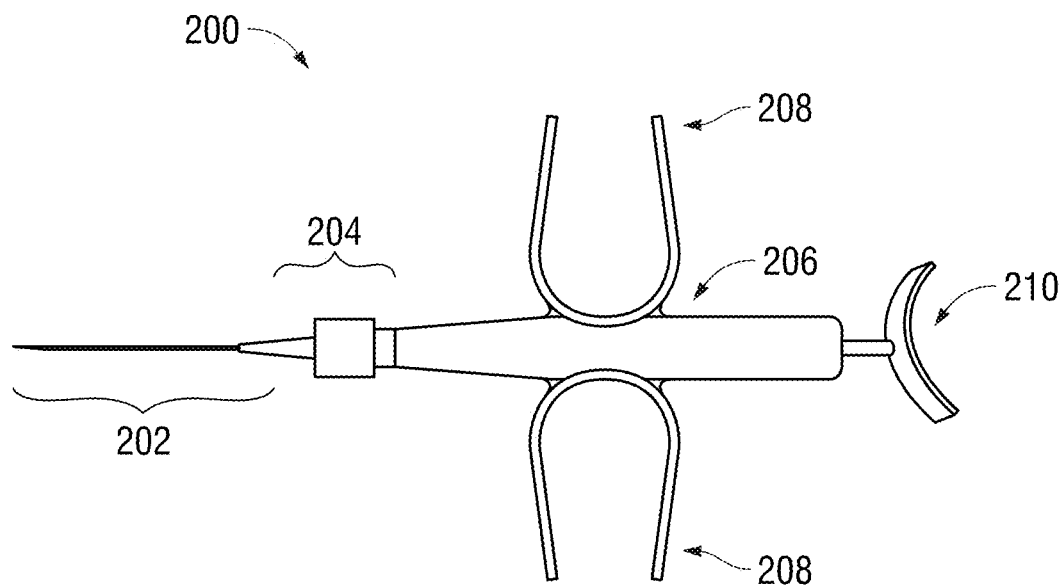
FIGS. 2A and 2B depict images of exemplary implantation devices for injecting or implanting a drug delivery platform, according to aspects of the present disclosure.

FIG. 2A depicts an image of an exemplary implantation device 200 for injecting or implanting a drug delivery platform. The implantation device 200 has a distal end from which a drug delivery platform is injected into a target tissue site, and a proximal end from which a user can hold and operate the implantation device 200. The distal end of the implantation device 200 primarily includes a hypodermic needle 202 in which a drug delivery platform can be loaded. The hypodermic needle 202 can have a gauge and shape that can accommodate the size and shape of a corresponding drug delivery platform. In some embodiments, the hypodermic needle 202 can have a length of from about five millimeters to about one hundred millimeters (5 mm-100 mm) or increments of length in that range. For example, in specific implementations the hypodermic needle 202 can have a length of about ten millimeters (10 mm), about fifteen millimeters (15 mm), or about twenty millimeters (20 mm). In some embodiments, the hypodermic needle 202 can have a gauge (G) and inner diameter, or gradients of said gauges and inner diameters, that is large enough to accommodate the width or diameter of a drug delivery platform, where the hypodermic needle 202 can be, for example (but without limitation), a 20G needle, a 21G needle, a 22G needle, a 22sG needle, a 23G needle, a 24G needle, a 25G needle, a 26G needle, a 26sG needle, a 27G needle, a 28G needle, a 29G needle, or a 30G needle.

The implantation device 200 has a connector 204 that couples the hypodermic needle 202 to the shaft 206 which constitutes the main body of the implantation device 200. In some aspects, one or more drug delivery platforms can be stored with in the shaft 206 of the implantation device 200, arranged to be moved into and through the hypodermic needle 202. The one or more drug delivery platforms can be stored directly within the shaft 206 or within a cartridge loaded into the shaft 206. Two curved anchors 208 are arranged on opposing sides of the shaft 206, providing a location for user to place their fingers. A plunger 210 having a curved base is provided at the proximal end of the implantation device 200, where the plunger 210 fits into the shaft 206, and as the plunger is driven into the shaft 206 (in the distal direction), a drug delivery platform loaded into the hypodermic needle 202 will be pushed outward from the implantation device 200. The distal end of the plunger (not shown) can be shaped to match with or accommodate the shape of the drug delivery platform, to ensure engagement and a smooth stroke when the drug delivery platform is driven out of the implantation device 200 as the plunger 210 is depressed. The implantation device 200 and the various components of the implantation device 200 can be formed from appropriate materials, including but not limited to plastics, metals, ceramics, of a combination thereof.

Figure 2B:
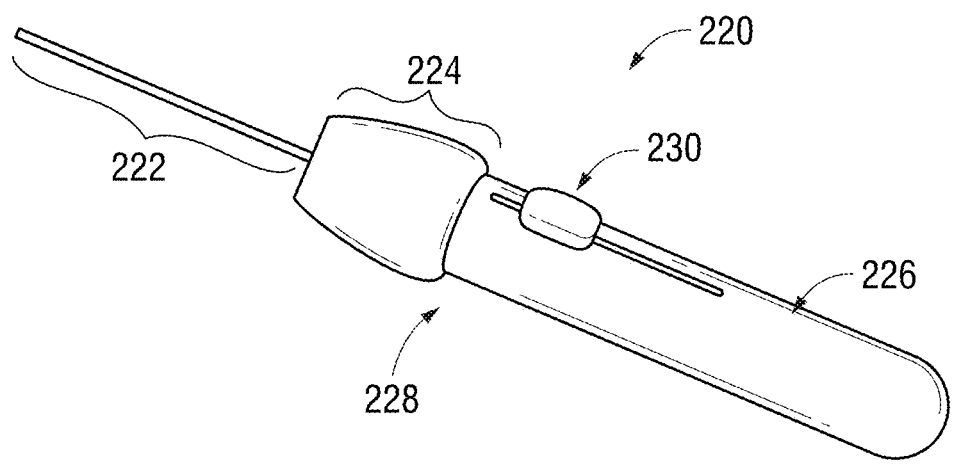

FIG. 2B depicts an image of an alternative exemplary implantation device 220 for injecting or implanting a drug delivery platform. The implantation device 220 has a distal end from which a drug delivery platform is injected into a target tissue site, and a proximal end from which a user can hold and operate the implantation device 220. The distal end of the implantation device 220 primarily includes: a hypodermic needle 222 in which a drug delivery platform can be loaded, a rotatable connector 224 that couples the hypodermic needle 222 to the shaft 226 which constitutes the main body of the implantation device 220. In some aspects, one or more drug delivery platforms can be stored with in the shaft 226 of the implantation device 220, arranged to be moved into and through the hypodermic needle 222. The rotatable connector 224 can have an indicator aligning with an implant counter 228 imprinted on the surface of the shaft 226. The rotatable connector 224 can be adjusted manually or automatically along with each injection of a drug delivery platform, tracking the implant counter 228 so as to keep track of the number of drug delivery platforms that have been ejected (or have yet to be ejected) from the implantation device 220 by a visible signal or count. A driver 230 (alternatively referred to as a slider) can be arranged on the surface of the implantation device 220, arranged to move a long a longitudinal slot in the shaft 226, such that moving the driver from the proximal end to the distal end of the implantation device 220 ejects a drug delivery platform. In some aspects, progressive movement of the driver 230 can lead to ejection of individual drug delivery platforms, while in other aspects ejection of individual drug delivery platforms can follow a cycle of moving the driver in the distal direction and then back to a proximal starting point for a subsequent drug delivery platform.

In some aspects, the one or more drug delivery platforms can be stored directly within the shaft of a delivery device, or within a cartridge loaded into or onto the delivery device or within the delivery system package. In other aspects, the mechanical actuation system for ejecting a drug delivery platform can be a button-based system, a spring-injected system or other spring-loaded system. Such a system can allow for a user to preload a platform implant and inject it without pushing the implant directly via a traditional finger-actuated depressor or plunger. In some variations, individual drug delivery platforms can be released and ejected from the device in a sequential order into a target tissue tract.

For embodiments of the drug delivery platforms that are formed with a degree of curvature, the hypodermic needles of the implantation devices can have a corresponding curvature at their distal end. In some implementations, the distal end of a hypodermic needle can have a curvature of around 10° for a length about equal to the length of a corresponding drug delivery platform. This curvature can allow for the platform to be implanted into tissue close to the relaxed position of the platform.

Figure 2C:
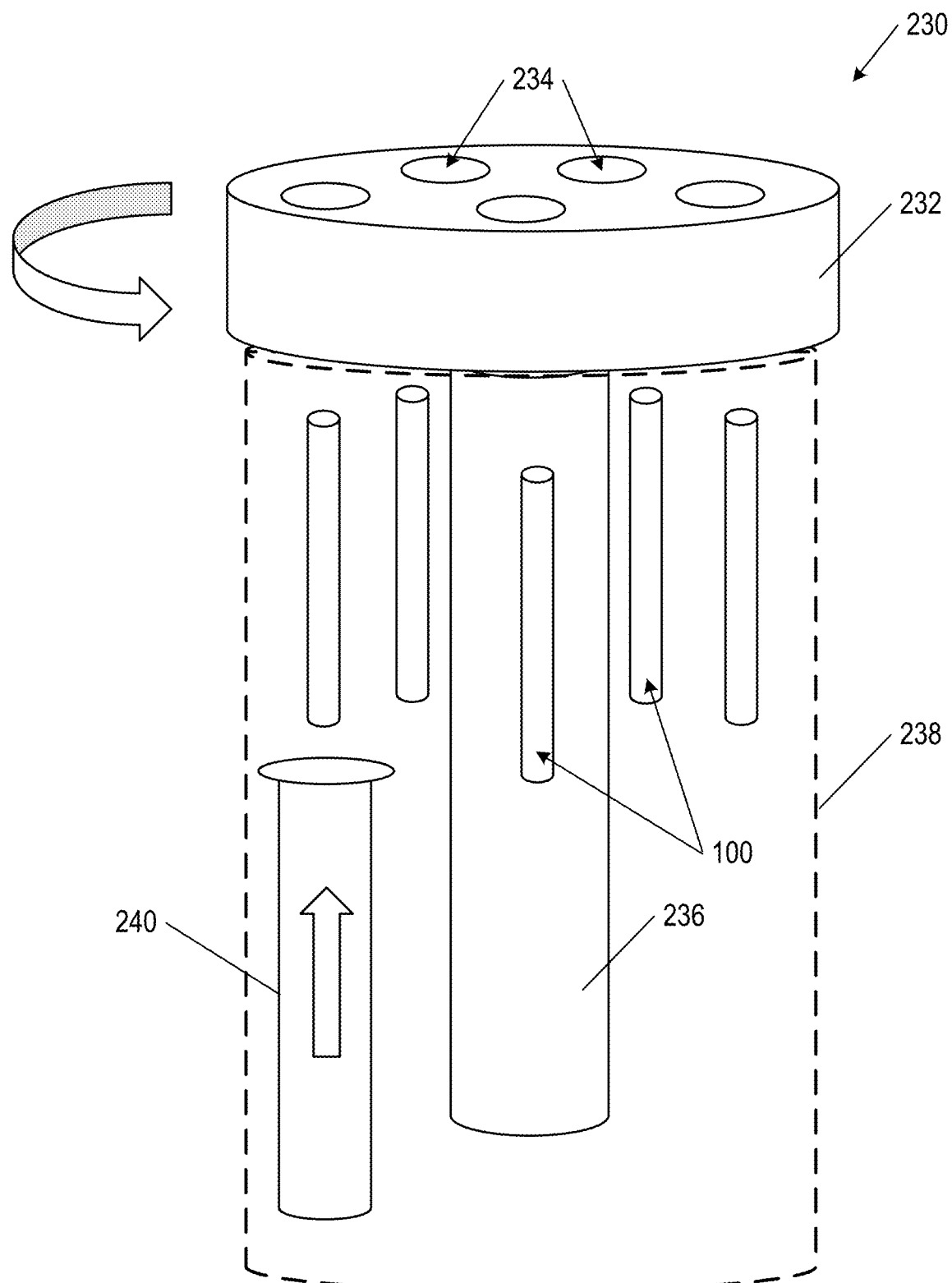

FIG. 2C depicts a schematic illustration of a multi-implant revolver loading structure 230 for an implantation device as described herein. The revolver loading structure 230 is incorporated with the structure of the implantation device and can be an affixed or a removable/swappable module of the implantation device. The revolver loading structure 230 includes a cylinder 232 having apertures 234 through which a respective drug delivery platform (shown here as a plurality of exemplary implantable drug delivery platforms 100 from FIG. 1A) can pass, and a shaft 236. The shaft 236 and the drug delivery platforms 100 are within a housing 238, were the drug delivery platforms 100 are mounted inside the housing 238. The drug delivery platforms 100 can be mounted to the shaft 236, to the cylinder 232, or to both, and each of the plurality of drug delivery platforms 100 can be mounted in alignment with a respective aperture 234 in the cylinder 232. The drug delivery platforms 100 may be mounted using a structure such as a belt conveyor or a carousel, where the drug delivery platforms 100 are coupled to the conveyor or carousel securely enough to move or shuttle along with rotation, but loosely enough to readily detach when engaged on their proximal end by the driving member 240. In the embodiment as shown, the plurality of drug delivery platforms mounted within a revolver loading structure 230 can be five (5), and in alternative embodiments the plurality of drug delivery platforms mounted within a revolver loading structure 230 can range from two (2) to twelve (12). The cylinder 232 and shaft 236 can be rotated (e.g. in the direction of the exemplary arrow shown) such that one of the plurality of the drug delivery platforms 100 are aligned with a driving member 240 (alternatively referred to as a "plunger"). The driving member 240 can be similarly aligned with a hypodermic needle (positioned distally of the revolver loading structure 230) such that when the driving member 240 is actuated (e.g. translated in a distal direction along the longitudinal axis of the implantation device), the driving member 240 pushes one of the plurality of the drug delivery platforms 100 through a respective aperture 234 of the cylinder 232 and into hypodermic needle. The driving member 240 can be mechanically coupled to a different module of the implantation device that is operable by a user, allowing the driving member 240 to be actuated.

FIG. 2D depicts a schematic illustration of a multi-implant magazine loading structure 242 for an implantation device as described herein. The magazine loading structure 242 is incorporated with the structure of the implantation device and can be an affixed or a removable/swappable module of the implantation device. The magazine loading structure 242 includes a casing 244 within which a plurality of drug delivery platforms can be loaded (shown here as a plurality of exemplary implantable drug delivery platforms 100 from FIG. 1A), a rack 246 on which the plurality of drug delivery platforms 100 are mounted, and a ring 248 arranged to align with one drug delivery platform 100 as the rack 246 moves past a proximal side of the ring 248. In the embodiment as shown, the plurality of drug delivery platforms mounted within a magazine loading structure 242 can be six (6), and in alternative embodiments the plurality of drug delivery platforms mounted within a magazine loading structure 242 can range from two (2) to twelve (12). As shown, a spring 250 can optionally be positioned within the casing 244 and arranged to apply a force driving the rack 246 in a direction such that the plurality of drug delivery platforms 100 are sequentially moved into alignment with the ring 248. The spring 250 exerts force on the rack 246 and not directly on any individual drug delivery platform 100, thereby avoiding unintentional breakage of implants while loaded within the magazine loading structure 242. Alternatively, movement of the rack 246 and any drug delivery platforms 100 mounted thereon can be done by manual translation with mechanical means by a user of the implantation device. The rack 246 can translated in a direction such that one of the plurality of the drug delivery platforms 100 are aligned with a driving member 240. The driving member 240 can be similarly aligned with a hypodermic needle (positioned distally of the magazine loading structure 242) such that when the driving member 240 is actuated (e.g. translated in a distal direction along the longitudinal axis of the implantation device), the driving member 240 pushes one of the plurality of the drug delivery platforms 100 through the opening of the ring 248 and into hypodermic needle. The driving member 240 can be mechanically coupled to a different module of the implantation device that is operable by a user, allowing the driving member 240 to be actuated.

In another embodiment, using drug delivery platforms with sufficient internal structural strength, the drug delivery platforms can be stacked directly on each other without a rack structure, and the spring can push directly on the array of stacked drug delivery platforms to advance or shuffle the platforms into an insertion position. In such a tight-loading configuration, the individual drug delivery platforms may be glued together with a moderate adhesive that will hold the platforms together when mounted in the magazine loading structure, but will not prevent a driving member from shearing off an individual platform when performing an implantation.

For at least both the revolver loading structure 230 and the magazine loading structure 242, the draw length of the driving member 240 can be shortened to make the implantation procedure easier. One approach to shorten the draw length of the driving member 240 is to use a mechanical linkage between the driving member and the portion of the implantation device that a user exerts force on to increase the throw length of the driving member 240 by a 2:1 ratio or greater. Another approach to increase the efficiency of implant loaded is to use a corkscrew loader within the handle of the implantation device, such that actuating the driving member functions to implant a platform and concurrently or sequentially loads the next platform into the necessary position for the next implantation. Further, to indicate to a user that an implant has been ejected from the revolver loading structure 230 or the magazine loading structure 242, haptic indicators (e.g., a notch or bump along the internal path of the driving member 240) and/or visual indicators (e.g., a counter on the respective structure or on the implantation device) can be used for confirmation of implantation.

Comparing the loading structures of FIG. 2C and FIG. 2D, different advantages may be had from the contrasting structures. For example, the apertures 234 in the revolver loading structure 230 can be constructed independent of implant length, allowing for a wider range of implant diameters that may be used. In contrast, for a magazine loading structure 242, the size and diameter of the implant will guide the tolerances and internal structure of the magazine loading structure 242, but such a tight-loading configuration can allow a relatively more compact form factor for the magazine loading structure 242. Both of the loading structures of FIG. 2C and FIG. 2D provide the advantage of being removable and interchangable from the underlying delivery device, which allows for greater efficiency and ease in manufacturing, sterilization, and clinical use. For example, in a sinus application, a single delivery device can be provided to a physician with two multi-implant revolver loading structures 230 (or two magazine loading structures 242 for a corresponding delivery device). Each of the two loading structures can have a full complement of drug delivery platforms to be implanted for one side of the sinuses, effectively making a left-side and a right-side implant cartridge, allowing a physician to control dosage on each side of the sinuses simply by the available number of implants in a cartridge.

Figure 2E:
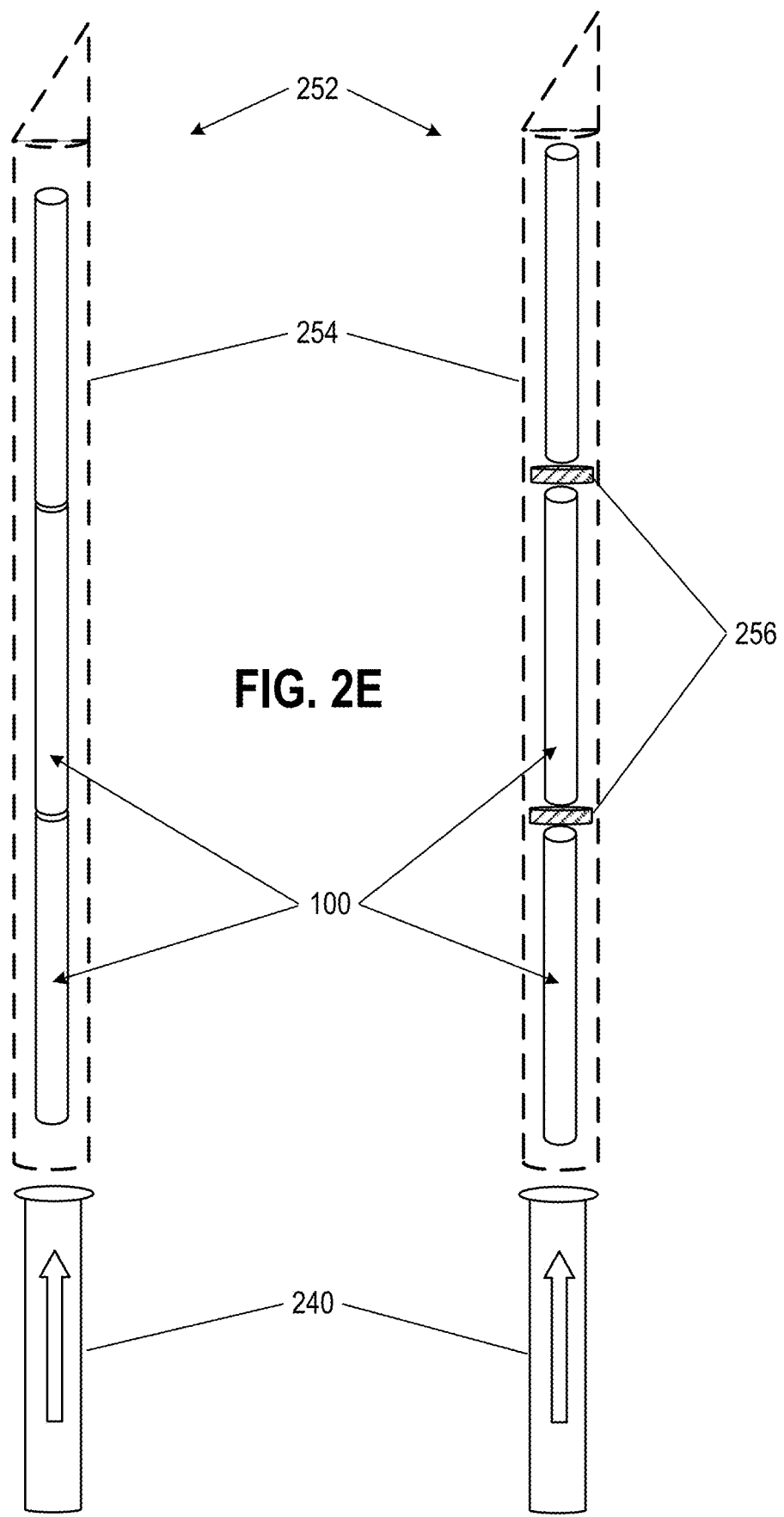

FIG. 2E depicts a schematic illustration of two multi-implant loaded needle structures 252 for an implantation device as described herein. Here, a plurality of drug delivery platforms (shown here as a plurality of exemplary implantable drug delivery platforms 100 from FIG. 1A) can be loaded in-line with a hypodermic needle 254 of the implantation device, facilitating a single-point delivery from the delivery device. Accordingly, a driving member 240 positioned proximally of a hypodermic needle 254 can be actuated (e.g. translated in a distal direction along the longitudinal axis of the implantation device) to directly push the plurality of drug delivery platforms 100 through the hypodermic needle 254. The internal diameter (ID) of the hypodermic needle 254 and the outer diameter (OD) of the drug delivery platforms 100 can be matched such that, while being advanced by the driving member 240, the ID surface of the hypodermic needle 254 provides sufficient support to the drug delivery platforms 100 to avoid breakage of the implants within the hypodermic needle 254 even when loaded back-to-back in series. As illustrated, the right-hand side embodiment of the needle structures 252 further includes buffer elements 256 positioned between each of the plurality of drug delivery platforms 100 within the hypodermic needle 254. The loaded needle structures 252 can be connected to the distal end of the implantation device and can be an affixed or a removable/swappable module of the implantation device. Further, to indicate to a user that an implant has been ejected from the loaded needle structure 252, haptic indicators (e.g., a notch or bump along the internal path of the driving member 240) and/or visual indicators (e.g., colored markings indicating the position of the driving member 240 on the exterior of the implantation device) can be used for confirmation of implantation.

The buffer elements 256 can reduce the risk of breakage of the drug delivery platforms 100 as they reside in and are pushed through the hypodermic needle 254. The buffer elements 256 can be made of gels, aerogels, water-soluble gels, biodegradable materials, or other materials that are generally biologically neutral and non-toxic. Alternatively, the buffer elements 256 can be made of a material that is not configured to be implanted, a stronger material than gels that is not necessarily biodegradable. Rather, with such stronger buffer elements, the implantation procedure can include a draw-back step, such as a half-crank in the proximal direction, following implantation of a drug delivery platform such that while the platform is inserted into tissue, the draw-back pulls the buffer material away from the tissue. Thus, a buffer can be ejected and removed from the tissue region before the subsequent platform implantation.

In alternative embodiments, a compound design can be used, combining the pre-loaded needle tip as shown in FIG. 2E with either of the multi-implant loading structures as shown in FIG. 2C or FIG. 2D. In such configurations, either the revolver or the magazine multi-implant loading structure is situated within the delivery device at a proximal location, and the loaded needle structure is at a distal location. The structures are aligned such that when an implant is pushed out from the proximal loading structure, it moves into the distal hypodermic needle, thereby pushing out an implant at the distal end of the needle, where that implant may be a pre-loaded implant or an implant previously moved into the needle from a prior shuttling of implants from the proximal loading structure.

Figure 2F:
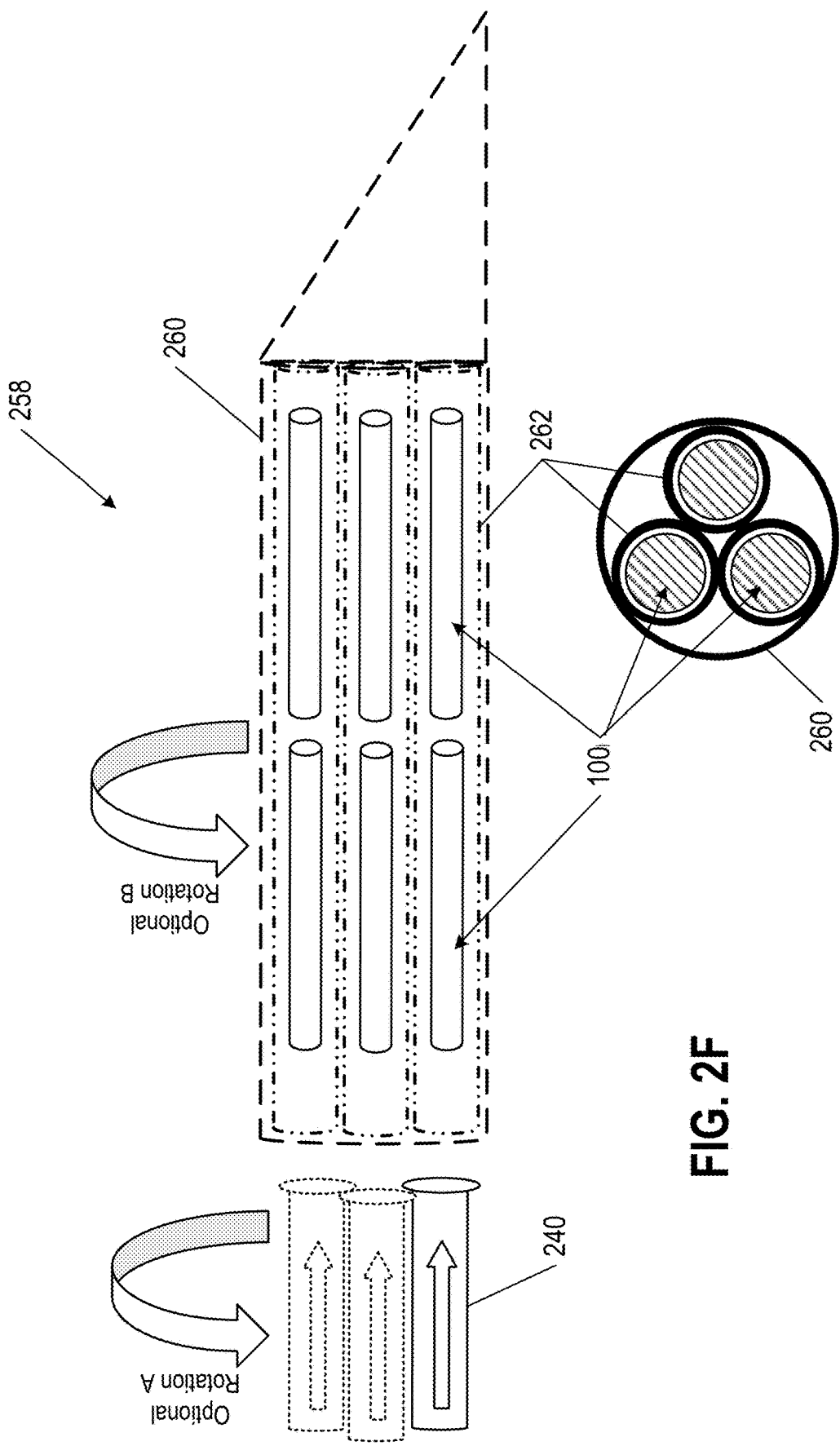

FIG. 2F depicts a schematic illustration (in profile and in cross-section) of a multi-implant lumen-loaded needle structure 258 for a multi-point implantation device as described herein. Here, lumen-loaded needle structure 258 includes has an outer needle shaft 260 with three lumens 262 positioned along the length of the lumen-loaded needle structure 258. Each of the three lumens 262 can have a series of drug delivery platforms 100 loaded in series therein. A driving member 240 is positioned proximally of the outer needle shaft 260 and can be actuated (e.g. translated in a distal direction along the longitudinal axis of the implantation device) to directly push into one of the lumens 262 and thereby push one or more of the plurality of drug delivery platforms 100 through the lumen-loaded needle structure 258. Following ejection of drug delivery platforms 100 from one or the lumens 262, a section of the lumen-loaded needle structure 258 can be rotated to realign the driving member 240 with a subsequent lumen 262. In one embodiment (labeled as Optional Rotation A), the driving member 240 can be rotated by a mechanical action to sequentially align with one of the lumens. In another embodiment (labeled as Optional Rotation B), the outer needle shaft 260 can be rotated by a mechanical action to sequentially align with the driving member 240. In a further alternative embodiment, the multi-point implantation device can have three driving members 240 aligned with each of the lumens 262, thereby allowing for concurrent implantation of three drug delivery platforms 100. In another alternative embodiment, there can be two lumens 262 housed within an outer needle shaft 260 and the driving member 240 can be orientated accordingly. With two or three lumens 262, the outer needle shaft 260 can have a diameter of less than five millimeters (<5 mm) which can be advantageous for physician handling of the device. In other embodiments, with a wider gauge hypodermic needle, more than three lumens loaded with drug delivery platforms can be arranged within the hypodermic needle.

It should be appreciated that distal end of the driving member 240, where the driving member 240 touches a drug delivery platform, can be beveled to control the movement and reduce the risk of jamming or breakage of the drug delivery platforms while being pushed through a hypodermic needle. Similarly, the tip of a hypodermic needle can be beveled to aid in the entry of implants into tissue without breakage or jamming of the drug delivery platforms as they pass out from the implantation device and into tissue.

Figure 3A:
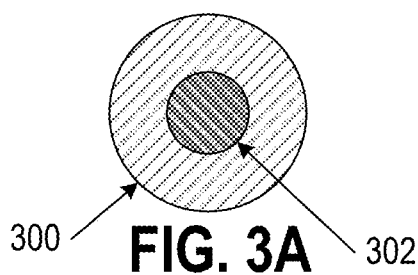
FIGS. 3A-3N depict illustrations of cross-sections of exemplary embodiments of an implantable drug delivery platform, according to aspects of the disclosure.
Figure 3B:
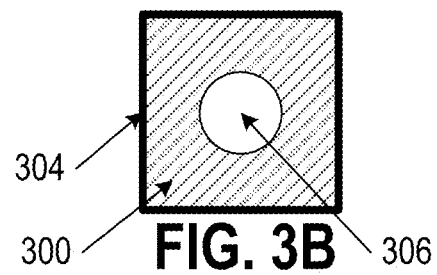
Figure 3C:
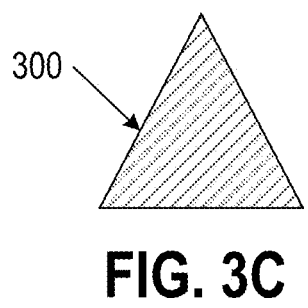
Figure 3D:
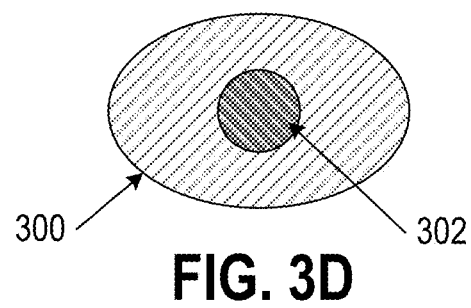
Figure 3E:
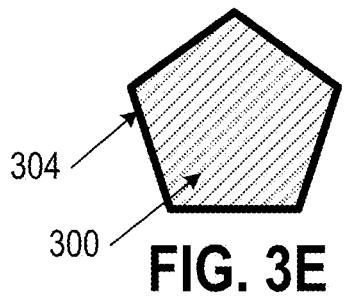
Figure 3F:
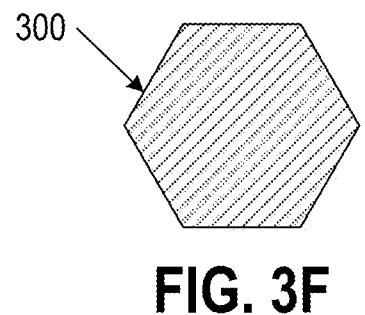
Figure 3G:
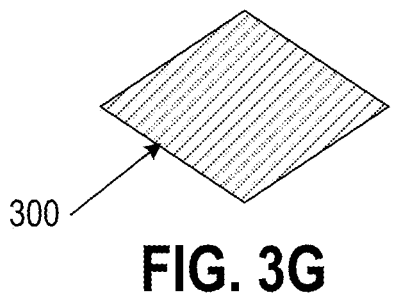
Figure 3H:
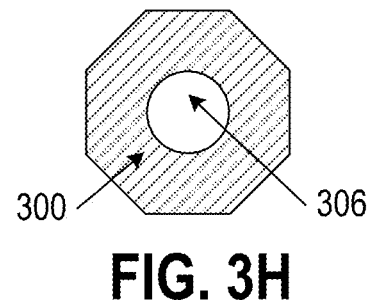
Figure 3I:
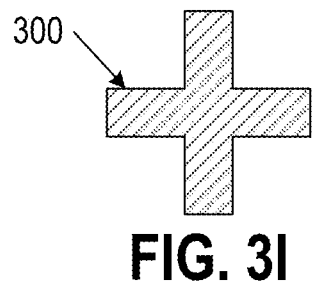
Figure 3J:
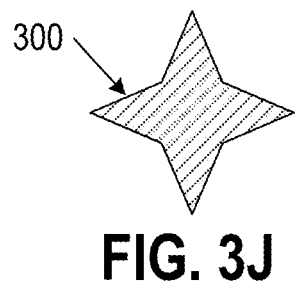

FIGS. 3A-3J depict illustrations of cross-sections of exemplary embodiments of an implantable drug delivery platform. Each illustrated embodiment has a main body 300 of the platform that is infused with the therapeutic agent. The various embodiments of the drug delivery platform are illustrated as follows: FIG. 3A shows the drug delivery platform having a circular cross section; FIG. 3B shows the drug delivery platform having a rectangular cross section, specifically shown here as having a square cross-section; FIG. 3C shows the drug delivery platform having a triangular cross section, shown here as equilateral but also inclusive of non-equilateral triangles; FIG. 3D shows the drug delivery platform having an elliptical cross section; FIG. 3E shows the drug delivery platform having a pentangular cross section; FIG. 3F shows the drug delivery platform having a hexagonal cross section; FIG. 3G shows the drug delivery platform having a diamond cross section, where the interior angles of the diamond shape can be adjusted to achieve a target height and width; FIG. 3H shows the drug delivery platform having an octagonal cross section; FIG. 3I shows the drug delivery platform having a cross-shaped cross section; and FIG. 3J shows the drug delivery platform having a 4-pointed star-shape cross section.

Figure 3K:
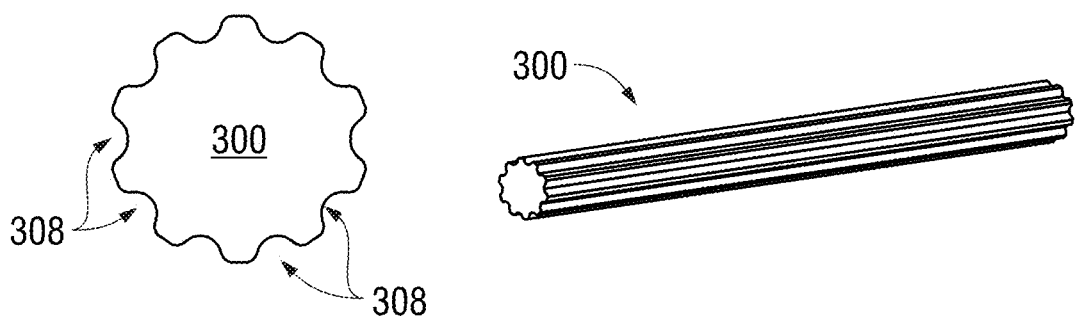
Figure 3L:
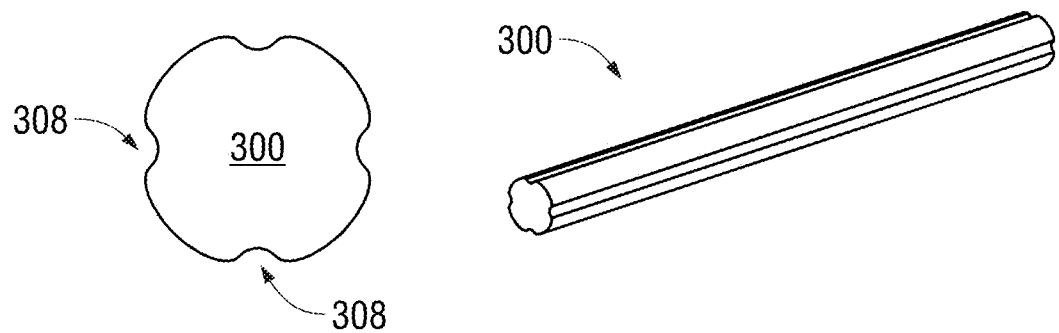
Figure 3M:
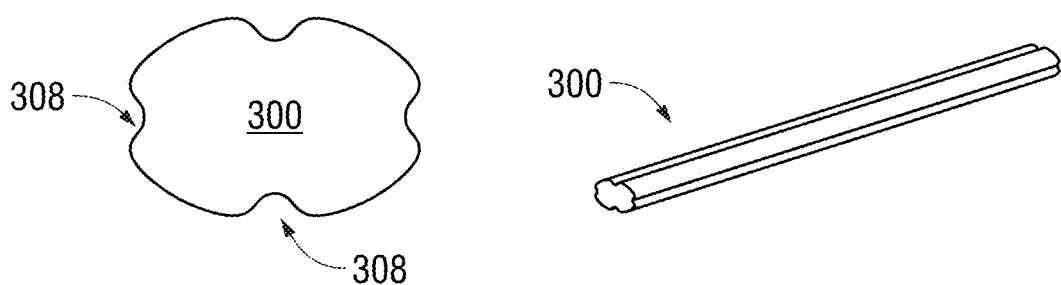
Figure 3N:
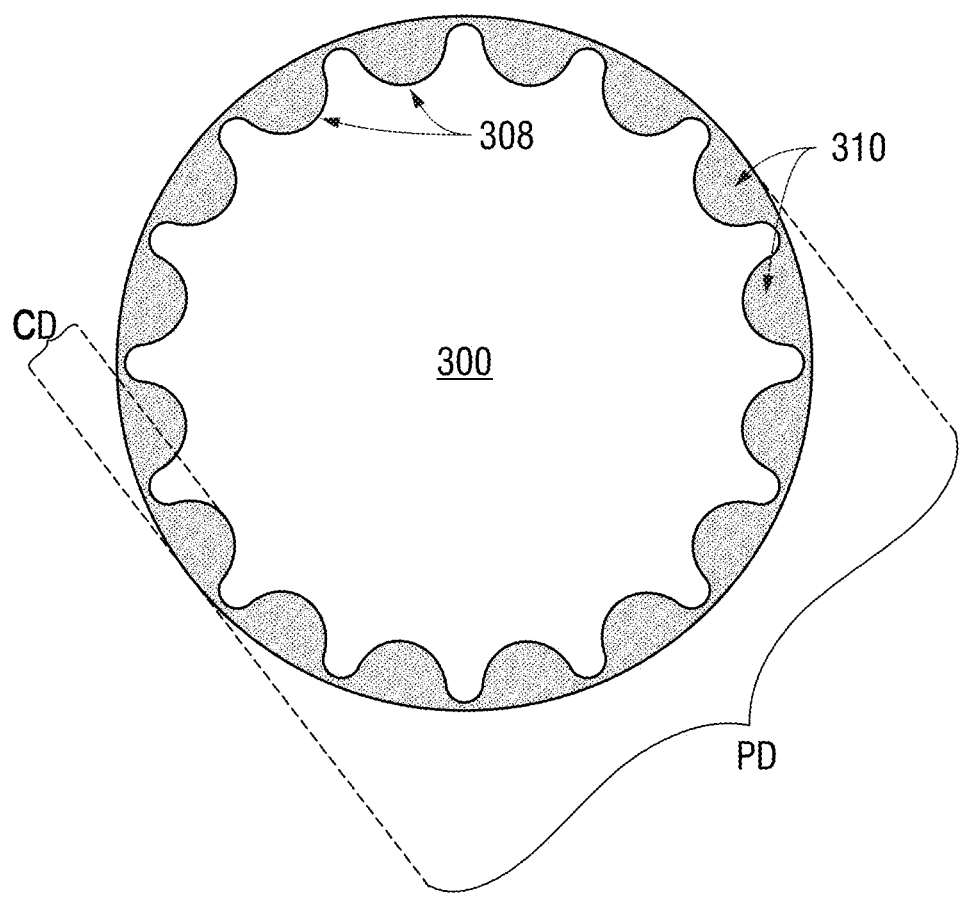

FIGS. 3K through 3M depict illustrations of cross-sectional and perspective views of further exemplary embodiments of an implantable drug delivery platform. Again, each illustrated embodiment has a main body 300 of the platform that is infused with the therapeutic agent. The various embodiments of these versions of the drug delivery platform further include longitudinal channels along the primary axis of the implant. Conversely, these structures may be considered to be longitudinal ridges along the main axis of the implant main body 300. FIG. 3K shows a pair of images (cross-sectional & perspective) of the drug delivery platform, having a generally circular cross-section with ten (10) channels. FIG. 3L shows a pair of images (cross-sectional & perspective) of the drug delivery platform having a generally circular cross-section with four (4) channels. FIG. 3M shows a pair of images (cross-sectional & perspective) of the drug delivery platform having a generally oval cross-section with four (4) channels. FIG. 3N shows the shows the drug delivery platform having a generally circular cross-section with sixteen (16) channels, and further having drug packed into those channels. It should be understood that versions of the drug delivery platforms as shown in FIGS. 3K through 3M can also have drug packed into those embodiments' respective channels, similar to the embodiment of FIG. 3N.

The primary non-drug component of the main body 300 is generally formed of PLGA, where the molar ratio of L:G in the PLGA can be from 100% lactide to 100% glycolide, or more specifically 10:90 to 90:10, or at balances of an L:G ratio within that range. For example, in specific implementations the molar ratio of L:G in the PLGA can be 5:95, 15:85, 20:80, 25:75, 30:70, 35:65, 40:60, 45:55, 50:50, 55:45, 60:40, 65:35, 70:30, 75:25, 80:20, 85:15, or 95:5. Variations for compositions of the main body can include PLGA formed at a molar ratio other than those listed above, can be achieved through additional control of material characteristics such as inherent viscosity ("IV" or $\eta_{inh}$). For example, two or more forms for PLGA with different molar ratios of L:G and/or inherent viscosities can be mixed together during the main body 300 manufacturing process. Inherent viscosities of a polymer material used herein can vary from 0.2 dL/g to 1.0 dL/g, where the material can be provided at increments or gradients of IV within this range. In some variations, the IV of a polymer material used herein can be greater than 1.0 dL/g. Another approach to forming variations of compositions of the main body can be through use of ester capped polymer end chains or acid capped polymer end chains, or combinations thereof, which can operate to control (i.e., slow or quicken) the rate of biodegradation. Various embodiments of the drug delivery platform can include any combination of one or more of the characteristics shown herein and the like.

In some embodiments, as illustrated in FIGS. 3A and 3D, the main body 300 further includes an optional core region 302. In some aspects, the core region 302 can be a formed of a different material than the main body 300. In other aspects, the core region 302 can be a formed of the same material than the main body 300 but at a different formulation. For example, in an implementation, both the main body 300 and the core region 302 can be both formed of PLGA, where the molar ratio of L:G in the PLGA can be from 10:90 to 90:10, including balances of an L:G ratio within that range, and is different than the molar ratio of L:G of the main body 300.

In other embodiments, as illustrated in FIGS. 3B and 3E, the main body 300 can be coated with an additional coating layer 304, where the coating layer can include the same or a different therapeutic agent as the main body 300. The coating layer 304 can additionally or alternatively include rate release modifiers (e.g., excipients) to increase or reduce the rate at which therapeutic agent is related from the drug delivery platform into the surrounding tissue.

In further embodiments, as illustrated in FIGS. 3B and 3H, the main body 300 can include a core region 306 (alternatively referred to as an "internal channel") that can be kept empty (hollow), can be filled with the same therapeutic agent as embedded within the main body 300 but in an alternate form (e.g., a drug in crystal, liquid, or gel form), or can be filled with a therapeutic agent different from the therapeutic agent embedded within the main body 300 (e.g., the channel region can contain a biologic treatment). In aspects where the core region 306 is hollow, implantable drug delivery platform can provide for an irrigation or drainage pathway through tissue or through an obstructed space (e.g., a passage blocked in part by inflamed tissue). In one exemplary implementation, an implantable drug delivery platform having such a core region 306 can provide for treatment of otitis media, being implanted in a region of the middle ear or proximate tissue and allowing for drainage and discharge of the symptomatic fluid. Similarly, the core region 306 can provide for a route through which medications can be delivered further into the ear canal (past swollen or inflamed tissues or blockages) to more directly treat the infection vector and/or deliver pain medications.

In some embodiments, as illustrated in FIGS. 3K through 3N, the main body 300 can include one or more channels 308 (alternatively referred to as "external channels", "long pockets", "grooves", or "surface channels") that extend along the primary (longitudinal) axis of the implant. The channels 308 can be formed in the main body 300 of the implant during extrusion of the implant, by using a mold that provide for the target cross-sectional shape. Alternatively, the channels 308 can be carved or etched (physically or chemically) into the main body 300 of an implant that is extruded with a generally smooth surface. In various implementations, the number of channels 308 that can be formed in the main body 300 of the implant can be from one (1) to sixteen (16), as illustrated herein. The channels 308 can be positioned symmetrically or asymmetrically around the perimeter of the implant. The channels 308 can be biased onto a specific region of the implant, for example, all of the channels 308 can be formed on one-half of the implant exterior while leaving the other side of the exterior smooth or uniform. There can be an odd or even number of channels 308 formed into the implant. In further variations, the one or more channels 308 can be formed such that they progress helically (twist) around the surface of the main body 300.

Channels 308 can be arranged in various patterns or arrays on the surface of the implant as a way of fine tuning the flexibility, increasing surface area for drug delivery, preventing migration of the implant within tissue, and/or aiding anchorage of the implant within tissue. The presence of channels 308 can add to the structural resilience of the main body 300 in that, as compared with an implant without surface etching, the channels 308 reduce the amount of material over the length of the main body 300, such that the implant still provides a similar bending performance as a circular cross section version of the implant, but has a greater flexibility and lower physical strain from one end of the main body 300 to the other when bent at least because there is a reduced amount of main body 300 structure that is bent. Further, the prevention of implant migration within tissue can be of particular importance when two or more implants are placed adjacent or in-line next to each other within the same tissue (e.g. when three implants deposited sequentially within the inferior turbinate by a single delivery device) so as to prevent physical overlap and to maintain a desired therapeutic effect.

In other embodiments, as illustrated in FIG. 3N, one or more of the channels 308 can be additionally packed or filled with the active therapeutic agent, referred to as "packed drug" 310. Here, in addition to the main body 300 being formed both of a polymer backbone (e.g., PLGA) incorporated with the active therapeutic agent (e.g., a drug such as moametasone furoate), the channels 308 are further filled with packed drug 310. Accordingly, with the additional drug primarily on the surface of the implant, a greater dosage of drug can be delivered to the target tissue site. As opposed to the coating of a drug-containing later onto the surface of an implant, the packed drug 310 can be retained within the channels 308 with less risk of sheering or frictional loss of drug during loading, transport, and implantation of the main body 300. Moreover, with the packed drug 310 being on the surface of the implant and not incorporated as part of the main body 300 of the implant, the implant can provide a two-phase drug delivery profile with the packed drug 310 releasing from the channels 308 first, followed by the release of drug from the main body 300 structure. Practically, the number of channels that can be formed into the exterior of the implant as well as the channel depth of such channels will be limited based on the overall width or diameter of the nasal, otic, and/or throat tissue implant.

In FIG. 3N, the channel depth ("CD") is shown in further detail as compared to the platform diameter ("PD"). In some aspects, each channel 308 can have the same channel depth into the main body of the main body 300 of the implant. In other aspects, the one or more channels 308 can have a different channel depth into the main body of the main body 300 of the implant. In various aspects, the channel depth of the one or more channels 308 in the implant shown in FIG. 3N can be from about 5% to about 15% of the platform diameter.

In some embodiments, the channels can have a tapered depth, providing for different implant stiffness from the proximal to the distal end. In another embodiment, different dosages of an active therapeutic agent or different amounts an active therapeutic agent of may be packed onto opposing sides or sections of an implant. The amount of packed drug on the exterior of an implant can also provide for a preferential stiffness or bending profile. In other embodiments, materials with different durometer can be packed into the channels of an implant, where such materials may but do not necessarily contain active therapeutic agent, which can also provide for a preferential stiffness or bending profile. In further embodiments, a free-floating material or an embedded material may be packed into the exterior channels of the implant, where the materials may but do not necessarily contain active therapeutic agent.

Generally, the channels for any given drug delivery platform as considered herein can have a channel depth that is about 5%, about 10%, about 15%, about 20%, or about 25% of the platform diameter, or a depth in between those percentage ranges. In a specific example, using a circular implant with a 0.76 mm platform diameter, the channel depth for all of the channels in the main body is 0.06 mm, such that an individual channel depth equates to about 8% of the platform diameter. Any one or more channels in a main body of an implant can have different depths. Further, the number of channels in the main body of an implant can affect the depth(s) of those channels, in order to ensure that the implant has a sufficient structural strength and/or flexibility.

In a further variation, a drug delivery platform can include one or more channels (which extends into the platform diameter of an implant main body) and one or more ridges (which extends beyond the platform diameter of an implant main body). In such variations, the channels and ridges can be positioned alternatingly, in opposition to each other, or biased in one section around the circumference or perimeter of the implant.

Figure 4A:
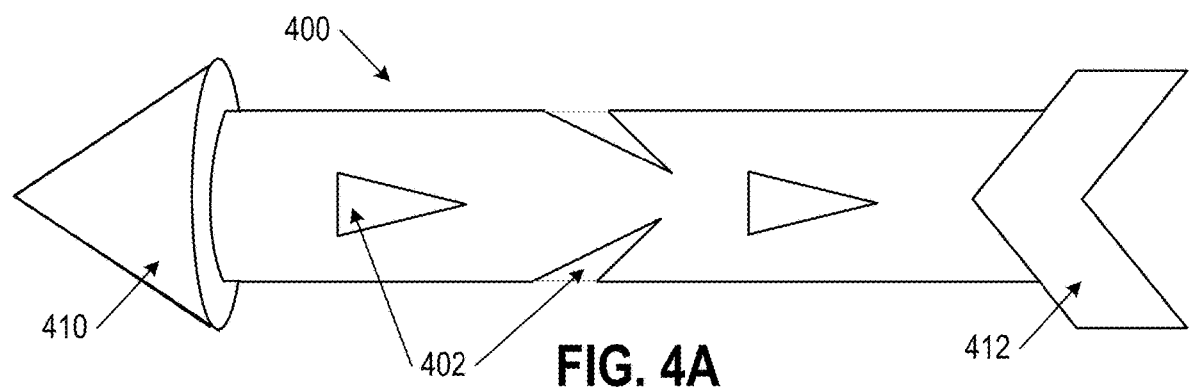
FIGS. 4A-4C depict illustrations of sections of exemplary embodiments of an implantable drug delivery platform, according to aspects of the disclosure.
Figure 4B:
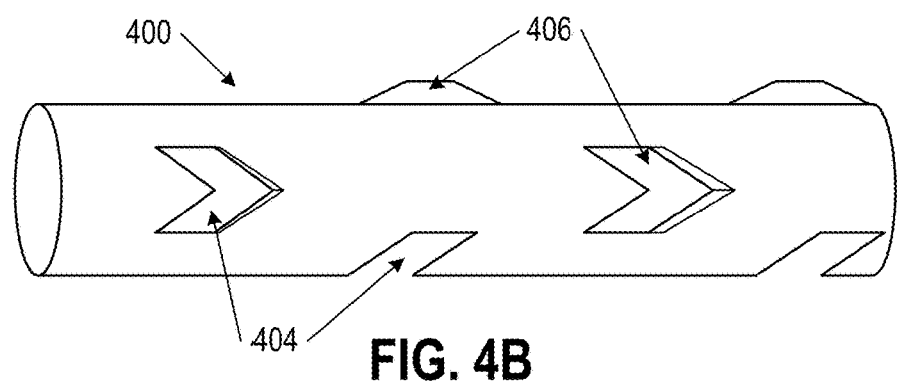
Figure 4C:
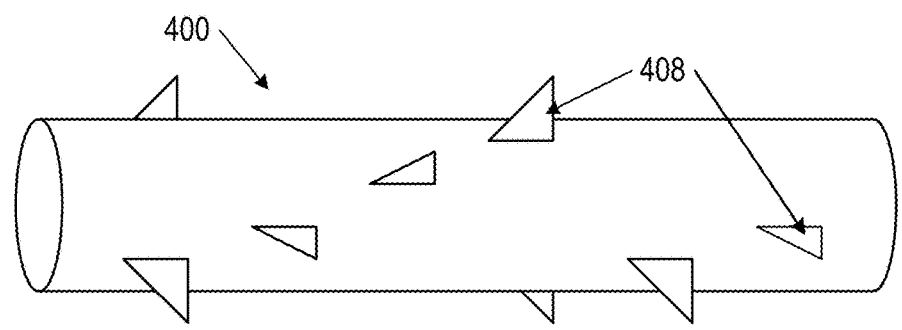

FIGS. 4A-4C depict illustrations of cross-sections of sections of exemplary embodiments of an implantable drug delivery platform. The embodiments of FIGS. 4A-4C further illustrate versions of the drug delivery platform having a contoured or textured surface, with structures including projections, depressions, barbs, anchors, and the like, arranged around the surface of the drug delivery platform. Such structures extending out of or into the main body of the drug delivery platform provide for contours and edges in the surface that can catch, hold, and/or anchor onto the tissue in which the drug delivery platform 400 is implanted, and thereby increase retention of the drug delivery platform 400 in the tissue.

The various contour structures that modify the surface area, either by extending into or away from the core of the drug delivery platform 400, can be angularly offset from the longitudinal axis of the drug delivery platform 400, where contour structures can have an angle of about 45°. In other aspects, the contour structures can have an angle in the range of from about 15° to about 75° offset from the longitudinal axis of the drug delivery platform or increments of angle within that range. The contour structures can be patterned around the surface area of the drug delivery platform 400 and can be linearly offset from each other on the drug delivery platform 400. Further, the contour structures can be spaced apart from each other along the length of the surface area of the drug delivery platform 400 by a distance of about one millimeter (1 mm) or about two millimeters (2 mm). In some aspects, the contour structures can be unidirectional as arranged on the drug delivery platform 400.

In FIG. 4A, drug delivery platform 400 includes depressions 402 which provide for contours and edges in the surface of the drug delivery platform 400. The depressions 402 in FIG. 4A are shown as triangular, but it is appreciated that the geometry of such depressions can have an alternative shape or include a combination of different shapes. In FIG. 4B, drug delivery platform 400 includes indentations 404 and ridges 406 which provide for contours and edges in the surface of the drug delivery platform 400. The indentations 404 and ridges 406 in FIG. 4B are shown as having a chevron-like shape, but it is appreciated that the geometry of such indentations and ridges can have alternative shapes or include a combination of different shapes. In FIG. 4C, drug delivery platform 400 includes projections 408 which provide for contours and edges in the surface of the drug delivery platform 400. The projections 408 in FIG. 4C are shown as triangular, but it is appreciated that the geometry of such projections can have an alternative shape or include a combination of different shapes.

FIG. 4A further illustrates a variation of the drug delivery platform 400 having an arrowhead 410 at the distal end adapted for penetration into tissue. FIG. 4A also further illustrates a variation of the drug delivery platform 400 having a tail 412 at the proximal end, having a Y-shape or arrow-shape, adapted for retention within tissue.

After the drug delivery platform is implanted within the target tissue, the implantation device is withdrawn from the target tissue site.

Methods

The drug delivery platforms described here may be delivered to target tissues of the nose, ear, or throat, and may be used for the treatment of conditions affecting those tissues. As previously described, in some variations, the drug delivery platforms may be delivered to a sinus cavity, sinus ostium, paranasal sinus, ethmoid sinus, inferior turbinate, middle turbinate, osteomeatal complex, nasal septum, nasal vestibule, and/or nasal cavity. The method may be for treating nasal conditions such as post-surgical inflammation, rhinosinusitis, and/or allergic rhinitis, for example. In other variations, the drug delivery platforms may be delivered to the Eustachian tube, external ear canal, and/or inner ear. The method may be for treating otic conditions such as post-surgical inflammation, otitis media, Meniere's disease, and/or tinnitus. In yet other variations, the drug delivery platforms may be delivered to the throat for the treatment of post-surgical pain, such as tonsillectomy pain, or for oncology (e.g., esophageal cancer), airway stenosis, chronic laryngitis, or epiglottitis. In further variations, the drug delivery platforms may be delivered to a region or section of skin to treat wounds or dermatological conditions. Drug delivery platforms may include a drug loading designed to locally deliver an active agent to the target tissue and provide sustained or extended release of the active agent at a therapeutic level for a desired period of time.

The methods described herein may include locally delivering a therapeutically effective amount of an active agent to a target tissue by insertion of a delivery device, deployment of a drug eluting implant, and retrieval of a delivery device.

Figure 5A:
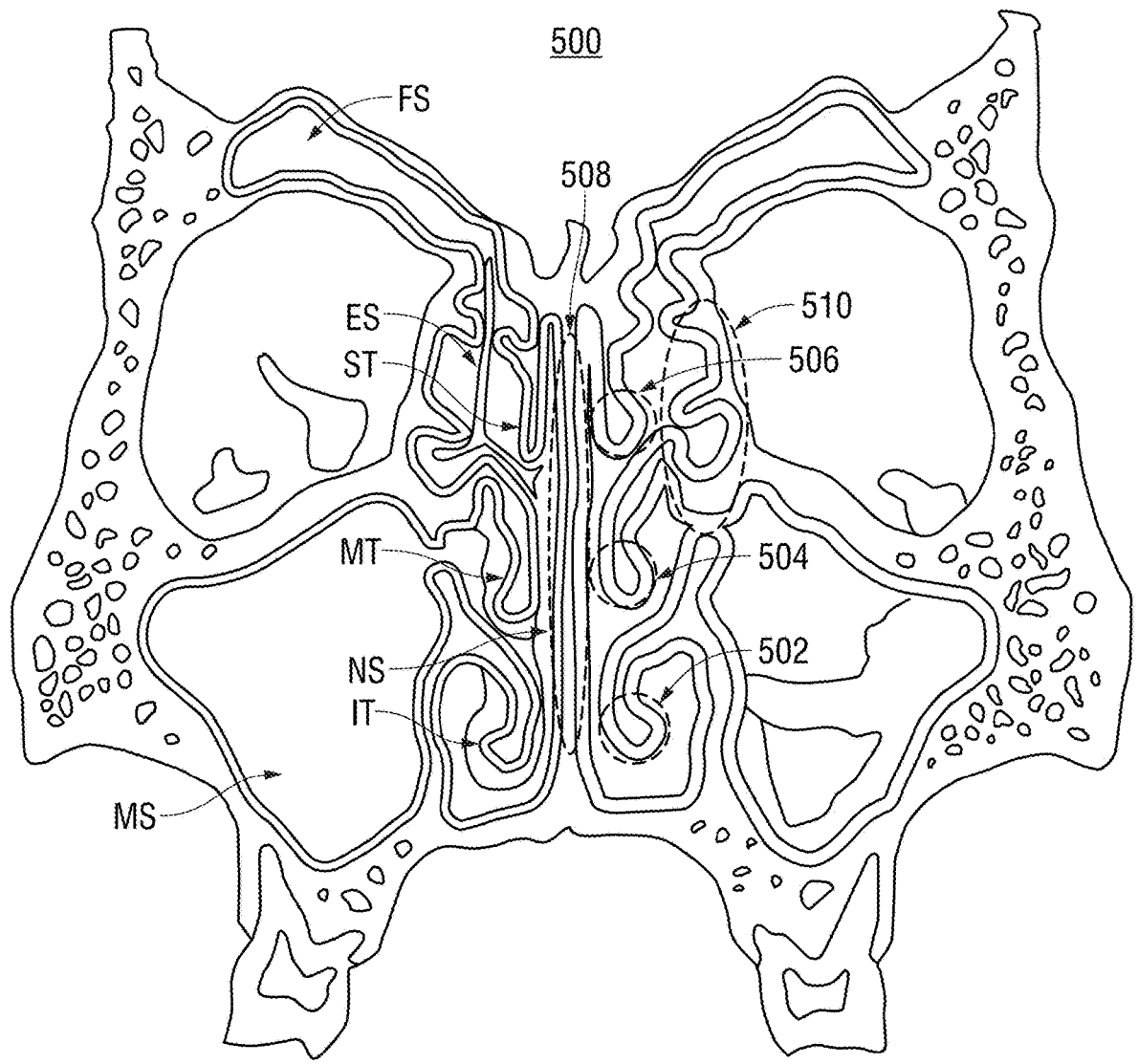
FIG. 5A is an illustration depicting sinus and implant locations for a method of delivering therapy with a drug delivery platform, according to aspects of the disclosure.

FIG. 5A is an illustration of sinus anatomy 500 depicting sinus and implant locations for a method of delivering therapy with a drug delivery platform. In FIG. 5A, the left-hand side of the image illustrates a healthy sinus anatomy and the right-hand side illustrates a diseased and/or inflamed sinus anatomy. Specific parts of the sinus anatomy are labeled on the left-hand side as follows: frontal sinus (FS), maxillary sinus (MS), ethmoid sinus (ES), nasal septum (NS), superior turbinate (ST), middle turbinate (MT), and inferior turbinate (IT). Potential locations are shown on the right-hand side of the image (using dashed lines). It should be understood that given the bilateral structure of the sinus anatomy, analogous structures on the right-hand side have the same name, and that the number of platforms that can be implanted within structures on both sides of the sinus anatomy are the same. Location 502 is within the inferior turbinate, which can generally be accessed via the nasal passage, in which one (1) to four (4) platforms can be implanted. Location 504 is within the middle turbinate, which can generally be reached via surgical access, in which one (1) to three (3) platforms can be implanted. Location 506 is within the superior turbinate, which can generally be reached via surgical access, in which one (1) to two (2) platforms can be implanted. Location 508 is within the nasal septum, which can generally be accessed via the nasal passage, in which one (1) to four (4) platforms can be implanted. Location 510 is the ethmoid sinus, which can generally be reached via surgical access, in which one (1) to four (4) platforms can be implanted. In some cases, it may be desirable to also implant platforms in the tissues of the frontal sinus, maxillary sinus, sphenoid sinus (not shown), ethmoid bulla, middle meatus, the osteomeatal complex, the agger nasi, or a combination thereof, where these sinuses can generally be reached via surgical access, and in which one or more platforms can be implanted.

Figure 5B:
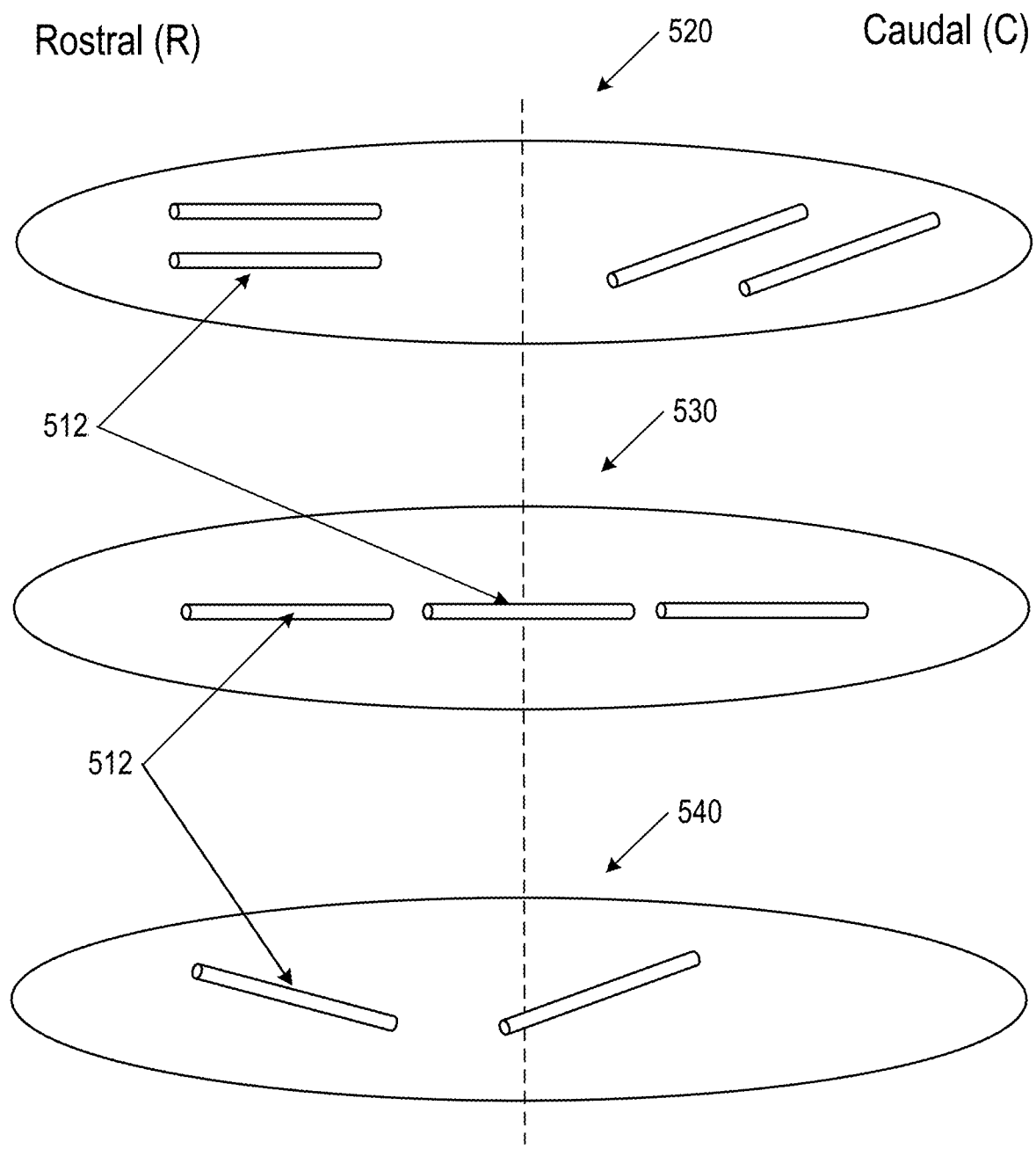
FIG. 5B depicts schematic illustrations of exemplary implantation configurations for drug delivery platforms within sinus turbinates, according to aspects of the disclosure.

FIG. 5B depicts schematic illustrations of exemplary implantation configurations for drug delivery platforms 512 within exemplary sinus turbinates. As shown, a first turbinate 520, a second turbinate 530, and a third turbinate 530 have drug delivery platforms 512 implanted on both or spanning the rostral (R) half (the fore region from the coronal plane of the turbinate) and the caudal (C) half (the rear region from the coronal plane of the turbinate) of each turbinate. Each of the turbinates shown can illustrate implantation strategies for any of the superior turbinate, middle turbinate, or inferior turbinate in a patient. In first turbinate 520, two platforms 512 are implanted in a stacked configuration (relatively above/below each other) the rostral half, effectively parallel to the longitudinal axis of the turbinate, and relatively fore of the center of the first turbinate 512. A relatively shallow implantation strategy such as this may aid in controlling potential bleeding. The distance between stacked drug delivery platforms could range between about one centimeter (1 cm) to about five centimeters (5 cm). In the first turbinate 520 two platforms 512 are also implanted in the caudal half at an inclined angle relative to the longitudinal axis of the turbinate. Implantations at such an angle, coming from an inferior position up into the turbinate, may be preferred to access certain anatomy or specific anatomy that has a more acute need for drug delivery therapy. Such an angled insertion may, of course, also be done in the rostral half of a turbinate. In the second turbinate 520, three platforms 512 are implanted in-line with each other, spanning across from the rostral half to the caudal half of the turbinate. An aligned insertion strategy such as this can be done in series without having to withdraw the delivery device from tissue, and thus may aid in a speed-focused procedure reducing the time necessary to implant all of the platforms 512. In the third turbinate 540, two platforms 512 are implanted generally along the same alignment, generally biased toward the rostral half of the turbinate but crossing the coronal plane (i.e. the middle) of the turbinate. Further both platforms are inclined an angle relative to the longitudinal axis of the turbinate and at different angles relative to each other. This implantation strategy may be performed by manipulation of a delivery device during a single insertion into a tissue, or may be performed with separate insertions entering into the tissue from superior or inferior positions relative to the tissue. It should be appreciated that platforms 512 may also be implanted having a degree of offset from or angle away from the sagittal plane of a respective turbinate.

The drug may be formulated in an implant backbone material such as PLGA by melt-compounding or other appropriate means. Accordingly, an exemplary drug delivery platform can be 40-60% by mass PLGA with the balance of the implant (i.e., the other 60-40% of the mass) being the active drug (e.g. mometasone furoate). The PLGA used as the implant backbone can have an L:G ratio of from 10:90 to 90:10, or any increment of ratios within that range. In some cases, a percentage of the mass of the implant can be a different polymer excipient.

The drug delivery platform may be left within the tissue for any suitable amount of time. It may be desirable for the drug delivery platform to be left in place for a sufficient period to transfer the drug content and deliver one or more drugs to the tissue.

The implant may be removable by surgical means such as creation of tissue pocket and removal. A retrieval aid may be designed on the proximal end of the device to grasp the implant for removal. In other cases the implant may be non-bioabsorbable and removable. In some embodiments, the implant can include a degree of radiopacity, which can facilitate localization of the implant for removal.

In one exemplary application, a drug delivery platform can be implanted into a turbinate. For turbinate injection, procedural pain can be minimized by treating a subject with lidocaine or other local medication or anesthetic. A subject can also be treated with a vasoconstrictor and/or hemostatic to minimize bleeding during the procedure. An appropriate small implant and delivery system injection needle profile, such as 25G or smaller needle, can also be utilized to minimize pain and bleeding.

Multiple drug delivery platforms can be implanted into a tissue, up to a clinically tested safety limit, where the multiple platforms are pre-loaded into a delivery device, either directly or via a cartridge. The number of implants used can thus control the dosage of active agent delivered to a target tissue. For example, at a dosage of 400 μg per platform, four (4) platforms can be pre-loaded into the device and available to implant in order to achieve a target total dosage of 1600 μg for a given tissue area.

After the drug delivery platform is implanted within the target tissue, the active agent is eluted gradually over time. In some variations, a therapeutic level of drug delivery may be provided for a treatment time of from about 1 months to about 12 months, depending on the specific treatment application. In other variations, the treatment time may range from about 2 months to about 3 months, from about 3 months to about 6 months, from about 6 months to about 9 months, or the like. For example, when the method is intended for treatment of allergic rhinitis applications, it may be desirable to maintain a therapeutic level of drug for the duration of an allergy season (e.g., about 2 months to about 3 months). In another example, when the method is intended for treatment of perineal allergic rhinitis applications, it may be desirable to maintain a therapeutic level of drug for as extended a duration of time as possible (e.g., about 6 months to about 12 months) in order to minimize the total number of doctor visits necessary to obtain symptomatic relief. In other cases, the implant can be designed to be non-bioabsorbable and elute up to 2 years.

In some instances, the method of treatment may comprise multiple rounds of treatment. For example, patients who suffer from chronic conditions, such as otitis media, or who experience more than one allergy season (e.g., due to different allergens) each year, may get annual or semi-annual treatments. This can provide for effective continuous therapeutic treatment in addressing the condition and/or sustained relief from the symptoms associated with the condition.

For applications where long-term mechanical support is desirable, the methods described herein may be combined with a separate implantable device. For example, the methods described herein may be combined with the placement of a scaffold or stent placed in the sinus or sinus ostia which can maintain a physical arrangement of sinus anatomy. In some variations, the scaffold or stent may be drug eluting. Where such a scaffold or stent is bioresorbable, the drug delivery platform and that scaffold or stent may have, but do not need to have, the same pharmacokinetic profile. In some variations the scaffold or stent may be expandable (e.g., balloon expandable or self-expanding). In some variations, the scaffold or stent may be bioresorbable (e.g., comprise a bioresorbable synthetic biopolymer), but need not be. Where such a scaffold or stent is bioresorbable, the drug delivery platform and that scaffold or stent may have, but do not need to have, the same bioresorption time profile.

Figure 6:
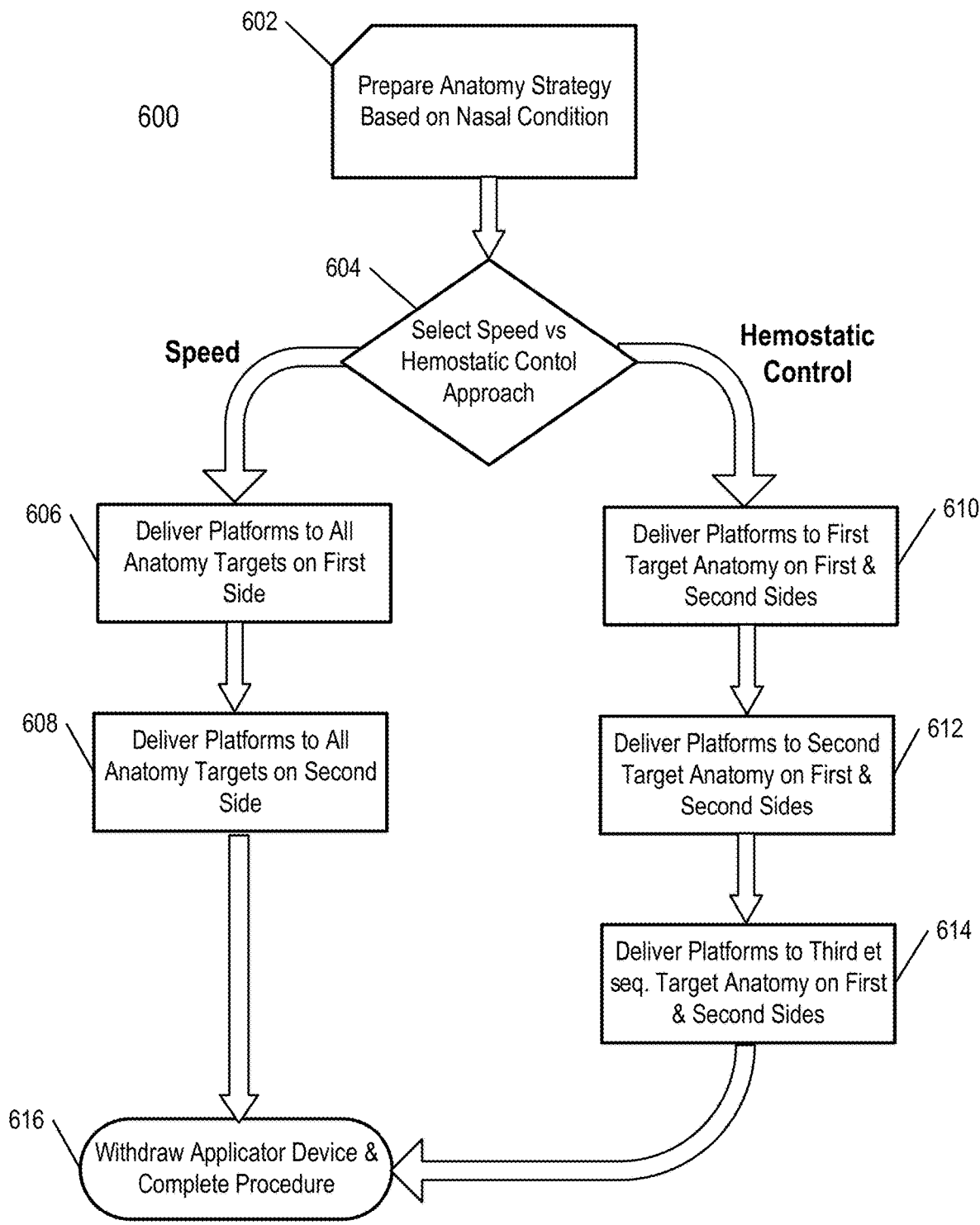
FIG. 6 is a flowchart depicting steps of a method for delivering therapy with a drug delivery platform, according to aspects of the disclosure.

FIG. 6 is a flowchart 600 depicting steps of a method for delivering therapy with a drug delivery platform, specifically to the nasal cavity of a patient. At block 602, a strategy for treatment can be prepared (e.g., by an ENT physician). One element of the treatment strategy can include the number of drug delivery platforms to implant, and by correlation the dosage of drug to use for the treatment. For various strategies, the treatment can include implanting one to ten drug (1-10) delivery platforms in at least one bilateral side of a patient's nasal region. In one example, the treatment strategy may be symmetric, to implant four (4) drug delivery platforms on both the right and left side of a patient's nasal region, where each platform has a dosage of 500 µg of an API, for a total of eight (8) implants and cumulative dosage of 4000 µg of the API. In another example, the treatment strategy may be asymmetric, to implant three (3) drug delivery platforms on the right side of a patient's nasal region and to implant six (6) drug delivery platforms on left side of a patient's nasal region, where each platform has a dosage of 400 µg of an API, for a total of nine (9) implants and cumulative dosage of 5400 µg of the API. In a further example, the treatment strategy may be asymmetric, to implant zero (0) drug delivery platforms on the right side of a patient's nasal region and to implant five (5) drug delivery platforms on left side of a patient's nasal region, where each platform has a dosage of 300 µg of an API, for a cumulative dosage of 1500 µg of the API. It should be understood that treatment strategies can vary to include more or fewer drug delivery platforms, at different API dosages, and with different symmetric or asymmetric implantation site biases as compared to the examples set forth above.

Another element of the treatment strategy can include determining how many drug delivery platforms to implant in specific tissues. In other words, multiple drug delivery platforms can be implanted in a single tissue location. When using an applicator that has multiple platforms loaded on the delivery device, more than one platforms can be implanted during a single insertion of the applicator into the target tissue. Moreover, the medical condition to be treated can guide the number of drug delivery platforms to implant in specific tissues. For example, for the treatment of allergic rhinitis (AR), the strategy can be biased toward having relatively more implants in the inferior regions of the nasal anatomy (e.g., the inferior turbinate). In contrast, for the treatment of chronic rhinosinusitis (CRS), the strategy can be biased toward having relatively more implants in the superior regions of the nasal anatomy (e.g., the middle and superior turbinates). For treatments of anosmia that seek to recover a "persistent loss of smell" for a patient, the strategy can focus on delivery of implants to the olfactory receptors, superior turbinate, or adjacent tissues.

At block 604, a decision can be made to take an approach to delivering treatment that focuses on speed of procedure or on hemostatic control of the patient. The choice between a speed approach or a hemostatic control approach will often depend on the evaluation of the operating physician and the individual receiving implants. A physician familiar with the medical history of a given patent may prefer to take a hemostatic controlled approach to the implantation procedure, if the physician believes the patient is prone to a relatively higher degree of sinus bleeding. Conversely, if the physician considers the duration of the procedure and potential pain management to be a greater concern, the physician may then choose to take a speed approach to the procedure. Additionally or alternatively, a guidance can be provided to the operator delivering implants to a patient, describing one or more speed-focused and hemostatic control-focused approaches to delivering the therapy, and further describing patient characteristics that can help inform a physician in making a decision between a speed-focused or hemostatic control-focused approach.

Proceeding along the speed approach of the flowchart 600, at block 606, using a first applicator, drug delivery platforms are implanted to all selected anatomy on a first bilateral side of a patient's sinuses. In other words, either the patient's left-side or right-side sinuses are chosen as the first side for the procedure, and then the determined number of drug delivery platforms are implanted into the selected tissues. The relevant tissue structures can include the inferior turbinate, the middle turbinate, the superior turbine, the nasal septum, the tissues defining the ethmoid sinuses, or other structures in the nasal passages. One or more drug delivery platforms can be implanted into any one or more of the selected issues. In one example, the therapy strategy can be to implant two platforms into the inferior turbinate, one platform into the middle turbinate, and one platform into the superior turbinate. In another example, the therapy strategy can be to implant one platform into the inferior turbinate, one platform into the middle turbinate, one platform into the superior turbinate, and one platform into a superior region of the nasal septum.

At block 608, using the same or a subsequent applicator, drug delivery platforms are implanted to all selected anatomy on a second bilateral side of a patient's sinuses, the second side being the opposite side from the first bilateral side of block 606. In some implementations of the method, the therapy strategy for the second bilateral side of the sinuses can be the same as for the first bilateral side of the sinuses. In other implementations, the therapy strategy for the second bilateral side of the sinuses can be different than the first bilateral side of the sinuses, using more or fewer drug delivery platforms, and/or implanting more or fewer platforms into the mirrored anatomy (e.g., implanting 3 platforms into the left-side middle turbinate and 4 platforms into the right-side middle turbinate). Following implantation of the drug delivery platforms on the second bilateral side of a patient's sinuses, at block 620, the applicator is withdrawn from and the procedure is complete.

Proceeding along the hemostatic control approach of the flowchart 600, at block 610, using a first applicator, drug delivery platforms are implanted to a first selected anatomy on the first bilateral side of the patient's sinuses and then to a first complementary selected anatomy on the second bilateral side of the patient's sinuses. One approach or controlling bleeding can be to implant multiple platforms in series within a sufficiently large anatomy, such as the inferior turbinate, thereby reducing the total number of insertions and withdrawals into tissues that are needed. For example, at this step two (2) platforms can be implanted in a right-side inferior turbinate followed by two (2) more platforms implanted in the left-side inferior turbinate. For the hemostatic control approach, by switching sides during the procedure, the amount of short-term trauma to the local sinus or nasal region can be reduced, thereby generally avoiding excessive bleeding from local capillaries.

At block 612, using the first applicator, or a subsequent applicator, or a combination thereof, drug delivery platforms are implanted to a second selected anatomy on the first bilateral side of the patient's sinuses and then to a second complementary selected anatomy on the second bilateral side of the patient's sinuses. For example, at this step two (2) platforms can be implanted in the right-side middle turbinate followed by one (1) more platform implanted in the left-side superior turbinate. Continuing along the hemostatic control approach, at block 614, using the first applicator, or a subsequent applicator, or a combination thereof, drug delivery platforms are implanted to a third selected anatomy on the first bilateral side of the patient's sinuses and then to a third complementary selected anatomy on the second bilateral side of the patient's sinuses. For example, at this step two platforms can be implanted in the left-side middle turbinate followed by one (1) more platform in the nasal septum as accessed from the right-side of the patient's nasal region.

It should be appreciated that, for some therapy strategies, there may only be one or two target tissues on a given side of a patient's nasal region that need implantation of a drug delivery platform. Accordingly, in some implementations, block 612 and block 614 may be optional or only require partial (one side) completion. Conversely, as reflected in block 614, further sequential implantations (e.g. a fourth or fifth cycle) may be needed for a given therapy strategy. Following implantation of the drug delivery platforms for the last of the selected target tissues, at block 620, the applicator is withdrawn from and the procedure is complete.

When the methods described herein are combined with a separate implantable device, the drug delivery platform described herein may be delivered to a target tissue before implantation of the other implant, or may be inserted into tissue used post-implantation of the other implant. In variations in which an expandable member is used first, the expandable member device may help pre-dilate the ostia for improved ease of delivery and implantation of the implant to the target tissue. In variations in which the expandable member is used second, the device may help post-dilate the implant for improved apposition. In addition to helping deliver an effective localized dose of a drug, when combined with a scaffold or stent, the methods described here may, for example, maintain the patency of the sinus cavities, and help prevent obstruction caused by adhesions between healing or inflamed mucosal surfaces.

Manufacturing

The devices described herein may be made in any suitable manner. In general, molds may be used to form drug delivery platform designed for specific anatomies, and the materials selected for the drug delivery platform may be based on desired compliance for the specific application.

The drug can be loaded, impregnated, dispersed, saturated, incorporated, packed, or embedded on or within the implant by hot melt extrusion or melt compounding, solvent casting, emulsion based, spray drying, spray coating, injection molding, thermoforming, etc. In the case of hot melt extrusion, the PLGA may be first milled (e.g. by grinding, cryomilling, etc.) to a smaller micro-particle size approximate to that of the drug particles. Then the drug and PLGA may be dry mixed and melt compounded together and extruded and cut to form strands, rods, pellets, etc.

Figure 7:
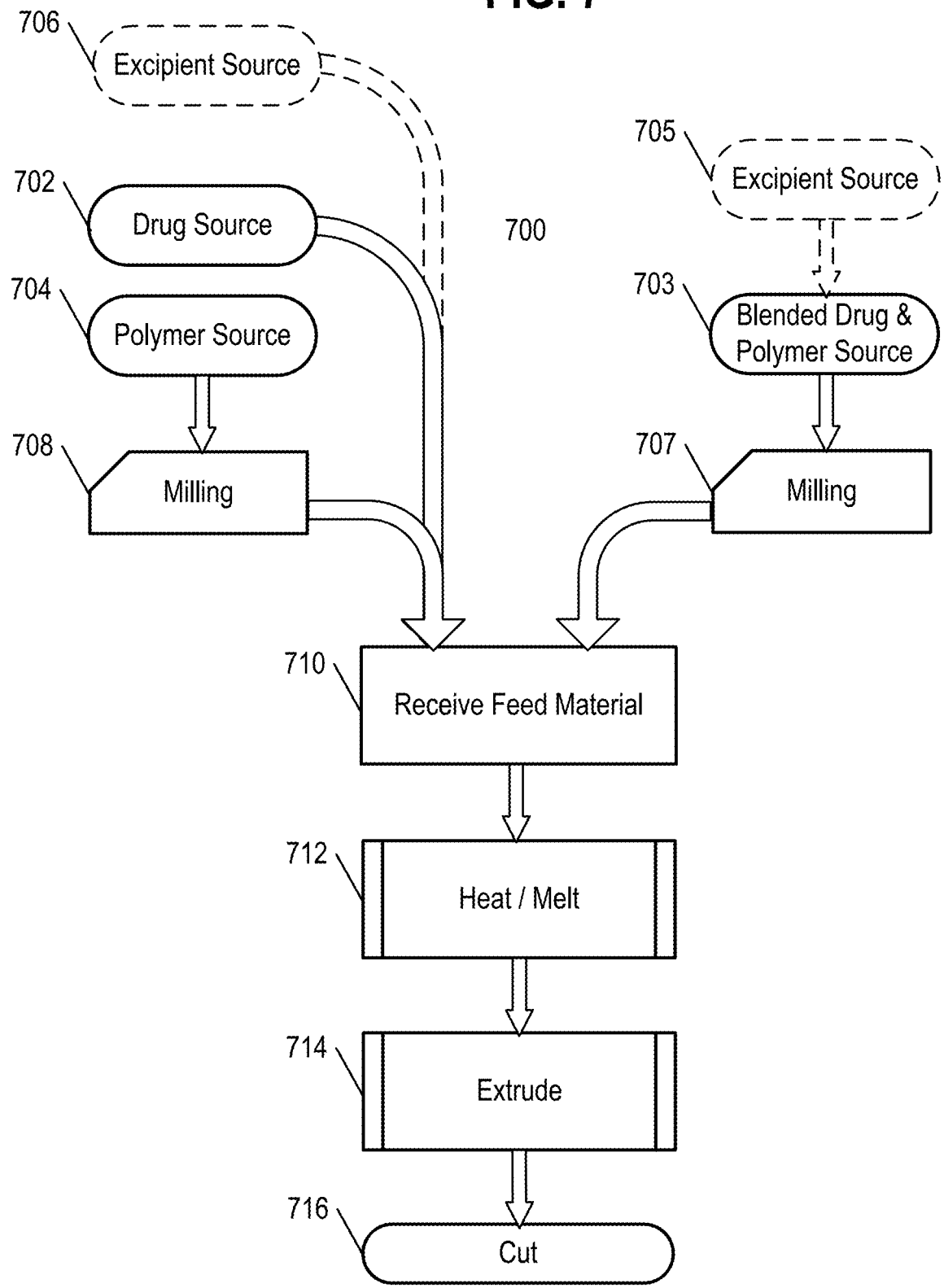
FIG. 7 is a flowchart depicting steps of a method for manufacturing a drug delivery platform, according to aspects of the disclosure.

FIG. 7 is a flowchart 700 depicting steps of a method for manufacturing a drug delivery platform, in part via hot-melt extrusion. General details regarding hot-melt extrusion processes can be found in "AAPS PharmSciTech", Vol. 17, No. 1, pp. 20-42 (February 2016), which is expressly incorporated by reference herein. Initially, two pathways are shown for preparing the feed material to be run through the extrusion process. On the first pathway, at block 702 a source of the drug (alternatively referred to as the "active pharmaceutical ingredient" or "API") used for the drug delivery platform is provided, where the API is generally provided in a particle form. It should be understood that one or more APIs can be supplied at this step, for example to provide for the desired therapeutic effect or effects. At block 704, a source for the polymer material used to co-form the drug delivery platform with the API is provided. Similarly, understood that one or more polymer materials can be supplied at this step, for example to provide for a target biodegradation and drug-release profile. Optionally, at block 706, one or more excipients can be provided concurrently to form the drug delivery platform with the separately provided API materials and polymer materials. At block 708, the polymer material is milled such that the polymer material is of a size similar to the API material. For the components in this process, particularly the API, cryomilling can be an advantageous technique to use in order to control (i.e., dissipate) the heat generated from the mechanical impact and friction milling processes, such that the API does not proceed through unintentional chemical reactions or degradations due to heat picked up by the polymer during the milling step. At block 710, the API, milled polymer, and any optional excipient is received from this first pathway, generally in a hopper of a hot-melt extrusion system.

Along the second pathway, at block 703 a source of combined API materials and polymer materials is provided. Again, it should be understood that one or more API material and one or more polymer materials can be provided to achieve a target therapeutic effect and drug-release profile. Optionally, at block 705, one or more excipients can be provided to co-form the drug delivery platform with the combined or blended API and polymer materials. At block 707, the blended source of API and polymer materials are milled such that the API and polymer materials have a similar particle size. Again, cryomilling can be an advantageous technique to use in order to control heat such that the API does not proceed through unintentional chemical reactions or degradations due to heat during the milling step. At block 710, the milled API and polymer, and any optional excipient is received from this second pathway, generally in a hopper of a hot-melt extrusion system.

With regard to cryomilling of the polymer as descried herein, the cryomilling process can include the following steps and parameters to achieve a functional, target milling result. In some implementations, the source material polymer used can be precooled before being milled, for a period of time from three (3) to ten (10) minutes, or longer as needed. Following precooling, the grinding of the polymer can proceed for a period of time from two (2) to six (6) minutes. In some implementations, multiple precooling-milling cycles (e.g., 2 cycles, 3 cycles, 4 cycles, etc.) can be used to achieve a target polymer particle size. The duration of mixing can aid in providing for a uniform distribution of polymer and API, where the overall or aggregate duration of mixing can range from ten minutes to sixty minutes (10-60 min) or longer. The volume of the source polymer milled can range from about five milliliters to about fifty milliliters (5-50 mL), and this volume of polymer can be kept at a temperature as cold as negative 196° C. through the use of liquid nitrogen or liquid oxygen. The size of the cryomilled polymer can be about one hundred microns (100 μm), and in some aspects can further range from about ten micrometers to about four hundred micrometers (10-400 μm). At a particle size of from about 10-400 μm, the polymer can have an inherent viscosity that is relatively high enough, when combined with an API, to retain structure after extrusion, molding, or other implant-formation processes. Moreover, at a particle size of from about 10-400 μm, the polymer is relatively small enough when combined with an API (such as mometasone furoate) to cover the drug when melted and mixed together. Further, having the milled polymer and the API being about the same size, can aid in providing for a uniform distribution of polymer and API.

At block 712, the hot-melt extruder system heat and/or melts material that has been received at block 710. The hot-melt extruder moves the API and polymer materials (and any excipient) along a screw assembly at a temperature above the melting point of the input materials. In some implementations, the temperature of the HME is controlled so that polymer is melted such that it substantively surrounds the API. The screw assembly of the holt-melt extruder can be a single-screw extruder (SSE), a twin-screw extruder (TSE) or a multi-screw extruder (MSE). With a relatively uniform distribution of polymer and API as the feed material into the hot-melt extruder, the resulting output compound material will have a similarly uniform distribution of polymer and API. The operational parameters of the screw assembly can be configured as appropriate to the size, characteristics, and volume of input materials in order to form a product with uniform distribution of the constituent components. In some implementations, the hot-melt extruder can have a rotating orifice with a desired shape to produce the helical channels as the implant is extruded.

At block 714, the product of the hot-melt extruder system is output and cut to a target length appropriate for implantation as a drug delivery platform.

In current examples of the drug delivery platform, the backbone of the implant is formed of PLGA and the active therapeutic is mometasone furoate. It should be understood from reading this disclosure as a whole that other identified bioerodible polymers and materials can be used as the backbone for the implant, and that other identified drugs can be used as the active therapeutic of the implant. The PLGA and the mometasone furoate can be formed as the drug delivery platform in combination by hot melt extrusion, achieving a high drug loading while maintaining the drug in a crystalline structure, while also having a consistent manufacturability meeting a target specification. In a hot melt extrusion process, both the drug and the backbone material (e.g., PLGA) can be provided as particles, both having a particle size of about ten to about five hundred micrometers (10-500 μm) and dry blended prior to extrusion. As needed, the drug and PLGA can be pelletized by grinding, milling, cryomilling, or other mechanical techniques to reach a target particle size. Optionally, the blend of the drug and PLGA can be compounded in a first melt, and then pelletized into particles of a target size.

The compounded drug-and-PLGA pellets, or mixed population of drug pellets and PLGA pellets, can be continuously extruded in the hot melt process and then hot drawn or cold drawn into the designed size and shape of the drug delivery platform. The extruded drug delivery platform can then be cut to length.

Further improvements to the manufacturing process include batch size scale-up of PLGA cryomilling and drug and PLGA hot melt extrusion. Automated feed, laser micrometer measurement of extrudate size and automated sorting and cutting are further manufacturing improvements. Further improvements may include an additional process where the pellets from the first hot melt extrusion process are put through a second hot melt extrusion process in order to further improve drug content uniformity.

In further implementations, using different polymers and/or different APIs, the milling and/or the HIVIE process may be similarly altered to achieve an implant with the target structural, drug-elution, and bioresorption characteristics. For example, with other APIs having a different size, the corresponding polymer can be milled to a similar or smaller size. In other embodiments, different excipients can be used to change the elution and/or biodegradation rate of the platform. In other embodiments, the drug delivery platform can be a dual-drug delivery platform, with two API complexed together or individually incorporated with a polymer backbone. Such dual-drug formulations can be, for example, a corticosteroid and an antihistamine, or a corticosteroid and an antibiotic. By extension, drug delivery platforms can also be formed with three APIs triplexed or individually incorporated with a polymer.

In an alternative embodiment, the drug delivery platform can also have one or more coating layers that are coated, packed, or layered on the surface of the platform. The one or more coating layers can be applied onto the platform by dip coating, spray coating, or other such processes. The one or more coating layers can be configured to slow the release of API from the drug delivery platform and/or to slow the rate of bioresorption and extend the amount of time the platform remains intact within tissue. The one or more coating layers can be formulated to have the same API as the core body of the drug delivery platform at the same or a different dosage, a different API as the core body of the drug delivery platform, or no API.

In some embodiments, the drug delivery platform can be formed to have a uniform distribution of API along the length of the platform, leading to a similarly uniform area of drug elution from the platform. Conversely, the drug delivery platform can be formed to have a gradient of API distribution along the length of the platform (e.g., the distal end of the platform has a relatively higher proportion of drug than the proximal end, as delivered by an applicator), leading to a similarly biased drug elution pattern from the platform. In other embodiments, the drug delivery platform can be formed to have a uniform distribution of API radially out from the center of the platform, which can lead to a generally constant rate or a decreasing rate of drug elution over the period of biodegradation of the implant. Conversely, the drug delivery platform can be formed to have a biased distribution of API radially out from the center of the platform (e.g., the center of the platform has a relatively higher concentration of drug than the surface area of the platform), leading to a generally constant rate, decreasing rate, or increasing rate of drug elution over the period of biodegradation of the implant. In other words, by use of a configured gradient, the drug delivery platform can be formed to have (i) a fast-then-slow release rate thereby achieving a relatively high dose early in the treatment and a relatively low dose later in the treatment duration, (ii) a slow-then-fast release rate thereby achieving a relatively low dose early in the treatment and a relatively high dose later in the treatment duration, or (iii) a relatively constant release rate thereby achieving a consistent dose throughout the treatment duration.

Target specifications for an exemplary embodiment of the implant include dimensions compatible with a 25G needle, at least 50% drug loading (where at least 50% of the implant is the active therapeutic), mechanical integrity for loading into the delivery device, mechanical integrity for implanting into the target tissue, and drug release and bioresorption for a period of 6-9 months.

In addition to the particular components of the drug formulation, the manufacturing methods described herein may help minimize drug loss during delivery to the treatment site and maximize drug delivery upon implantation and contact with tissue.

EXAMPLES

The following examples are illustrative only and should not be construed as limiting the disclosure in any way.

Example 1

Drug Release and Pharmacokinetics

Figure 8A:
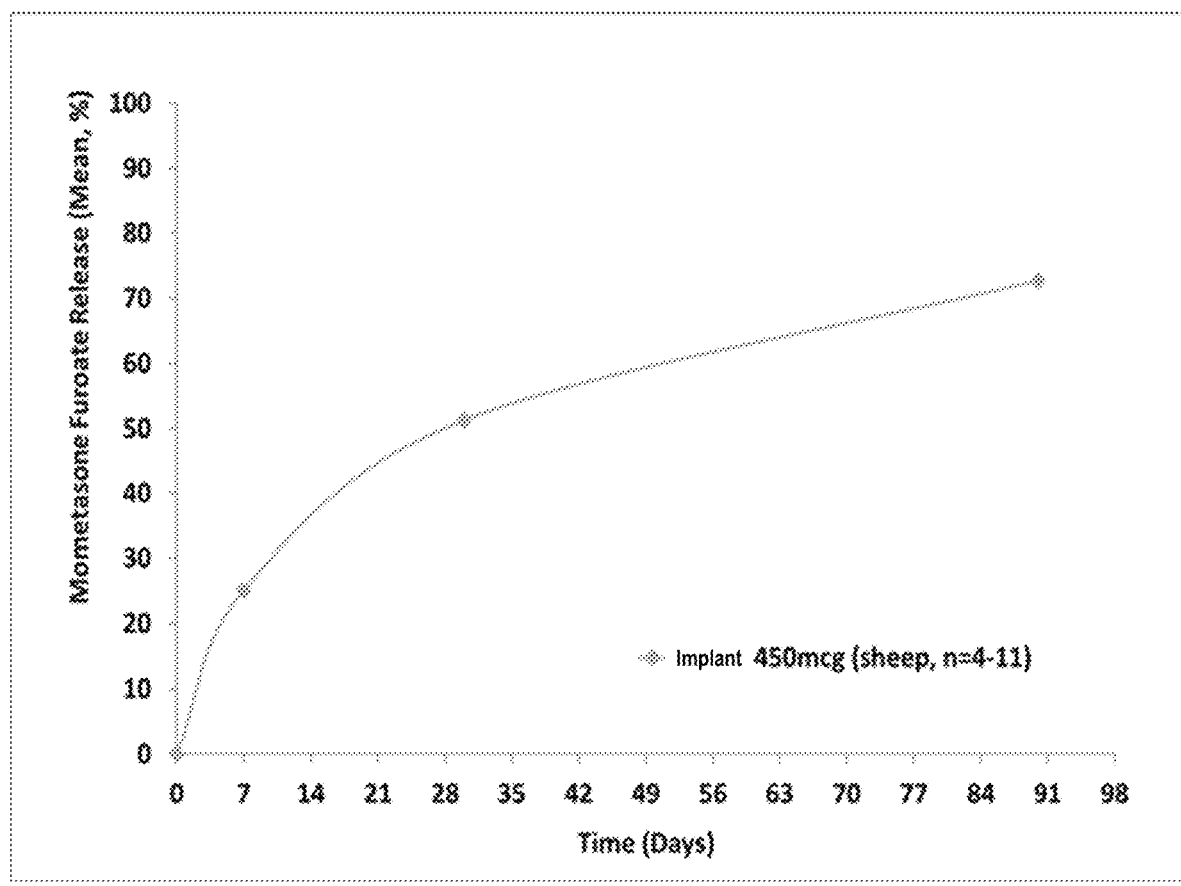
FIG. 8A is a graph depicting experimental results of a comparison study across exemplary three different drug delivery platforms, showing the comparative cumulative drug release over time, according to aspects of the disclosure.
Figure 8B:
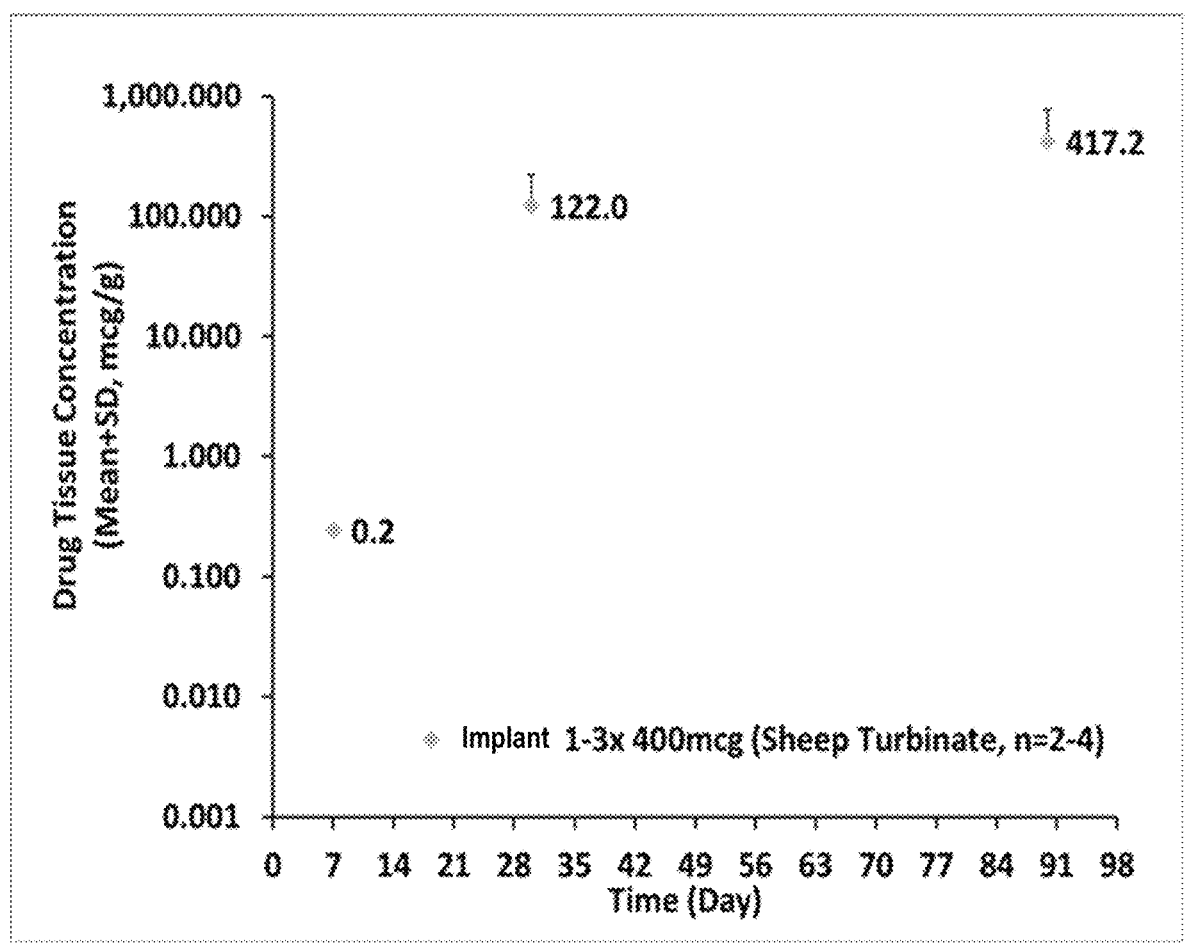
FIG. 8B is a graph depicting experimental results of a comparison study across exemplary three different drug delivery platforms, showing the comparative concentration of drug within tissue over time, according to aspects of the disclosure.

FIGS. 8A and 8B are graphs depicting experimental results of a first study for this drug delivery platform, illustrating the cumulative drug release over time in a sheep turbinate model. Specifically, the implants loaded with mometasone furoate were studied for their cumulative release (mean %) over time within subject animals. FIG. 8A shows the comparative cumulative drug release over time, while FIG. 8B shows the comparative concentration of drug within tissue over time.

With regard to the implants, mometasone furoate loaded drug delivery platforms were manufactured with 50% mometasone furoate in either poly(D,L-lactide-co-glycolide) 50:50 or poly(D,L-lactide-co-glycolide) 75:25 by micro-compounder. This formed material was cut into 10 mm lengths. Each drug delivery platform (one example specifically shown as FIG. 1A) contained an average of 450 µg mometasone furoate ("MF"). Sample were sterilized by electron-beam radiation and then implanted in sheep turbinates using a 23-gauge needle injection device (specifically the implantation device shown in FIG. 2A). The drug delivery platforms were then explanted at various timepoints as shown in the data of FIGS. 8A and 8B. Explanted platforms were measured by high performance liquid chromatography (HPLC) for mometasone furoate concentration. Turbinate tissue and blood plasma from the subject sheep were measured by liquid chromatography-mass spectrometry (LC-MS) for mometasone furoate concentration. As seen and discussed in further detail in FIGS. 8A and 8B and TABLE 1 below, the drug release from the implants were demonstrated to be approximately 25% at 7 days, 50% at 30 days, and 70% at 90 days post-implantation. The respective concentrations of mometasone furoate in local tissue (micrograms of MF per gram of tissue) were measured to be 0.2 µg/g at 7 days, 122.0 µg/g at 30 days, and 417.2 µg/g at 90 days. Mometasone furoate has shown therapeutic effectiveness at concentration levels of 0.1 µg/g, and so accordingly, all of the timepoints measured exhibited a therapeutic level of MF concentration. Blood samples taken from the subject sheep were also measured for mometasone furoate (representative of systemic concentration), but all blood samples at all measured timepoints registered as below the lower limit of quantification ("LLOQ"), where the lower limit of qualification for the testing protocol is 20 pg/mL.

Figure 9:
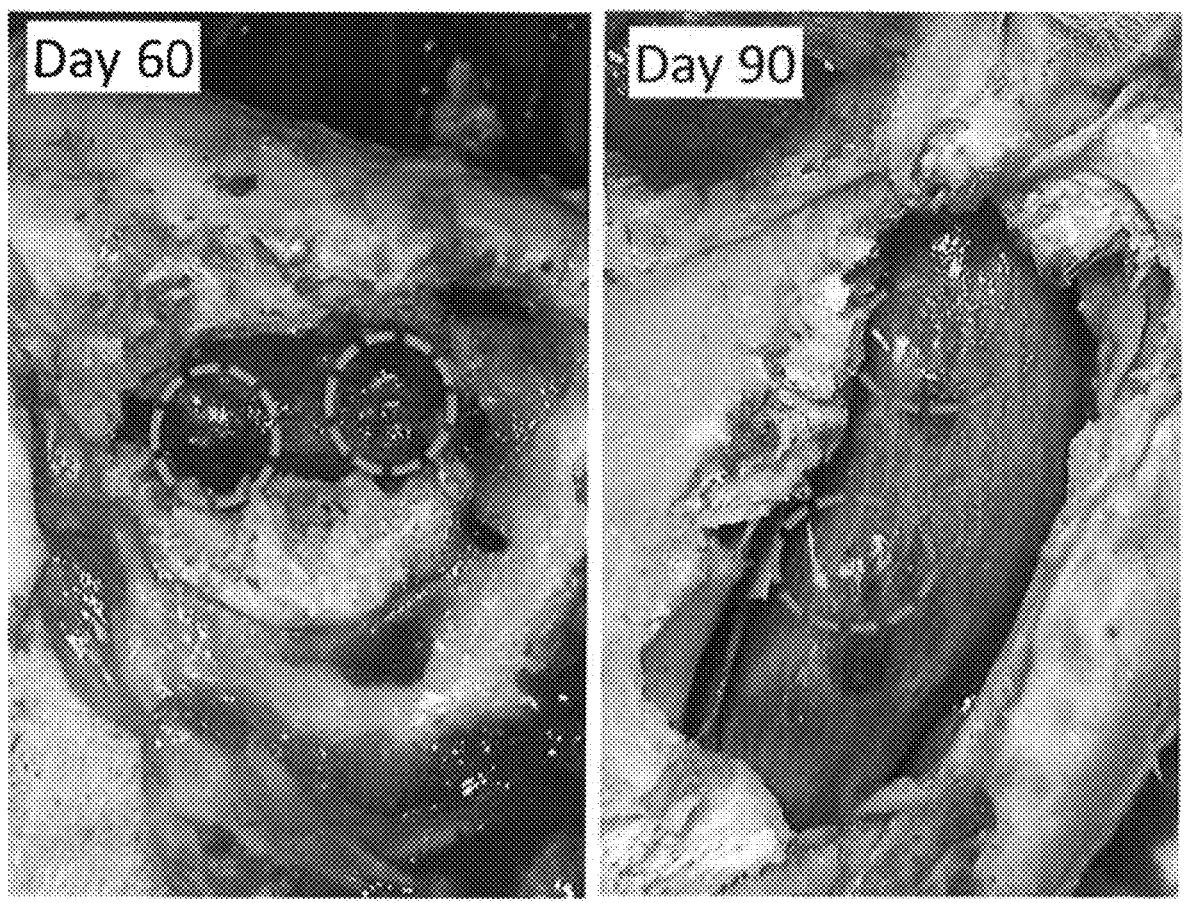
FIG. 9 shows a pair of images of explantation sites from sheep turbinates of exemplary drug delivery platforms, according to aspects of the present disclosure.

Focusing again on the implants, FIG. 9 shows a pair of images of explantation sites (i.e., the target tissue after extraction of implants) of the drug delivery platforms from sheep turbinate at day 60 (left hand image) and at day 90 (right hand image). Each turbinate shown has two locations (indicated by the dashed-line circles) where at each location one (1) implant drug delivery platform was implanted. Generally, the inferior turbinate of the sheep subjects were used for testing, having an average length of 8.5 cm.

Figure 10:
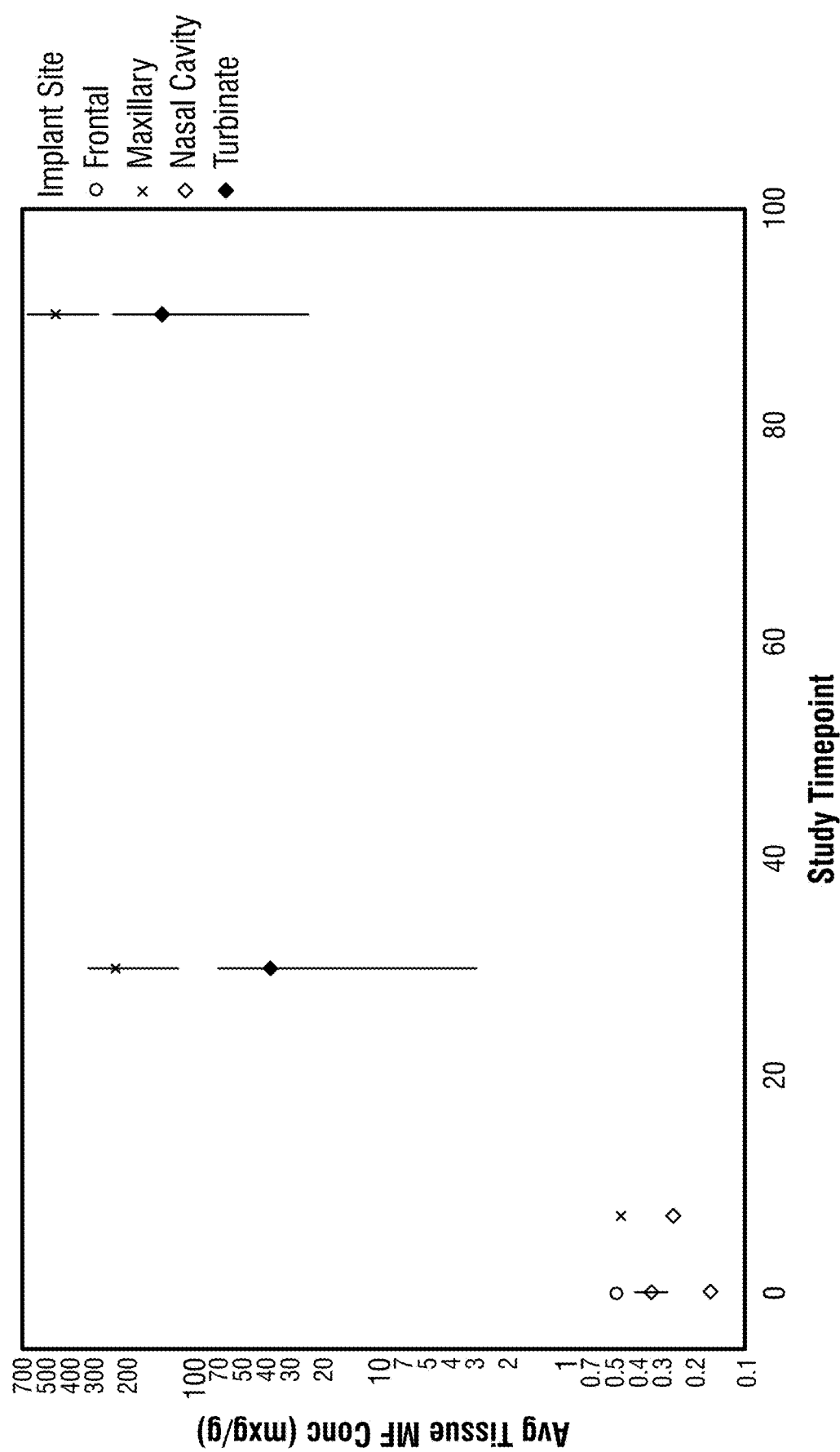
FIG. 10 is a graph depicting experimental results of a first study, for a drug delivery platform as implanted into various parts of a nasal anatomy, according to aspects of the disclosure.

FIG. 10 is a graph depicting experimental results of the implant drug delivery platforms as implanted into various parts of the sheep nasal anatomy. Specifically shown is the average in vivo tissue concentrations (µg/g) over time from the implant drug delivery platforms in different sheep nasal tissues. TABLE 1 summarizes the data shown in the graph of FIG. 10.

TABLE 1

| Nasal Implant Location | DRUG CONCENTRATION IN TISSUE | | | |
|---|---|---|---|---|
| | 0 Days | 7 Days | 30 Days | 90 Days |
| Frontal | 0.49 | NS | NS | NS |
| Maxillary | 0.32 ± 0.06 | 0.47 | 242.33 ± 124.36 | 531.04 ± 219.98 |
| Nasal Cavity | 0.16 | 0.24 ± 0.02 | NS | NS |
| Turbinate | NS | NS | 35.81 ± 32.99 | 139.06 ± 116.27 |

NS = no sample

In TABLE 1 (and in TABLES 3 and 5 below), some of the data points have standard deviation values, which reflects that two or more drug delivery platforms were explanted from the indicated sites at the given timepoint. Other data points only have one measurement, which reflects that only one drug delivery platform was explanted from the indicated site at the given time point.

As can be seen least from the maxillary sinus and the turbinate tissue data, the amount of drug persists and even increases at 30 days and 90 days following implantation. By extrapolation, this data can predict that the implanted drug delivery platforms have a drug delivery profile of up to a six (6) month release or longer.

Example 2

Implant Delivery & Recovery Feasibility; Formulation Analysis; Drug Release & Pharmacokinetics In a second study for this drug delivery platform, carried out in three cohorts (A, B1, & B2), the feasibility of the implant delivery and recovery (using sheep tissue) was evaluated along with the drug release efficacy and pharmacokinetics in the tissue recovered from the sheep. Further, two alternative formulations of an API, in this case mometasone furoate, were tested in comparison to each other. All of the implants were prepared similarly to the implants described in Example 1 above, specifically again being loaded with 450 µg MF. The second study was expanded to have the three cohorts as more samples, timepoints, and formulations were added to the analysis.

Exemplary drug delivery platforms having the first formulation of drug were implanted in various sinus anatomy of sheep subjects, then explanted at various timepoints and the relevant tissues were examined for mometasone furoate concentration. As shown in TABLE 2, at the Day 0 timepoint, in frontal sinus, maxillary sinus, and nasal cavity tissues, with a single 450 µg MF implant in each tissue, the amount of MF transferred to the tissue was relatively low but still above the therapeutic level of 0.1 µg MF/g tissue. At the Day 30 timepoint, in both left and right sides of maxillary sinus and turbinate tissues, with three 450 µg MF implants, a therapeutic amount of MF was present in all of the examined tissues. Further at the Day 90 timepoint, again in both left and right sides of maxillary sinus and turbinate tissues, with three 450 µg MF implants (1350 µg MF total dose), a therapeutic amount of MF was present in three of the four the examined tissues.

TABLE 2

DRUG CONCENTRATION IN TISSUE, FORMULATION 1

| Study Part | Timepoint (Days) | Animal | Implant Site | Side | Total Dose (µg) | Tissue MF Concentration (µg/g) |
|---|---|---|---|---|---|---|
| A | 0 | AC-01 | Frontal | L | 450 | 0.49 |
|   |   |   | Maxillary | R | 450 | 0.32 |
|   |   |   | Nasal Cavity | L | 450 | 0.16 |
| B1 | 30 | D30-01 | Maxillary | L | 1350 | 337.91 |
|   |   |   |   | R | 1350 | 568.49 |
|   |   |   | Turbinate | L | 1350 | 103.88 |
|   |   |   |   | R | 1350 | 247.21 |
|   | 90 | D90-01 | Maxillary | L | 1350 | 790.66 |
|   |   |   |   | R | 1350 | 2392.79 |
|   |   |   | Turbinate | L | 1350 | 16.10 |
|   |   |   |   | R | 1350 | 772.65 |

Following this, exemplary drug delivery platforms having the second formulation of drug were implanted in various sinus anatomy of sheep subjects, then explanted at various timepoints and the relevant tissues were examined for mometasone furoate concentration. As shown in TABLE 3, at the Day 7 timepoint, in the maxillary sinus and nasal cavity tissues, with a single 450 µg MF implant in each tissue, the amount of MF transferred to the tissue was relatively low but still above the therapeutic level of 0.1 µg MF/g tissue. At the Day 30 timepoints, in both left and right sides of maxillary sinus and turbinate tissues, with three 450 µg MF implants, a therapeutic amount of MF was present in four of the six examined tissues. At the Day 60 timepoint, in left and right sides turbinate tissues, with three 450 µg MF implants, a therapeutic amount of MF was present in both of the examined tissues. At the Day 90 timepoint, again in both left and right sides of maxillary sinus and turbinate tissues, with three 450 µg MF implants (1350 µg MF total dose), a therapeutic amount of MF was present in six of the six examined tissues. At the Day 120 timepoint, in left and right sides turbinate tissues, with three 450 µg MF implants, a therapeutic amount of MF was present in both of the examined tissues.

TABLE 3

DRUG CONCENTRATION IN TISSUE, FORMULATION 2

| Study Part | Timepoint (Days) | Animal | Implant Site | Side | Total Dose (µg) | Tissue MF Concentration (µg/g) |
|---|---|---|---|---|---|---|
| A | 7 | D7-01 | Maxillary | R | 450 | 0.47 |
|   |   |   | Nasal Cavity | R | 450 | 0.24 |
| B1 | 30 | D30-02 | Maxillary | L | 1350 | 787.36 |
|   |   |   |   | R | 1350 | 1214.21 |
|   |   |   | Turbinate | L | 1350 | 2.12 |
|   |   |   |   | R | 1350 | 18.09 |

TABLE 3-continued

DRUG CONCENTRATION IN TISSUE, FORMULATION 2

| Study Part | Timepoint (Days) | Animal | Implant Site | Side | Total Dose (μg) | Tissue MF Concentration (μg/g) |
|---|---|---|---|---|---|---|
| | 90 | D90-02 | Maxillary | L | 1350 | 1702.04 |
| | | | | R | 1350 | 1487.04 |
| | | | Turbinate | L | 1350 | 244.16 |
| | | | | R | 1350 | 635.87 |
| B2 | 30 | D30-03 | Turbinate | L | 1350 | 52.87 ± 74.11 |
| | | | | R | 1350 | 191.16 ± 66.98 |
| | 60 | D60-01 | Turbinate | L | 1350 | 1741.38 ± 1546.76 |
| | | | | R | 1350 | 975.62 ± 728.07 |
| | 90 | D90-03 | Turbinate | L | 1350 | 219.24 ± 193.99 |
| | | | | R | 1350 | 1293.90 ± 1211.53 |
| | 120 | D120-01 | Turbinate | L | 1350 | 54.27 ± 24.79 |
| | | | | R | 1350 | 21.41 ± 24.88 |

Figure 11:
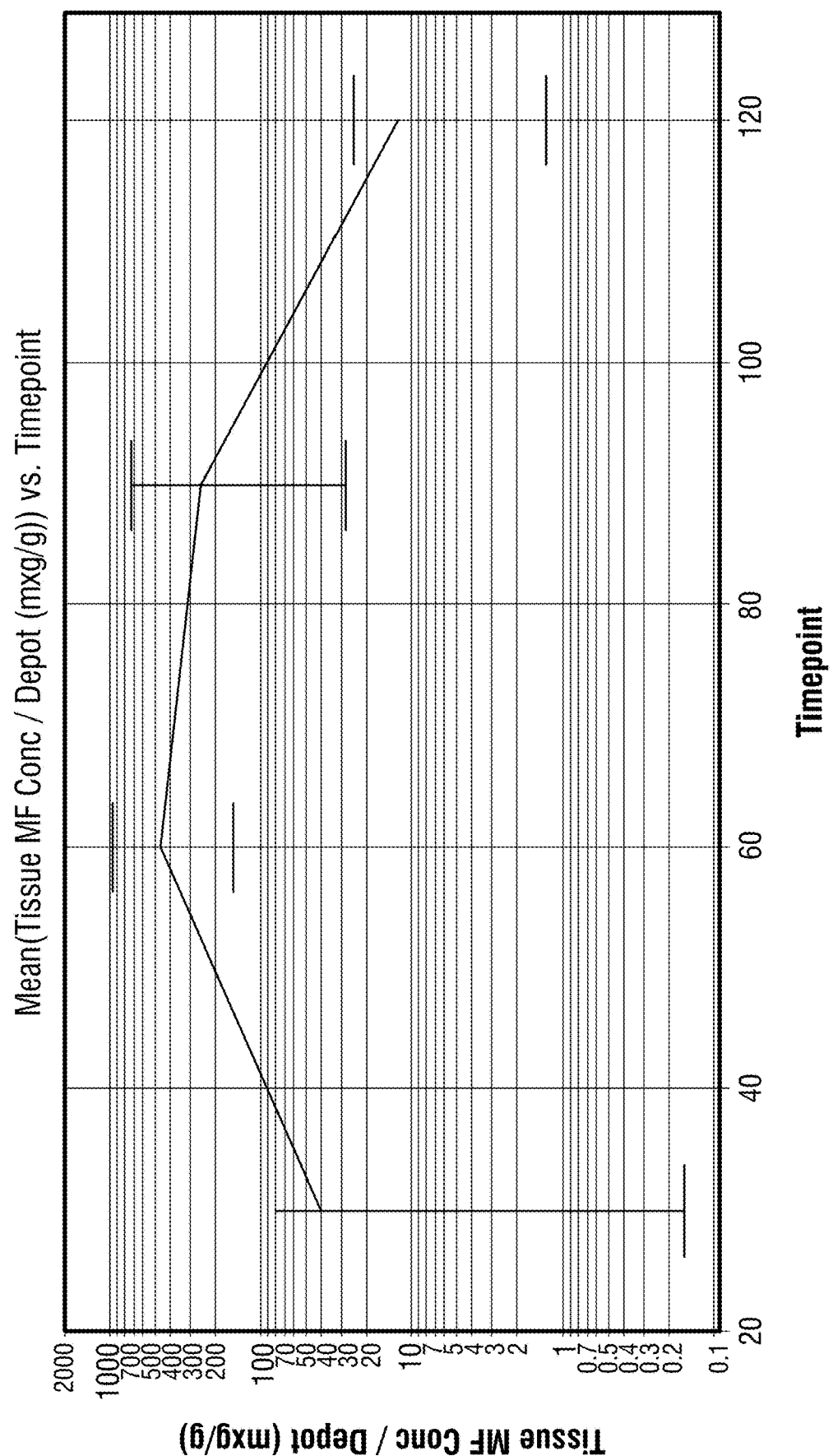
FIG. 11 is a graph depicting experimental results of a second study, for a drug delivery platform as implanted into various parts of a nasal anatomy, according to aspects of the disclosure.

FIG. 11 is a graph depicting the experimental results of TABLE 3, for the drug delivery platform using Formulation 2. In the graph of FIG. 11, it can be seen that the peak of MF distribution in tissue was at Day 60, with the curve of MF concentration present in the tissue extending over the timepoints of Days 30, 60, 90, and 120.

Figure 12:
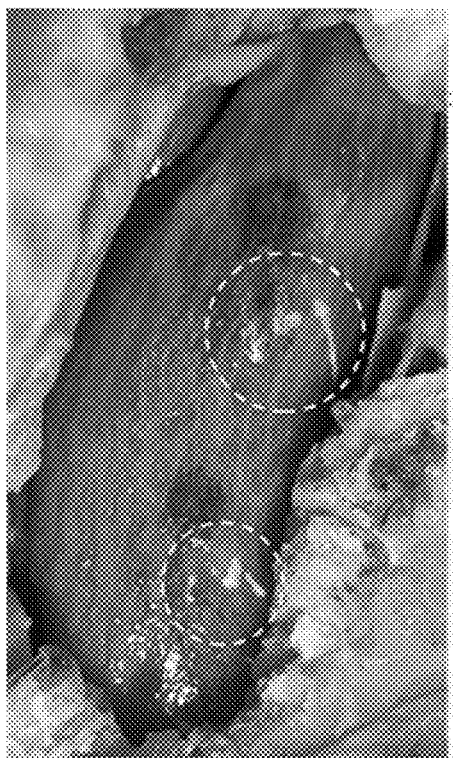
FIG. 12 shows, from the second study, four images of explantation sites from sheep turbinates of exemplary drug delivery platforms, according to aspects of the present disclosure.
Figure 12:
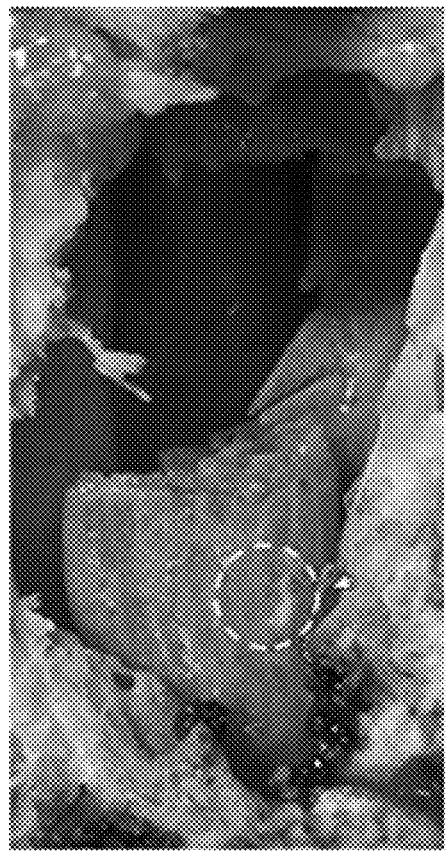
Figure 12:
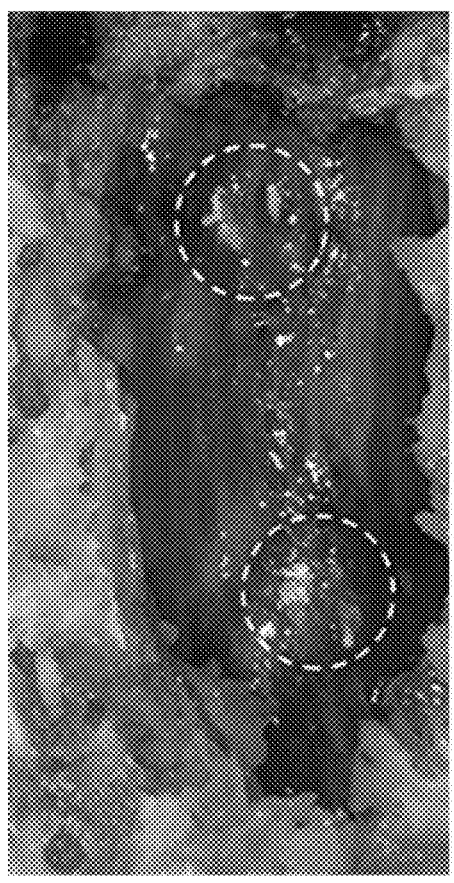
Figure 12:
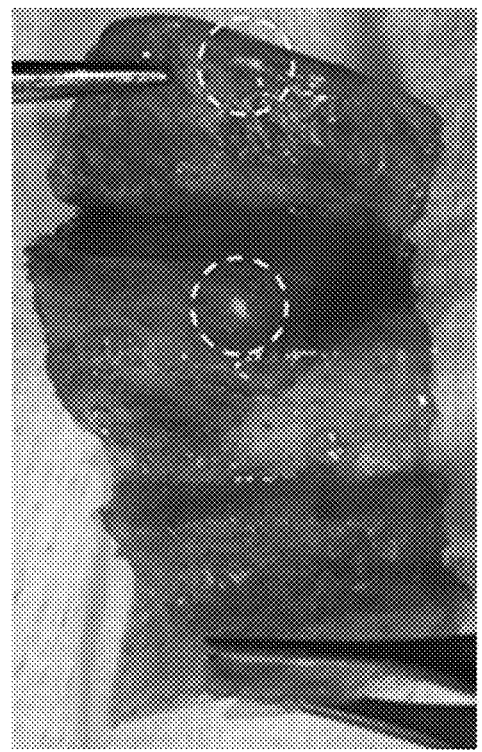

FIG. 12 shows four images of explantation sites of the drug delivery platforms from sheep turbinate at Day 60 (top-left hand image), Day 90 (top-right hand image), and Day 120 (bottom two images). These implants were Formulation 2 drug delivery platforms. Each turbinate shown has locations (indicated by the dashed-line circles) where at each location one (1) implant drug delivery platform was implanted.

The data as shown in TABLES 2 and 3 and FIG. 11, and as seen in FIG. 12, show support for the capability of the drug delivery platforms as described herein to deliver therapeutic amounts of drug to target tissues up to at least 120 days following implantation.

As shown in TABLE 4, blood samples taken from the subject sheep of the second study were also measured for mometasone furoate, as a representative of systemic concentration. Nearly all blood samples at all measured timepoints registered as below the lower limit of quantification of 20 pg/mL, indicating that there is no significant systemic effect of MF delivery from the implanted platform.

TABLE 4

BLOOD PLASMA CONCENTRATION

| | Animal/Dose | | | |
|---|---|---|---|---|
| Timepoint | D30-03 5400 μg MF | D60-01 5400 μg MF | D90-03 5400 μg MF | D120-01 5400 μg MF |
| Predose | <LLOQ | <LLOQ | <LLOQ | <LLOQ |
| 30 min. | <LLOQ | <LLOQ | <LLOQ | <LLOQ |
| 1 hr. | <LLOQ | <LLOQ | <LLOQ | <LLOQ |
| 2 hr. | <LLOQ | <LLOQ | <LLOQ | <LLOQ |
| 4 hr. | <LLOQ | <LLOQ | <LLOQ | <LLOQ |
| Day 1 | <LLOQ | <LLOQ | <LLOQ | <LLOQ |
| Day 3 | <LLOQ | <LLOQ | <LLOQ | <LLOQ |
| Day 7 | <LLOQ | <LLOQ | <LLOQ | <LLOQ |
| Day 14 | <LLOQ | <LLOQ | <LLOQ | <LLOQ |
| Day 30 | NS | <LLOQ | <LLOQ | <LLOQ |
| Day 60 | NS | <LLOQ | <LLOQ | <LLOQ |
| Day 90 | NS | NS | 25.3 | <LLOQ |
| Day 120 | NS | NS | NS | <LLOQ |

LLOQ = 20 pg/mL;
NS = no sample

The implants recovered following explantation were examined for the amount of drug remaining in the platforms. As shown in TABLE 5, for both Formulation 1 and Formulation 2, a therapeutically effective amount of drug remained on the platforms at all Day 0, Day 30, and Day 90 timepoints, indicating that sufficient drug remained on the platforms to continue eluting into the tissue to thereby deliver therapy to the respective tissues.

TABLE 5

DRUG REMAINING IN EXPLANTED PLATFORMS

| | Study Part | Timepoint | Animal | Implant Site | Side | MF Remaining (μg) |
|---|---|---|---|---|---|---|
| Formulation 1 | A | 0 | AC-01 | Ear | L | 202.70 ± 73.94 |
| | | | | | R | 199.09 ± 51.41 |
| | | | | Frontal | L | 149.11 |
| | | | | Maxillary | R | 208.94 ± 29.78 |
| | | | | Nasal Cavity | L | 238.79 ± 3.80 |
| | | | | | R | 125.29 ± 50.72 |

TABLE 5-continued

DRUG REMAINING IN EXPLANTED PLATFORMS

| | Study Part | Timepoint | Animal | Implant Site | Side | MF Remaining (µg) |
|---|---|---|---|---|---|---|
| | B1 | 30 | D30-01 | Maxillary | L | 172.70 ± 50.65 |
| | | | | Turbinate | R | 323.78 ± 203.29 |
| | | 90 | D90-01 | Maxillary | L | 63.02 ± 50.26 |
| | | | | | R | 79.05 ± 46.17 |
| Formulation 2 | A | 7 | D7-01 | Ear | L | 282.51 ± 54.25 |
| | | | | | R | 214.95 ± 46.61 |
| | | | | Maxillary | R | 231.86 |
| | | | | Nasal Cavity | R | 227.65 ± 82.51 |
| | B1 | 90 | D90-02 | Maxillary | L | 25.84 ± 23.05 |
| | | | | | R | 22.45 |
| | | | | Turbinate | R | 51.25 |
| | B2 | 30 | D30-03 | Turbinate | L | 335.71 ± 345.88 |
| | | | | | R | 215.90 ± 111.42 |

In sum, as presented in TABLE 6, the drug delivery platforms used in the second study delivered mometasone furoate to the tissues in which they were implanted at a therapeutic level for at least 90 days, and with Formulation 2 for at least 120 days.

TABLE 6

SUMMARY OF SECOND STUDY PHARMACOKINETICS

| | Implantation Time (Days) | In-Vivo MF Drug Release From Implant (%) | | | |
|---|---|---|---|---|---|
| | | Mean | Std Dev | Std Err | N |
| Formulation 1 | 0 | 40.02 | 14.93 | 3.99 | 14 |
| | 30 | 47.9 | 12.39 | 6.2 | 4 |
| | 90 | 73.74 | 13.37 | 6.68 | 4 |
| Formulation 2 | 7 | 45.92 | 12.6 | 3.8 | 11 |
| | 30 | 66.05 | 6.12 | 2.5 | 6 |
| | 60 | 76.53 | 11.8 | 8.34 | 2 |
| | 90 | 86.09 | 12.87 | 4.86 | 7 |
| | 120 | 95.49 | 2.21 | 1.27 | 3 |

Accordingly, this data shows the implanted drug delivery platforms have a drug delivery profile for at least a four (4) month release, and by extension a longer duration of drug release of six (6) months or longer.

Example 3

Drug Dose & Distribution Analysis

In a third study for this drug delivery platform, drug dosing was tested by varying the number of drug delivery platforms implanted within a turbinate. All of the implants were prepared similarly to the implants described in Example 1 above, specifically again being loaded with 450 µg MF. The compound of the MF and implant used the formulation identified as Formulation 2 in Example 2 above. In TABLE 7, with all tissues examined at Day 30 following implantation, dosing was examined using a "minimal dose" of two (2) implants in a turbinate, a "low dose" of three (3) implants in a turbinate, and a "nominal dose" of six (6) implants in a turbinate. The implants were positioned within the turbinates in either a relatively rostral or caudal location, leaving the opposite end of the turbinate without implants in the immediate area of that tissue. Each turbinate tissue from the samples was tested in two parts, isolating the portion of the turbinate having the implants from the portion without, to evaluate the amount of drug migration from the implants to the region without implants.

TABLE 7

DOSING STUDY, DRUG TISSUE CONCENTRATION

| Implants per Turbinate | Implants per Tissue Sample | Total Implant Dose per Tissue Sample | Tissue MF Concentration (µg/g) | | |
|---|---|---|---|---|---|
| | | | Mean | Std. Dev. | N |
| Minimal Dose: 2 implants/turbinate | 0 | 0 | 4.33 | 9.55 | 5 |
| | 2 | 900 | 0.02 | 0.02 | 2 |
| Low Dose: 3 implants/turbinate | 0 | 0 | 56.38 | 123.04 | 5 |
| | 3 | 1350 | 13.53 | 26.73 | 4 |
| Nominal Dose: 6 implants/turbinate | 0 | 0 | 14.58 | — | 1 |
| | 3 | 1350 | 9.89 | 8.81 | 4 |

Figure 13:
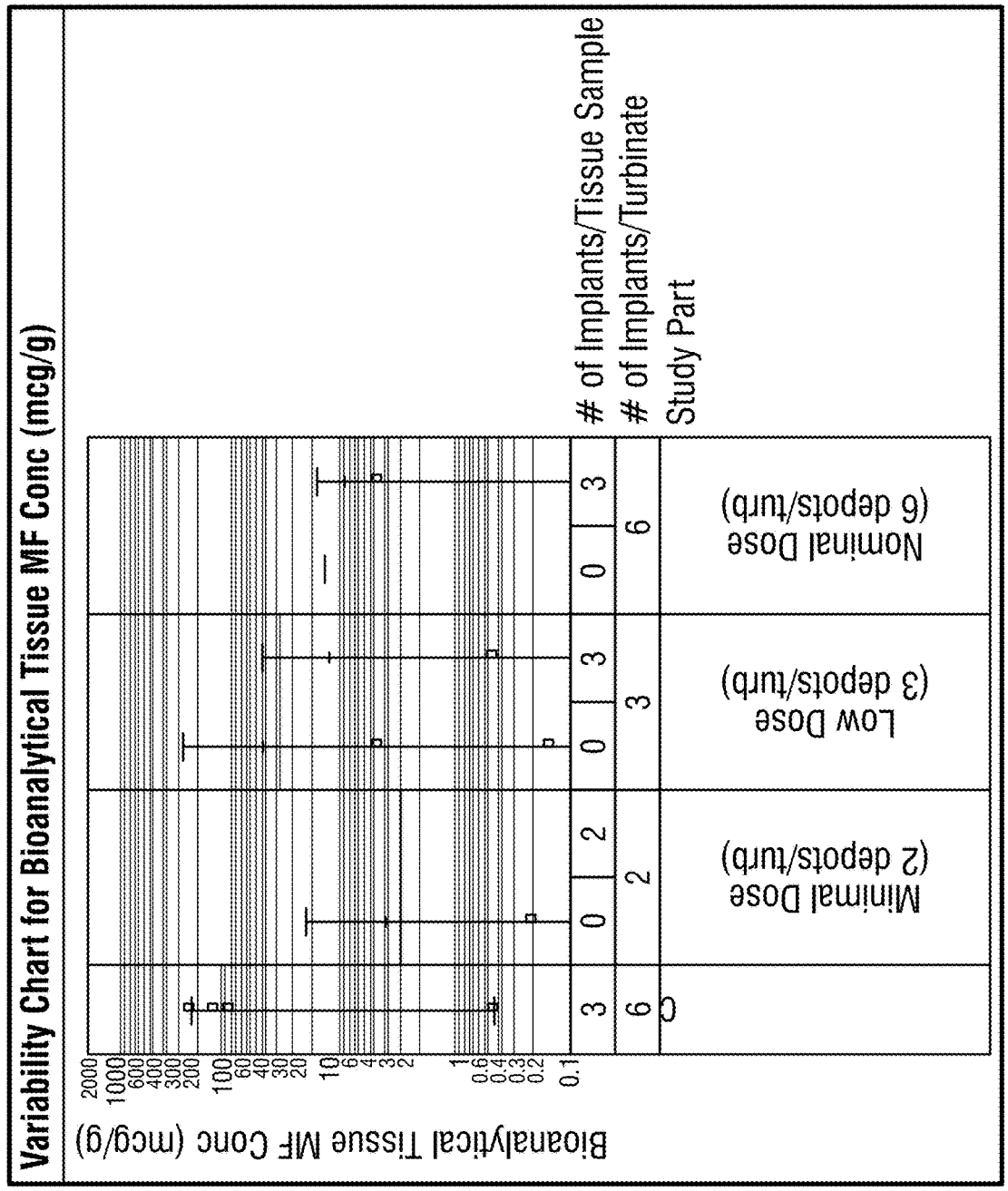
FIG. 13 is a graph depicting experimental results of a third study, for a drug delivery platform as implanted into various parts of a nasal anatomy, according to aspects of the disclosure.

FIG. 13 is a table plotting the data shown in TABLE 7, alongside a control reference taken from Formulation 2 in Example 2 above. As can be seen, the tissue samples without implants contained therapeutic levels of MF at Day 30, showing that the MF from the implants migrated through the turbinate tissue and was present at therapeutic levels for at least thirty days thereafter.

Figure 14:
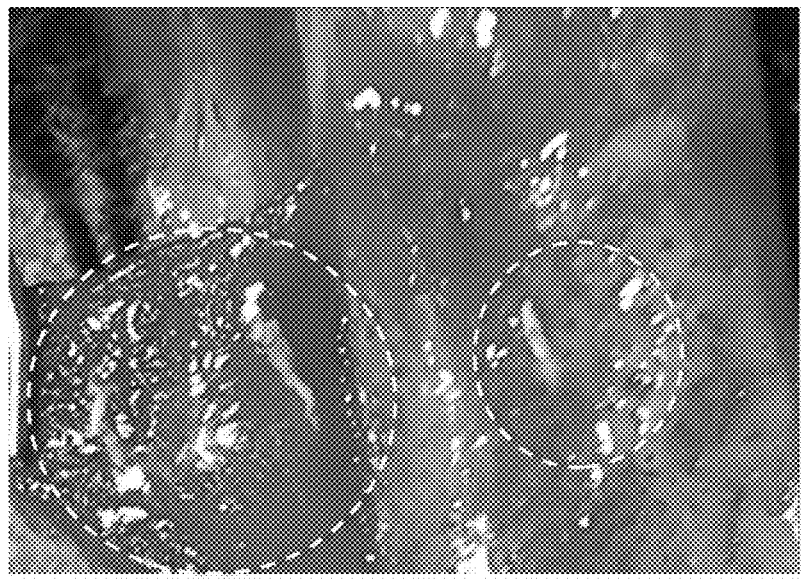
FIG. 14 shows, from the third study, four images of explantation sites from sheep turbinates of exemplary drug delivery platforms, according to aspects of the present disclosure.
Figure 14:
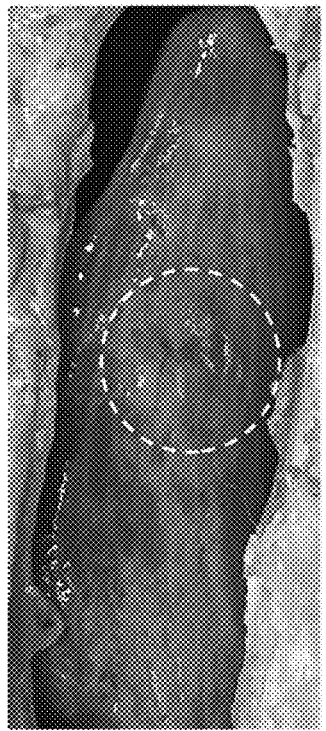
Figure 14:
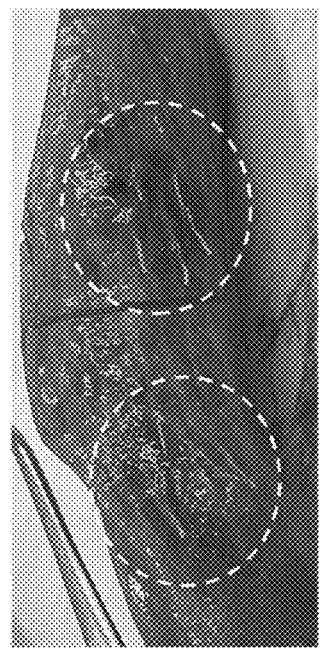
Figure 14:
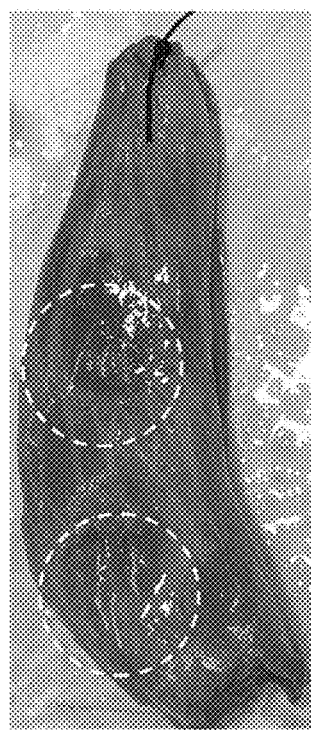

FIG. 14 shows four images of explantation sites of the drug delivery platforms from the right turbinate of three different sheep at Day 30 (three left hand images), and drug delivery platforms from the left turbinate of a sheep at Day 180 (right hand image). Each turbinate shown has locations (indicated by the dashed-line circles) where at each location one (1) implant drug delivery platform was implanted. For the Day 30 samples, all of the implants were able to be removed from the mucosa of the turbinate tissue. For the Day 180 sample, the implant remained visible but was softer as compared to the Day 30 samples, and was correspondingly more difficult to retrieve.

As shown in TABLE 8, blood samples taken from the subject sheep of the third study were also measured for mometasone furoate, as a representative of systemic concentration. As in the earlier testing, nearly all blood samples at all measured timepoints registered as below the lower limit of quantification of 20 pg/mL, indicating that there is no significant systemic effect of MF delivery from the implanted platform.

TABLE 8

BLOOD PLASMA CONCENTRATION

| | Animal/Dose | | | | |
|---|---|---|---|---|---|
| Timepoint | D30-01 2700 µg MF | D30-02 5400 µg MF | D30-03 5400 µg MF | D180-01 2700 µg MF | D180-02 5400 µg MF |
| Predose | <LLOQ | <LLOQ | <LLOQ | <LLOQ | <LLOQ |
| 30 min. | <LLOQ | <LLOQ | <LLOQ | <LLOQ | <LLOQ |
| 1 hr. | <LLOQ | <LLOQ | <LLOQ | 22.5 | <LLOQ |
| 2 hr. | <LLOQ | <LLOQ | <LLOQ | <LLOQ | <LLOQ |
| 4 hr. | <LLOQ | <LLOQ | <LLOQ | <LLOQ | <LLOQ |
| Day 1 | <LLOQ | <LLOQ | <LLOQ | <LLOQ | <LLOQ |
| Day 3 | <LLOQ | <LLOQ | <LLOQ | <LLOQ | <LLOQ |
| Day 7 | <LLOQ | <LLOQ | <LLOQ | <LLOQ | <LLOQ |
| Day 14 | <LLOQ | <LLOQ | <LLOQ | <LLOQ | <LLOQ |
| Day 30 | NS | <LLOQ | <LLOQ | <LLOQ | <LLOQ |

LLOQ = 20 pg/mL;
NS = no sample

Figure 15:
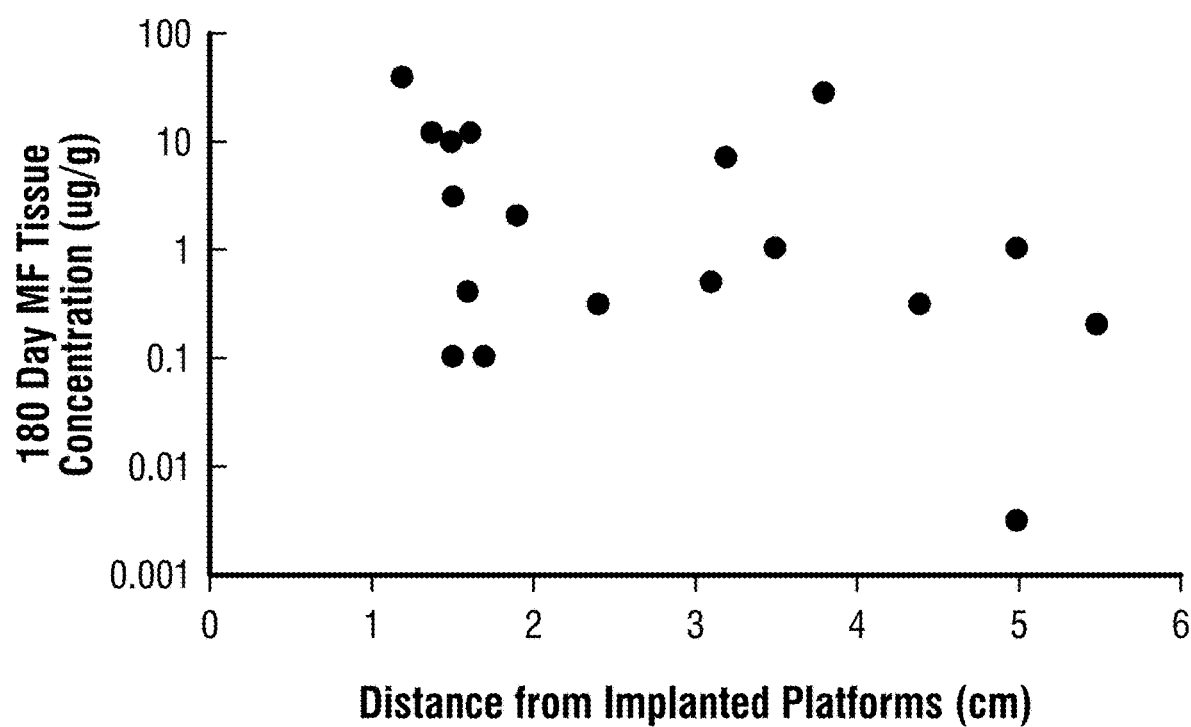
FIG. 15 is a graph depicting experimental results from the third study, showing the distance that drug moved through tissue from implanted drug delivery platforms, according to aspects of the disclosure

FIG. 15 is a graph depicting further experimental results from the third study, examining the distance that the mometasone furoate moved through the sheep turbinate tissues starting from implanted drug delivery platforms. Here, a total of eighteen (18) drug delivery platforms were implanted into the left and right turbinates of a sheep, with nine (9) turbinates on each side in mirrored locations. At Day 180, the tissue was harvested and examined for MF concentration. Measuring from each implanted platform, MF was found at therapeutic levels ranging from 0.1 µg/g to 40 µg/g, at distances ranging from 1.2 cm to 5.5 cm away from the respective platforms. This further supports the showing that drug from an implanted platform does migrate through local tissue over 180 days.

Again, the implants recovered following explantation were examined for the amount of drug remaining in the platforms. As shown in TABLE 9, implants were recovered at Day 30 from four animals, where the implants were explanted from either the left or the right turbinate, and either from the rostral or caudal region of each turbinate. As can be seen from the data, at Day 30 sufficient drug remained on the platforms to continue eluting into the tissue to thereby deliver therapy to the respective tissues.

TABLE 9

DRUG REMAINING IN EXPLANED PLATFORMS

| | | % of MF Drug Content per Sample Weight | | |
|---|---|---|---|---|
| Animal | Location | Sum | Mean | Std. Dev. |
| D30-01 | Lt. Caudal | 112.13 | 37.38 | 12.95 |
| | Rt. Rostral | 141.22 | 47.08 | 17.85 |
| D30-02 | Lt. Rostral | 80.90 | 40.45 | 4.70 |
| | Rt. Caudal | 165.13 | 55.04 | 21.76 |
| | Rt. Rostral | 157.67 | 52.56 | 8.12 |
| D30-04 | Lt. Rostral | 28.94 | 28.94 | — |
| | Rt. Caudal | 118.92 | 59.46 | 20.14 |
| D30-05 | Lt. Rostral | 113.10 | 37.70 | 1.07 |
| | Rt. Caudal | 151.05 | 50.35 | 5.93 |

In sum, as presented in TABLE 10, the drug delivery platforms used in the third study delivered mometasone furoate to the tissues in which they were implanted at a therapeutic level for at least 180 days.

TABLE 10

SUMMARY OF THIRD STUDY PHARMACOKINETICS

| Implantation Time (Days) | In-Vivo MF Drug Release From Implant (%) | | | |
|---|---|---|---|---|
| | Mean | Std Dev | Std Err | N |
| 30 | 42.51 | 18.8 | 4.1 | 21 |
| 180 | 79.94 | 13.59 | 3.04 | 20 |

Accordingly, this data shows that the implanted drug delivery platforms have a drug delivery profile for a six (6) month release and longer.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are intended to serve as a shorthand method of referring individually to each separate value falling within the range, or gradients thereof, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. The invention is susceptible to various modifications and alternative constructions, and certain exemplary embodiments thereof are shown in the drawings and have been described above in detail. Variations of those preferred embodiments, within the spirit of the present invention, may become apparent to those of ordinary skill in the art upon reading the foregoing description. The inventors expect skilled artisans to employ such variations as appropriate, and the inventors intend for the invention to be practiced otherwise than as specifically described herein. Accordingly, it should be understood that there is no intention to limit the invention to the specific form or forms disclosed, but on the contrary, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating symptoms of a condition, the method comprising:
    inserting a distal tip of a needle submucosally into a target tissue;
    delivering a plurality of bioresorbable drug delivery platforms from the needle into the target tissue, each of the bioresorbable drug delivery platforms of the plurality of bioresorbable drug delivery platforms comprising a polymer scaffold of from about 40% to about 60% of the drug delivery platform by mass and a therapeutic agent contained within the polymer scaffold of from about 40% to about 60% of the drug delivery platform by mass, wherein a sum of the percentage by mass of the polymer scaffold and the percentage by mass of the therapeutic agent is equal to or less than 100%;
    allowing the therapeutic agent to elute from each of the bioresorbable drug delivery platforms of the plurality of bioresorbable drug delivery platforms over a sustained period of time; and
    allowing each of the bioresorbable drug delivery platforms of the plurality of bioresorbable drug delivery platforms to biodegrade within the target tissue,
    wherein each of the bioresorbable drug delivery platforms of the plurality of bioresorbable drug delivery platforms is configured in size and mechanical integrity to pass through the needle for implantation submucosally into the target tissue, and such that the sustained period of time is from about 6 months to about 9 months,
    wherein each of the bioresorbable drug delivery platforms of the plurality of bioresorbable drug delivery platforms has a biased distribution of the therapeutic agent radially out from a center of each of the bioresorbable drug delivery platforms of the plurality of bioresorbable drug delivery platforms.

2. The method of claim 1, wherein the condition is a sinus related condition.

3. The method of claim 1, wherein the condition is an otic related condition.

4. The method of claim 1, wherein the condition is a throat related condition.

5. The method of claim 1, wherein the polymer scaffold of each of the bioresorbable drug delivery platforms of the plurality of bioresorbable drug delivery platforms comprises a core region and a main body, and further wherein the core region of each of the bioresorbable drug delivery platforms of the plurality of bioresorbable drug delivery platforms comprises a formulation of polymer material and the therapeutic agent that is different than a formulation of the main body.

6. The method of claim 1, wherein a core region of each of the bioresorbable drug delivery platforms of the plurality of bioresorbable drug delivery platforms comprises a hollow channel, and wherein the hollow channel of the core region of each of the bioresorbable drug delivery platforms of the plurality of bioresorbable drug delivery platforms is configured to hold a volume of the therapeutic agent.

7. The method of claim 1, wherein the therapeutic agent of each of the bioresorbable drug delivery platforms of the plurality of bioresorbable drug delivery platforms comprises a steroidal anti-inflammatory agent selected from the group consisting of mometasone furoate, fluticasone propionate, and dexamethasone.

8. The method of claim 1, wherein the polymer scaffold of each of the bioresorbable drug delivery platforms of the plurality of bioresorbable drug delivery platforms comprises a polymer material that is ester end capped, acid end capped, or a combination thereof.

9. The method of claim 8, wherein the polymer material of each of the bioresorbable drug delivery platforms of the plurality of bioresorbable drug delivery platforms comprises poly(D,L-lactide-co-glycolide), and wherein a molar ratio of the poly(D,L-lactide-co-glycolide) ranges from 0% to 100% lactide and from 0% to 100% glycolide.

10. A method for treating symptoms of a condition, the method comprising:
    inserting a distal tip of a needle submucosally into a target tissue;
    delivering a plurality of bioresorbable drug delivery platforms from the needle into the target tissue, each of the bioresorbable drug delivery platforms of the plurality of bioresorbable drug delivery platforms comprising an active agent of from about 40% to about 60% of the drug delivery platform by mass and contained within a polymer scaffold of from about 40% to about 60% of the drug delivery platform by mass, wherein a sum of the percentage by mass of the polymer scaffold and the percentage by mass of the active agent is equal to or less than 100%;
    allowing a dose of the active agent to be released from each of the bioresorbable drug delivery platforms of the plurality of bioresorbable drug delivery platforms over a sustained period of time, wherein the release from each of the bioresorbable drug delivery platforms of the plurality of bioresorbable drug delivery platforms over the sustained period of time provides a therapeutically effective amount of the active agent in the target tissue; and allowing each of the bioresorbable drug delivery platforms of the plurality of bioresorbable drug delivery platforms to biodegrade within the target tissue, wherein each of the bioresorbable drug delivery platforms of the plurality of bioresorbable drug delivery platforms is configured in size and mechanical integrity to pass through the needle for implantation submucosally into the target tissue, and such that the sustained period of time is from about 6 months to about 9 months, wherein each of the bioresorbable drug delivery platforms of the plurality of bioresorbable drug delivery platforms has a biased distribution of the active agent radially out from a center of each of the bioresorbable drug delivery platforms of the plurality of bioresorbable drug delivery platforms.

11. The method of claim 10, wherein the delivering comprises injecting the plurality of bioresorbable drug delivery platforms from the needle into the target tissue.

12. The method of claim 11, wherein the plurality of bioresorbable drug delivery platforms is injected from the needle using a revolver loading structure or a magazine loading structure.

13. The method of claim 10, wherein the dose of the active agent of each of the bioresorbable drug delivery platforms of the plurality of bioresorbable drug delivery platforms is between about 400 µg and about 1350 µg.

14. The method of claim 10, wherein at least 25% of the dose of the active agent is released from each of the bioresorbable drug delivery platforms of the plurality of bioresorbable drug delivery platforms after 7 days.

15. The method of claim 10, wherein at least 50% of the dose of the active agent is released from each of the bioresorbable drug delivery platforms of the plurality of bioresorbable drug delivery platforms after 30 days.

16. The method of claim 10, wherein at least 70% of the dose of the active agent is released from each of the bioresorbable drug delivery platforms of the plurality of bioresorbable drug delivery platforms after 90 days.

17. The method of claim 10, wherein releasing the active agent of each of the bioresorbable drug delivery platforms of the plurality of bioresorbable drug delivery platforms over 7 days provides the therapeutically effective amount of the active agent in the target tissue of at least 0.1 µg/g.

18. The method of claim 10, wherein releasing the active agent of each of the bioresorbable drug delivery platforms of the plurality of bioresorbable drug delivery platforms over 7 days provides the therapeutically effective amount of the active agent in the target tissue of at least 0.2 µg/g.

19. The method of claim 10, wherein releasing the active agent of each of the bioresorbable drug delivery platforms of the plurality of bioresorbable drug delivery platforms over 30 days provides the therapeutically effective amount of the active agent in the target tissue of at least 122 µg/g.

20. The method of claim 10, wherein releasing the active agent of each of the bioresorbable drug delivery platforms of the plurality of bioresorbable drug delivery platforms over 90 days provides the therapeutically effective amount of the active agent in the target tissue of at least 417 µg/g.

21. The method of claim 10, wherein the release from each of the bioresorbable drug delivery platforms of the plurality of bioresorbable drug delivery platforms over the sustained period of time further provides a therapeutically effective amount of the active agent in a tissue adjacent the target tissue.

22. The method of claim 10, wherein the active agent of each of the bioresorbable drug delivery platforms of the plurality of bioresorbable drug delivery platforms comprises a steroidal anti-inflammatory agent selected from the group consisting of mometasone furoate, fluticasone propionate, dexamethasone, and combinations thereof.

23. The method of claim 10, wherein the target tissue is a paranasal sinus, a sinus ostium, an inferior turbinate, a middle turbinate, a superior turbinate, a nasal cavity, a nasal vestibule, a nasal septum, nasal polypoid tissues, an osteomeatal complex, a nasopharynx, an adenoid tissue, or a combination thereof.

24. The method of claim 10, wherein the delivering includes using a speed focused approach.

25. The method of claim 10, the delivering includes a hemostatic control focused approach.

26. The method of claim 10, wherein the delivering reduces systemic exposure of the active agent.

\* \* \* \* \*